(12) United States Patent
Ichiyanagi

(10) Patent No.: US 12,258,589 B2
(45) Date of Patent: Mar. 25, 2025

(54) GLYCATED HEMOGLOBIN OXIDASE VARIANT AND METHOD FOR MEASUREMENT

(71) Applicant: Kikkoman Corporation, Noda (JP)

(72) Inventor: Atsushi Ichiyanagi, Chiba (JP)

(73) Assignee: Kikkoman Corporation, Chiba (JP)

( * ) Notice: Subject to any disclaimer, the term of this patent is extended or adjusted under 35 U.S.C. 154(b) by 522 days.

(21) Appl. No.: 16/643,358

(22) PCT Filed: Aug. 31, 2018

(86) PCT No.: PCT/JP2018/032389
§ 371 (c)(1),
(2) Date: Feb. 28, 2020

(87) PCT Pub. No.: WO2019/045052
PCT Pub. Date: Mar. 7, 2019

(65) Prior Publication Data
US 2020/0283741 A1 Sep. 10, 2020

(30) Foreign Application Priority Data
Aug. 31, 2017 (JP) .................................. 2017-167890

(51) Int. Cl.
C12N 9/02 (2006.01)
C12Q 1/26 (2006.01)

(52) U.S. Cl.
CPC ............. *C12N 9/0083* (2013.01); *C12Q 1/26* (2013.01); *C12Y 114/99003* (2013.01)

(58) Field of Classification Search
None
See application file for complete search history.

(56) References Cited

U.S. PATENT DOCUMENTS 5,370,990 A 12/1994 Staniford et al.
6,033,867 A 3/2000 Kato et al.
(Continued)

FOREIGN PATENT DOCUMENTS

JP 05-033997 B2 5/1993
JP 11-127895 A 5/1999
(Continued)

OTHER PUBLICATIONS

Lenters-Westra et al., Clin. Chem. Lab. Med. 55(9): 1426-1434 (2017; published Apr. 22, 2017).*
(Continued)

*Primary Examiner* — Erin M. Bowers
(74) *Attorney, Agent, or Firm* — Foley & Lardner LLP

(57) ABSTRACT

Provided is a glycated hemoglobin oxidase with small measurement error or without deviation of the measured value from the true value regarding a sample containing glycated abnormal hemoglobin. Provided are a glycated hemoglobin oxidase comprising an amino acid sequence in which the amino acid at the position corresponding to position 113, 109, 106, or 102 of the amino acid sequence of SEQ ID NO: 1 is substituted with an amino acid other than a positively-charged amino acid, such as glutamic acid, alanine, or aspartic acid as well as a method and a reagent kit for measurement of glycated hemoglobin using such glycated hemoglobin oxidase. The glycated hemoglobin is capable of reacting with various genotypes and enables highly accurate measurement of glycated hemoglobin in a sample containing glycated abnormal hemoglobin.

3 Claims, 15 Drawing Sheets

Specification includes a Sequence Listing.

```
Co  1   MTSNRADTRVIVVGGGGTIGSSTALHLVRSGYAPANITVLDTFEIPSAQS  50
Et  1   MAHSRASTKVVVVGGGGTIGSSTALHLIRSGYTPSNITVLDVYKTPSLQS  50
Py  1   MAASRAKTTVIVVGGGGTIGSSTALHLLRSGYTPSNITVLDTYPIPSLQS  50
Ar  1   MAASRKTTKVIVVGGGGTIGSSTALHLLRSGYTATNITVLDTYPIPSAQS  50
Cc  1   MAPSRANTSVIVVGGGGTIGSSTALHLVRSGYTPSNITVLDTYPIPSAQS  50
Nv  1   MTTPRKETTVLIIGGGGTIGSSTALHLLRAGYTPSNITVLDTYPIPSAQS  50
Cn  1   MPPSRASTKVIVIGGGGTLGSSTALHLRAGYTPSNITVLDTYLIPSAQS  50
Pn  1   MAPSRANTSVIVVGGGGTIGSSTALHLVRSGYTPSNVTVLDAYPIPSSQS  50
An  1   MTP-RANTKIIVVGGGGTMGSSTALHLLRAGYTPSNITVLDTCPIPSAQS  49
En  1   MAP-RANTKIIVVGGGGTMGSSTALHLLRAGYTPSNITVLDTYPIPSAQS  49
Ul  1   MAPNRANISVIVVGGGGTIGSSTALHLVRSGYTPSNITVLDTYPIPSAQS  50
Pj  1   MAHSRESTKIVIVGGGGTMGSSTALHLIRSGYTPSNITVLDVYPIPSLQS  50

Co  51  AGHDLNKIMGIRLRNKVDLQMSLEARQMWKEDELFQPFFHNTGRMDCEHT  100
Et  51  AGHDLNKIMGIRLRNGPDLQLSLESLDMWQNDELFKPFFHQVGMIDCSSS  100
Py  51  AGNDLNKIMGIRLRNKVDLQLSLEAREMWREDELFRDFFHNTGRLDCAHG  100
Ar  51  AGNDLNKIMGIRLRNPVDKQLSLEAQDMWCHDELFKPYFHNTGRMDCEGT  100
Cc  51  AGNDLNKIMGIRLRNKVDLQLSLEARQMWREDDLFKEYFHNTGRLDCAHG  100
Nv  51  AGNDLNKIMGIRLRNKVDLQLSLEARDMWRNDALFRPFFHNTGRLDCESS  100
Cn  51  AGNDLNKIMGIRIRNPVDKQLSLEARDMWREDEVFKPYFHNTGRLDCAHT  100
Pn  51  AGNDLNKIMGVSLRNPVDLQLALEARQMWNEDELFKKFFHNTGRLDCAHG  100
An  50  AGYDLNKIMSIRLRNKPDLQLSLEALDMWKNDPLFKPFFHNVGMIDVSST  99
En  50  AGYDLNKIFGIRLRNKPDLQLYLEALDMWKNDPLFKPFFHNVGQMDVSST  99
Ul  51  AGNDLNKIMGIRLRNKVDLQLSLEARQMWTEDDLFKEYFHKTGRLDCAHG  100
Pj  51  AGYDLNKIMSIRLRNGPDLQLSLEALDMWKNDPLFKPFFHNVGMLDCSSS  100
```

(56) References Cited

U.S. PATENT DOCUMENTS

| | | |
|---|---|---|
| 7,070,948 B1 | 7/2006 | Sakaue et al. |
| 2003/0157593 A1 | 8/2003 | Kurosawa et al. |
| 2007/0054344 A1 | 3/2007 | Ebinuma |
| 2008/0113381 A1 | 5/2008 | Matsuoka et al. |
| 2008/0233605 A1 | 9/2008 | Taniguchi et al. |
| 2011/0195444 A1 | 8/2011 | Hirao et al. |
| 2012/0003678 A1 | 1/2012 | Aisaka et al. |
| 2013/0267007 A1 | 10/2013 | Ichiyanagi et al. |
| 2015/0118700 A1 | 4/2015 | Ichiyanagi et al. |
| 2016/0123999 A1 | 5/2016 | Ogawa et al. |
| 2016/0251695 A1 | 9/2016 | Masakari et al. |
| 2016/0274129 A1 | 9/2016 | Ichiyanagi |
| 2018/0371429 A1 | 12/2018 | Ichiyanagi et al. |

FOREIGN PATENT DOCUMENTS

| | | | |
|---|---|---|---|
| JP | 2001-095598 A | | 4/2001 |
| JP | 2003-235585 A | | 8/2003 |
| JP | 2004-275013 A | | 10/2004 |
| JP | 2004-275063 A | | 10/2004 |
| JP | 2010-035469 A | | 2/2010 |
| JP | 2010-057474 A | | 3/2010 |
| JP | 2011-229526 A | | 11/2011 |
| WO | WO 97/13872 A1 | | 4/1997 |
| WO | WO 2004/038034 A1 | | 5/2004 |
| WO | WO 2004/104203 A1 | | 12/2004 |
| WO | WO 2005/049857 A1 | | 6/2005 |
| WO | WO 2008/108385 A1 | | 9/2008 |
| WO | WO 2010/041419 A1 | | 4/2010 |
| WO | WO 2010/041715 A1 | | 4/2010 |
| WO | WO 2011/015325 A1 | | 2/2011 |
| WO | WO 2012/018094 A1 | | 2/2012 |
| WO | WO 2013/162035 A1 | | 10/2013 |
| WO | WO 2015/005257 A1 | | 1/2015 |
| WO | WO 2015/060429 | * | 4/2015 |
| WO | WO 2015/060429 A1 | | 4/2015 |
| WO | WO 2015/060431 A1 | | 4/2015 |
| WO | WO 2016/159384 A1 | | 10/2016 |

OTHER PUBLICATIONS

Hirokawa et al., Biotechnol. Lett. 27: 963-968 (2005).*
Jaisson et al., Clin. Chim. Acta 434: 48-52 (2014).*
Kikkoman, https://biochemifa.kikkoman.com/e/products/detail/?id=13100, accessed Oct. 6, 2022.*
Radin, J. Gen. Intern. Med. 29(2): 388-394 (2013).*
International Search Report dated Nov. 20, 2018 in PCT/JP2018/032389.

Collard et al., "Crystal Structure of the Deglycating Enzyme Fructosamine Oxidase (Amadoriase II)," The Journal of Biological Chemistry, Oct. 3, 2008, 283(40):27007-27016.
Ferri et al., "Cloning and Expression of Fructosyl-amine Oxidase from Marine Yeast *Pichia* Species N1-1," Mar. Biotechnol., 2004, 6:625-632.
Ferri et al., "Isolation and characterization of a fructosyl-amine oxidase from an *Arthrobacter* sp.," Biotechnology Letters, 2005, 27:27-32.
Fujiwara et al., "Alteration of Substrate Specificity of Fructosyl-Amino Acid Oxidase from *Ulocladium* sp. JS-103," Journal of Bioscience and Bioengineering, 2006, 102(3):241-243.
Fujiwara et al., "Alteration of substrate specificity of fructosyl-amino acid oxidase from *Fusarium oxysporum*," Appl. Microbiol. Biotechnol., 2007, 74:813-819.
Hirokawa et al., "Molecular cloning and expression of novel fructosyl peptide oxidases and their application for the measurement of glycated protein," Biochemical and Biophysical Research Communications, 2003, 311:104-111.
Hirokawa et al., "Recombinant *Agrobacterium* AgaE-like Protein with Fructosyl Amino Acid Oxidase Activity," Biosci. Biotechnol. Biochem., 2002, 66(11):2323-2329.
Jeppsson et al., "Approved IFCC Reference Method for the Measurement of $HbA_{1c}$ in Human Blood," Clin. Chem. Lab. Med., 2002, 40(1):78-89.
Kim et al., "Motif-Based Search for a Novel Fructosyl Peptide Oxidase from Genome Databases," Biotechnology and Bioengineering, Jun. 15, 2010, 106(3):358-366.
Rigoldi et al., "Crystal structure of the deglycating enzyme Amadoriase I in its free form and substrate-bound complex," Proteins, 2016, 84:744-758.
Sakaue et al., "Cloning and Expression of Fructosyl-amino Acid Oxidase Gene from *Corynebacterium* sp. 2-4-1 in *Escherichia coli*," Biosci. Biotechnol. Biochem., 2002, 66(6):1256-1261.
Yoshida et al., "Primary structures of fungal fructosyl amino acid oxidases and their application to the measurement of glycated proteins," Eur. J. Biochem., 1996, 242:499-505.
Bry et al., "Effects of Hemoglobin Variants and Chemically Modified Derivatives on Assays for Glycohemoglobin," Clinical Chemistry, 2001, 47(2):153-163.
Little et al., "HbA1c: How do we measure it and what does it mean?", Current Opinion in Endocrinology, Diabetes & Obesity, 2009, 16:113-118.
Mongia et al., "Effects of Hemoglobin C and S Traits on the Results of 14 Commercial Glycated Hemoglobin Assays," Am. J. Clin. Pathol., 2008, 130:136-140.
Sacks, David B., "A1C Versus Glucose Testing: A Comparison," Diabetes Care, Feb. 2011, 34:518-523.

* cited by examiner

```
Co  399  EEMAYQWRWRPG-GDALKSRRAAPPAKDLADMPGWKHDPKL---------               437
Et  399  QEMAGAWRWRPG-GDALKSRRGAAPPAKDLAEMPGWKHDAHL----------              437
Py  397  ADLAHAWRWRPGQGDALRSRRAAAPPAKDLADMPGWNHD-ESPRAKL------             440
Ar  400  DDLAQAWRWRPGQGDALKSRRAAAPPAKDLADMPGWNHD-DSGNATSGTSSE-             449
Cc  397  EDLAESWRWRPGSGDALKKSRRAAAPPAKDLADLPGWNHD-QDSVKSKL----             440
Nv  399  DDLAEAWRWRPGSGDALLR-RRSAAPPAKDLADMPGWNHD-DVKSR-------             441
Cn  399  DDLAHAWRWRPGSGDALLKKSRRAAAPPAKDLADMPGWNHDEPSDDMDVKDVA             448
Pn  395  SVFKDAWRWRPGTGDALLR-RRAAAPPARDLADMPGWNHD-QDSESR------             437
An  399  DVFKDAWRWRPGSGDALPL-RRAAAPPAKDLADMPGWNHD--AKM-KPRANL-             438
En  399  DDLAHAWRWRPGSGDALKKSRRAAAPPAKDLADMPGWRNEAKM----------             438
Ui  397  SV---AWRWRPGTGDALLKKSRRAAAPPAKDLADMPGWRNHDGEAPRAKL---             441
Pj  399  QDLAGAWRWRPG-GDALKSSRSAAPPAKDLAEMPGWKHDAKL-----------             437
```

| Label | Position | Seq. ID |
|---|---|---|
| Co | 437 | (Seq. ID No:1) |
| Et | 437 | (Seq. ID No:3) |
| Py | 440 | (Seq. ID No:4) |
| Ar | 452 | (Seq. ID No:5) HKL |
| Cc | 440 | (Seq. ID No:6) |
| Nv | 441 | (Seq. ID No:7) VSLASVKIGENIGEKVVEDGARVGVKVLA |
| Cn | 477 | (Seq. ID No:8) |
| Pn | 437 | (Seq. ID No:9) |
| An | 438 | (Seq. ID No:10) |
| En | 438 | (Seq. ID No:11) |
| Ui | 441 | (Seq. ID No:12) |
| Pj | 437 | (Seq. ID No:13) |

| | | | | | | | | | |
|---|---|---|---|---|---|---|---|---|---|
|Co|92|TGRMDCEHTPEGIEDLKKQYQALHDAGAGLEKTHAWLDNEDEILSKMPLL|141|
|Et|92|VGMIDDCSSSKEGIENLRRKYQTLLDDAGIGLEKTNVVWLESEDEILAKAPNF|141|
|Py|92|TGGRRDDCAHGEEKGINDLRQAYQTLLDANAGLEKTNEWLDSEDEILAKMPLL|141|
|Ar|92|TGGRMDDCEGTEKGIAALKRQAYQTLLDADVGLEETTEWLDSEDAILAKMPLL|141|
|Cc|92|TGGRLDDCESSAEGVEGLRRKSYEALVEAGVGLEETHEWLDSEDEILLEKAPLL|141|
|Nv|92|TGGRLDDCAHTPESIASLRRKSGYQALKLAGSGLEETHHWLSTEDEILARAPLL|141|
|Cn|92|TGGRLDDCAHGEEKDIADLKKRRMRYQSLLDDAGIGLEKTNEWLDSEDEILLKRMPLL|139|
|Pn|92|VGMIDDVSSTEEGIKKLRMRYQAYQSLLDDAGIGLDATNFMLESEDEILAKAPHF|140|
|An|91|VGGQMDDCAHGSSSQEGIASLRRKHQDLIDANAGLEKTNFLLESEDKILAKAPHF|140|
|En|91|TGGRLDDCSSSACSSAGLDRLG-RVRKHQDLIDANIGLEKTNIWLESEDDILAKAPHF|141|
|Uj|92|VGMLDDCSSSACSQEGIASLGLDRLG-RVRVRPEHFQFRQLAPA-VLK|141|
|Pj|92|TGGVLLMSAGSTTQEGIASLGLDRLERLG.VRVRPGEDPN-LVELTRPEQFRKLAPEG-VLK|139|
|Ao2|94|TGGVVMSATTQEGTPKS-IKQLVEDE-GDDIDA-DVAELTRPNTAEDFRKTMPEG-ILT|140|
|Af2|94|TGGSVVAGSGHTASLIKH-IQEH-EDSSDA-QYTPLNTAEDFRKTMPPG-ILT|139|
|At|94|TGGAILSGHTPAL-IDH-IRKDEDE-DSSDA-EFIKLNTAEDFRRTMPPGVLT|143|
|Fo|97|TGAILSGHTPAL-IDH-IRKDE-VEPSET-NFVKLETAEDFRRTMPPGVLT|145|
|Ao1|99|VGFIALASSDALLHDKEYYEELQKNGLRNYRY-ISTPEEFREYLPI--LK|145|
|Af1|99|TGIIYAATGKEQRESIDYREYLLGRK-DKVVKLNSVEDYEKYVPNKEGS|135|
|Pi|88| | |134|
|Dh|86| | | |

Fig. 2-4

| | | | | | | | | |
|---|---|---|---|---|---|---|---|---|
| Co | 142 | QRDQIQG---- | WKAIWSQDG- | GWL | AAA | KAI | NAI | GQFLKERGVKFFGFGGAGSF | 188 |
| Et | 142 | TREQVKG---- | WKGLFCTDG- | GWL | AAA | KAI | NAI | G--FLQDRGVKFFGFGGAGSF | 188 |
| Py | 142 | SREQIKG---- | WKAVFSRDG- | GWL | AAA | GKA | INA | GEYLRKERGVNFFGFGGAGAF | 188 |
| Ar | 142 | ERDQIKG---- | WKAIFSQDG- | GWL | AAA | KAI | INA | GEYLRRAQGVKFFGFGGAGSF | 188 |
| Cc | 142 | DREQIKG---- | WKAVYSQDG- | GWL | AAA | KAI | INA | GEELRQRQGVRFFGFGGAGSF | 188 |
| Nv | 142 | QREEIEG---- | WKAIWSEDG- | GWL | AAA | KAI | NSI | GQVLKERDQGVKFFGFGGAGSF | 188 |
| Cn | 142 | DRKQIKG---- | WKAIYSEDG- | GWL | AAA | KAI | NAI | GVGEYLRDKEGVRFFGFGGAGSF | 186 |
| Pn | 140 | SRDQIKG---- | WKAIFSKDG- | GWL | AAA | KAI | NAI | GQFLKERDQGVKFFGFGGAGSF | 187 |
| An | 141 | TQEQIKG---- | WKGLFCGDG- | GWL | AAA | KAI | --- | GQRFLKSQGVKFFGFGGAGSF | 187 |
| En | 141 | TREQIKG---- | WKGLFCGDG- | GWL | AAA | KAI | --- | GT-IREAEKLGVKFFGFGGAGSF | 188 |
| Ui | 142 | NRDQIKG---- | WKAVFSEDG- | GWL | AHA | KNA | AAA | AREAQRMGVRFFVTG-TQGR | 184 |
| Pj | 142 | TREQIKG---- | WKGLFCGDG- | GWL | AHA | RNA | LVA | ARREARLGVKFFVTGTPQGR | 186 |
| Ao2 | 140 | GNFPG----- | WKRGYHIRSN | AGWA | HAR | RNA | LVA | AAAREFEESERLGVRFFVAGSPQGR | 185 |
| Af2 | 141 | GDFPG----- | WKGYFARSGA | GWA | HAK | KAM | KAA | FEESAYTEAKRLGVKFFI--TGSPEGK | 189 |
| At | 140 | GNFPG----- | WKGYHIRSN | AGWA | HAK | KAM | FSA | YTNEAKRLGVTFFI--TGSPEGD | 191 |
| Fo | 144 | GNFPG----- | WKGFYKPTGS | GGWV | HAR | KAM | ISA | FNEAKRLGVEFFVFG-DDGE | 191 |
| Ao1 | 146 | GNFPG----- | WKGWLNKTGA | GWI | --- | HAK | KAM | ISAYEECKRLGVEFFVFG-DDGE | 180 |
| Af1 | 146 | GDFPG----- | WKGWLHKSGA | GWL | HAR | DSL | KSA | YEECKRLGVEFFVFG-DDGE | 184 |
| Pi | 136 | GPLPN----- | WRGYVLDGDN | GWL | HAR | DSL | KSA | YEECKRLGVEFFVFG-DDGE | 180 |
| Dh | 135 | KSYPNKFQKM | YGGYYQEKNC | GWA | FAR | LAL | ENC | VEECRKLGAKFFVIDSAEEL | 184 |

| | | | | | | | | | |
|---|---|---|---|---|---|---|---|---|---|
| Co | 386 | GKYVVELIEG----RLPEEMAYQWRMRPG-GDALK-------SRRAAPPKDLAD | 427 |
| Et | 386 | GKHVVELLEG----SLSQEMAGAWRMRPG-GDALR-------SRRGAPAKDLAE | 427 |
| Py | 384 | GKHVVELLEG----TLAADLAADLAHAWRMRPG-IGDALQ-------SRRAAPAKDLAD | 426 |
| Ar | 387 | GKHVVELLEG----RLADDLAQAWRMRPG-QGDALK-------SRRAPAKDLAD | 429 |
| Cc | 384 | GKHVVELLEG----TLAEDLAEDLAHAWRMRPG-TGDALK-------SRRAAPAKDLAD | 426 |
| Nv | 386 | GKHVVELVEG----RLADDLAEAWRMRPG-QGDALK-------SRRAAPAKDLAD | 428 |
| Cn | 386 | GKHVVELLEG----TLAEDLAESWRMRPG-SGDDPL-I---SRRAPAKDLAD | 428 |
| Pn | 382 | GKHVVELLEE----RLESVFKDAWRMRPG-SGDALK-------SRRAPAKDLAD | 424 |
| An | 386 | GKHVVELLEG----RLESVFKDLAHAWRMRPG-SGDALK-------SRRAAPAKDLAD | 428 |
| En | 386 | GKHVVELLEG----TLADDLAHAGAWRMRPG-TGDALK-------SRRAAPARAKDLAE | 428 |
| Ul | 384 | GKHV-------RLPQDLAGAWRMRPG-GDALK-------SKRSAPAKDLAD | 426 |
| Pj | 386 | GNL--IVDAIED----KVPEKVHKLTRWMSPD-IAVDRKKWRDTLGRFGGPNRVMD | 427 |
| Ao2 | 372 | GNL--IVDAMEG----KVPQKI-HELIKWMN-PD-AANRNWRDTLGRFGGPNRVMD | 418 |
| Af2 | 374 | GS---IADAMED----KTPAKI-HKLI-RWMS-PE-AINRNWGDRLGRFGGPNRVMD | 420 |
| At | 373 | SDCMEG----TLEERFAKYWRAL-RWMR-PE-KFTEFWGKDPLDRFGADDPNKVMD | 419 |
| Fo | 378 | GGFI--ADALEG----NLQKELKHALRWMR-PE-AAQRDWKDTQNRFGGPNKVMD | 424 |
| Ao1 | 381 | GGFI--ADALES----KLQKEVKDI-VRWMR-PE-TAVDRDWKRPETWDKRG---QVRWGGRYRVAD | 427 |
| Af1 | 381 | GKYVSKVVTKGDKG-LDPEDKECWKWMR-PE-TWDKRG---QVRWGGRYRVAD | 427 |
| Pi | 363 | GKYI-SQVALKGENSLDKDKKELWRWMR-PD-MGKKRDLKD-NEVKD | 408 |
| Dh | 363 | | 412 |

Fig. 2-10

| | | Sequence | End | SEQ ID |
|---|---|---|---|---|
| Co | 428 | MPGWKKHDPKL--------------------------------------- | 437 | (Seq. ID No:1) |
| Et | 428 | MPGWKKHDAHL--------------------------------------- | 437 | (Seq. ID No:3) |
| Py | 427 | MPGWNHD-ESPRAKL----------------------------------- | 440 | (Seq. ID No:4) |
| Ar | 430 | MPGWNHDGDSGNATSGTSSEHKL--------------------------- | 452 | (Seq. ID No:5) |
| Cc | 427 | MPGWKHD-DVVKSKL----------------------------------- | 440 | (Seq. ID No:6) |
| Nv | 429 | MPGWKHDQDSESR------------------------------------- | 441 | (Seq. ID No:7) |
| Cn | 429 | LPGWNHDEPSDDDDMDVKDVAVSLASVKIGENIGEKVVEDGARVGVKVLA | 477 | (Seq. ID No:8) |
| Pn | 425 | MPGWNHD-KPRANL------------------------------------ | 437 | (Seq. ID No:9) |
| An | 429 | MPGWRNEAKM---------------------------------------- | 438 | (Seq. ID No:10) |
| En | 429 | MPGWRNEAKM---------------------------------------- | 438 | (Seq. ID No:11) |
| Ul | 427 | MPGWNHDGEAPRAKL----------------------------------- | 441 | (Seq. ID No:12) |
| Pj | 428 | MPGWKHDAKL---------------------------------------- | 437 | (Seq. ID No:13) |
| Ao2 | 419 | FH--DVKEWTNVQNKDTAKL----------------------------- | 436 | (Seq. ID No:14) |
| Af2 | 421 | FH--DVKEWTNVQYRDISKL----------------------------- | 438 | (Seq. ID No:15) |
| At | 420 | FN--EVKEWTNVTQRDISKL----------------------------- | 437 | (Seq. ID No:16) |
| Fo | 425 | LPKSDVEGWTNIKNDI--------------------------------- | 440 | (Seq. ID No:17) |
| Ao1 | 428 | FQKVGENEWTKIGDKSRL------------------------------- | 445 | (Seq. ID No:18) |
| Af1 | 428 | FQQVGEDQWTKIGESRGP------------------------------- | 445 | (Seq. ID No:19) |
| Pi | 409 | LN--IEEEWVSVENPTPHKLE---------------------------- | 427 | (Seq. ID No:20) |
| Dh | 413 | LK--NVKQWSNGKSHL--------------------------------- | 426 | (Seq. ID No:21) | ically measuring HbA1c with

SEQUENCE LISTING

<160> NUMBER OF SEQ ID NOS: 66

<210> SEQ ID NO 1
<211> LENGTH: 437
<212> TYPE: PRT
<213> ORGANISM: Coniochaeta sp.

<400> SEQUENCE: 1

Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
                20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Arg Leu Arg
        50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Asp Leu Lys Lys Gln Tyr Gln
                100                 105                 110

Ala Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
        130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
        370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
                420                 425                 430

His Asp Pro Lys Leu
        435

<210> SEQ ID NO 2
<211> LENGTH: 1314
<212> TYPE: DNA
<213> ORGANISM: Coniochaeta sp.

<400> SEQUENCE: 2

```
atgacgtcga atcgtgcaga tacaagggtg attgtcgtcg gtggcggagg aacgattggt       60
tcctcgacag cgctgcatct tgtgaggagt ggttatgctc ccgcaaatat cacggtcttg      120
gacacatttg agattccatc ggctcaatca gccggccatg atctcaacaa gatcatggga      180
atacgactgc gcaacaaggt ggacctgcaa atgagtctag aggctagaca gatgtggaag      240
gaggatgagt tattccagcc cttctttcac aataccggca gaatggactg cgaacacacg      300
cctgagggta tcgaggacct gaaaaagcag taccaggcac tgcacgatgc cggtgcgggt      360
ctggagaaga ctcatgcctg gttggacaac gaggatgaga tcttatccaa gatgccgttg      420
cttcaacgtg accaaataca aggatggaaa gcaatatgga gtcaagatgg cggctggtta      480
gctgcggcaa aggccatcaa tgcgatcgga cagttcttga agaacgtggt gtaaagttc       540
ggattcggcg cgctggatc cttcaagcaa cccctttcg acgatgaagg cacaacttgc        600
attggcgttg agacggcaga tggtaccaaa tattacgctg acaaggtggt cttagcagct      660
ggcgcatgga gcccaaccct ggtggacctg aagatcaat gttgctcgaa ggcttgggtg       720
tatgctcata ttcagttgac gcctgaagag gccgctgagt ataagggtgt cccagttgtg      780
tataatggcg aatttggctt cttctttgag cctgatgagt ttggtgtaat aaaggtgtgc      840
gacgagttcc caggattctc gcgcttcaag gaacatcaac cctatggcgc cccatctccg      900
aaacggatat cagtaccacg atcgcacgcc aagcatccca cagacactta tccagacgca      960
tccgaagtca gcatcaaaaa agcaatcgcg acgtttctcc ctcgatttca ggacaaggag     1020
ctcttcaatc gcgccttgtg ctggtgtaca gacactgcgg acgctgctct cttgatgtgt     1080
gaacacccca atggaagaa tttcattcta gcgaccggcg acagcggaca ctcattcaaa     1140
atcttgccta acgtcggaaa atacgtagtc gagttgatag agggccgcct gccggaggaa     1200
atggcttatc aatggaggtg gcggccagga ggcgatgcac tcaagtctag acgtgcggca     1260
ccgccaaaag atcttgcaga catgccagga tggaaacatg atccgaaatt gtaa           1314
```

<210> SEQ ID NO 3
<211> LENGTH: 437
<212> TYPE: PRT
<213> ORGANISM: Eupenicillium terrenum

<400> SEQUENCE: 3

Met Ala His Ser Arg Ala Ser Thr Lys Val Val Val Gly Gly Gly
1                 5                 10                  15

Gly Thr Ile Gly Ser Ser Thr Ala Leu His Leu Ile Arg Ser Gly Tyr

```
            20                  25                  30
Thr Pro Ser Asn Ile Thr Val Leu Asp Val Tyr Lys Thr Pro Ser Leu
            35                  40                  45
Gln Ser Ala Gly His Asp Leu Asn Lys Ile Met Gly Ile Arg Leu Arg
            50                  55                  60
Asn Gly Pro Asp Leu Gln Leu Ser Leu Glu Ser Leu Asp Met Trp Gln
 65                  70                  75                  80
Asn Asp Glu Leu Phe Lys Pro Phe His Gln Val Gly Met Ile Asp
                    85                  90                  95
Cys Ser Ser Lys Glu Gly Ile Glu Asn Leu Arg Arg Lys Tyr Gln
                100                 105                 110
Thr Leu Leu Asp Ala Gly Ile Gly Leu Glu Lys Thr Asn Val Trp Leu
            115                 120                 125
Glu Ser Glu Asp Glu Ile Leu Ala Lys Ala Pro Asn Phe Thr Arg Glu
            130                 135                 140
Gln Val Lys Gly Trp Lys Gly Leu Phe Cys Thr Asp Gly Gly Trp Leu
145                 150                 155                 160
Ala Ala Ala Lys Ala Ile Asn Ala Ile Gly Ile Phe Leu Gln Asp Lys
                165                 170                 175
Gly Val Lys Phe Gly Phe Gly Ala Gly Thr Phe Gln Gln Pro Leu
            180                 185                 190
Phe Ala Ala Asp Gly Lys Thr Cys Ile Gly Leu Glu Thr Thr Asp Gly
            195                 200                 205
Thr Lys Tyr Phe Ala Asp Lys Val Val Leu Ala Ala Gly Ala Trp Ser
            210                 215                 220
Pro Thr Leu Val Asp Leu Glu Asp Gln Cys Val Ser Lys Ala Trp Val
225                 230                 235                 240
Phe Ala His Ile Gln Leu Thr Pro Lys Glu Ala Asp Ala Tyr Lys Asn
                245                 250                 255
Val Pro Val Val Tyr Asp Gly Glu Tyr Gly Phe Phe Phe Glu Pro Asn
            260                 265                 270
Glu Tyr Gly Val Ile Lys Val Cys Asp Glu Phe Pro Gly Phe Ser Arg
            275                 280                 285
Phe Lys Leu His Gln Pro Tyr Gly Ala Ala Ser Pro Lys Met Ile Ser
            290                 295                 300
Val Pro Arg Ser His Ala Lys His Pro Thr Asp Thr Tyr Pro Asp Ala
305                 310                 315                 320
Ser Glu Val Thr Ile Arg Lys Ala Ile Ala Arg Phe Leu Pro Glu Phe
                325                 330                 335
Lys Asp Lys Glu Leu Phe Asn Arg Thr Met Cys Trp Cys Thr Asp Thr
                340                 345                 350
Ala Asp Ala Asn Leu Leu Ile Cys Glu His Pro Lys Trp Lys Asn Phe
            355                 360                 365
Ile Leu Ala Thr Gly Asp Ser Gly His Ser Phe Lys Leu Leu Pro Asn
            370                 375                 380
Ile Gly Lys His Val Val Glu Leu Leu Glu Gly Ser Leu Ser Gln Glu
385                 390                 395                 400
Met Ala Gly Ala Trp Arg Trp Arg Pro Gly Asp Ala Leu Arg Ser
                405                 410                 415
Arg Arg Gly Ala Pro Ala Lys Asp Leu Ala Glu Met Pro Gly Trp Lys
            420                 425                 430
His Asp Ala His Leu
            435
```

<210> SEQ ID NO 4
<211> LENGTH: 440
<212> TYPE: PRT
<213> ORGANISM: Pyrenochaeta sp.

<400> SEQUENCE: 4

```
Met Ala Ala Ser Arg Ala Lys Thr Thr Val Ile Val Gly Gly Gly
1               5                   10                  15

Gly Thr Ile Gly Ser Ser Thr Ala Leu His Leu Leu Arg Ser Gly Tyr
                20                  25                  30

Thr Pro Ser Asn Ile Thr Val Leu Asp Thr Tyr Pro Ile Pro Ser Leu
            35                  40                  45

Gln Ser Ala Gly Asn Asp Leu Asn Lys Ile Met Gly Ile Arg Leu Arg
        50                  55                  60

Asn Lys Val Asp Leu Gln Leu Ser Leu Glu Ala Arg Glu Met Trp Arg
65                  70                  75                  80

Glu Asp Glu Leu Phe Arg Asp Phe Phe His Asn Thr Gly Arg Leu Asp
                85                  90                  95

Cys Ala His Gly Glu Lys Gly Ile Asn Asp Leu Arg Gln Ala Tyr Gln
            100                 105                 110

Thr Leu Leu Asp Ala Asn Ala Gly Leu Glu Glu Thr Asn Glu Trp Leu
        115                 120                 125

Asp Ser Glu Asp Glu Ile Leu Ala Arg Met Pro Leu Leu Ser Arg Glu
130                 135                 140

Gln Ile Lys Gly Trp Lys Ala Val Phe Ser Arg Asp Gly Gly Trp Leu
145                 150                 155                 160

Ala Ala Gly Lys Ala Ile Asn Ala Ile Gly Glu Tyr Leu Arg Lys Glu
                165                 170                 175

Gly Val Lys Phe Gly Phe Gly Ala Gly Ser Phe Gln Gln Pro Leu
            180                 185                 190

Leu Ala Glu Gly Ile Cys Ile Gly Val Glu Thr Thr Asp Gly Thr Arg
        195                 200                 205

Tyr Tyr Ala Asp Lys Val Val Leu Ala Ala Gly Ala Trp Ser Pro Ala
210                 215                 220

Leu Val Asp Leu Glu Asp Gln Cys Val Ser Lys Ala Trp Val Tyr Ala
225                 230                 235                 240

His Met Gln Leu Thr Pro Lys Glu Ala Ala Tyr Lys Asp Thr Pro
                245                 250                 255

Val Val Tyr Asn Gly Asp Leu Gly Phe Phe Phe Glu Pro Asn Glu His
            260                 265                 270

Gly Val Ile Lys Val Cys Asp Glu Phe Pro Gly Phe Thr Arg Phe Lys
        275                 280                 285

Lys His Gln Pro Phe Gly Ala Arg Ala Pro Lys Arg Ile Ser Val Pro
290                 295                 300

Arg Ser His Ala Lys His Pro Thr Asp Thr Tyr Pro His Ala Ser Glu
305                 310                 315                 320

Ala Ser Ile Lys Lys Ala Ile Ala Phe Leu Pro Gln Phe Lys Asp
                325                 330                 335

Lys Glu Leu Phe Asn Arg Ala Met Cys Trp Cys Thr Asp Thr Ala Asp
            340                 345                 350

Ala Ala Leu Leu Ile Cys Glu His Pro Gln Trp Lys Asn Phe Met Leu
        355                 360                 365

Ala Thr Gly Asp Ser Gly His Ser Phe Lys Leu Leu Pro Asn Ile Gly
```

```
                370                 375                 380
Lys His Val Val Glu Leu Ile Glu Gly Thr Leu Ala Ala Asp Leu Ala
385                 390                 395                 400

His Ala Trp Arg Trp Arg Pro Gly Ile Gly Asp Ala Leu Gln Ser Arg
                405                 410                 415

Arg Ala Ala Pro Ala Lys Asp Leu Ala Asp Met Pro Gly Trp Asn His
                420                 425                 430

Asp Glu Ser Pro Arg Ala Lys Leu
                435                 440

<210> SEQ ID NO 5
<211> LENGTH: 452
<212> TYPE: PRT
<213> ORGANISM: Arthrinium sp.

<400> SEQUENCE: 5

Met Ala Ala Ser Arg Lys Thr Thr Lys Val Ile Val Val Gly Gly Gly
1               5                   10                  15

Gly Thr Ile Gly Ser Ser Thr Ala Leu His Leu Leu Arg Ser Gly Tyr
                20                  25                  30

Thr Ala Thr Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
50                  55                  60

Asn Pro Val Asp Lys Gln Leu Ser Leu Glu Ala Gln Asp Met Trp Cys
65                  70                  75                  80

His Asp Glu Leu Phe Lys Pro Tyr Phe His Asn Thr Gly Arg Met Asp
                85                  90                  95

Cys Glu Gly Thr Glu Lys Gly Ile Ala Ala Leu Lys Gln Gln Tyr Gln
            100                 105                 110

Thr Leu Leu Asp Ala Asp Val Gly Leu Glu Lys Thr Thr Glu Trp Leu
        115                 120                 125

Asp Ser Glu Asp Ala Ile Leu Ala Lys Met Pro Leu Leu Glu Arg Asp
130                 135                 140

Gln Ile Lys Gly Trp Lys Ala Ile Phe Ser Asp Gly Gly Trp Leu
145                 150                 155                 160

Ala Ala Ala Lys Ala Ile Asn Ala Ile Gly Glu Glu Leu Lys Arg Gln
                165                 170                 175

Gly Val Asn Phe Gly Phe Gly Ala Gly Ala Phe Lys Lys Pro Leu
                180                 185                 190

Phe Ala Pro Asp Gly Ser Thr Cys Ile Gly Val Glu Thr Val Asp Gly
        195                 200                 205

Thr Lys Tyr Tyr Gly Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro His Glu Ala Ala Glu Tyr Gln Gly
                245                 250                 255

Cys Pro Val Val Tyr His Gly Asp Leu Gly Phe Phe Phe Glu Pro Asn
            260                 265                 270

Glu His Gly Val Ile Lys Val Cys Asp Glu Phe Pro Gly Phe Thr Arg
        275                 280                 285

Phe Leu Glu Gln His Gln Ser Tyr Gly Ala Pro Ala Pro Thr Arg Val
    290                 295                 300
```

-continued

```
Ser Val Pro Arg Ser His Ala Lys His Pro Thr Asp Thr Tyr Pro Asp
305                 310                 315                 320

Ala Ser Glu Gln Ser Ile Arg Arg Ala Val Ala Ala Phe Leu Pro Arg
            325                 330                 335

Phe Gln Ser Lys Glu Leu Phe Asn Arg Ala Met Cys Trp Cys Thr Asp
            340                 345                 350

Thr Ala Asp Ala Ala Leu Leu Ile Cys Glu His Pro Arg Trp Arg Asn
            355                 360                 365

Phe Ile Leu Ala Thr Gly Asp Ser Gly His Ser Phe Lys Leu Leu Pro
            370                 375                 380

Asn Ile Gly Lys His Val Val Glu Leu Leu Glu Gly Arg Leu Ala Asp
385                 390                 395                 400

Asp Leu Ala Gln Ala Trp Arg Trp Arg Pro Gly Gln Gly Asp Ala Leu
            405                 410                 415

Lys Ser Arg Arg Ala Ala Pro Ala Lys Asp Leu Ala Asp Met Pro Gly
            420                 425                 430

Trp Asn His Asp Gly Asp Ser Gly Asn Ala Thr Ser Gly Thr Ser Ser
            435                 440                 445

Glu His Lys Leu
    450
```

<210> SEQ ID NO 6
<211> LENGTH: 440
<212> TYPE: PRT
<213> ORGANISM: Curvularia clavata

<400> SEQUENCE: 6

```
Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
        50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Asp Leu Arg Gln Ala Tyr Gln
            100                 105                 110

Ala Leu Leu Asp Ala Asn Ala Gly Leu Glu Glu Thr Thr Glu Trp Leu
        115                 120                 125

Asp Ser Glu Asp Glu Ile Leu Lys Lys Met Pro Leu Leu Asp Arg Glu
130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Gly Ala Gly Ser Phe Lys Gln Pro Leu
            180                 185                 190

Leu Ala Glu Gly Val Cys Ile Gly Val Glu Thr Val Asp Gly Thr Arg
        195                 200                 205

Tyr Tyr Ala Asp Lys Val Val Leu Ala Ala Gly Ala Trp Ser Pro Val
    210                 215                 220
```

```
Leu Val Asp Leu Glu Asp Gln Cys Val Ser Lys Ala Trp Val Tyr Ala
225                 230                 235                 240

His Ile Gln Leu Thr Pro Glu Glu Ala Ala Glu Tyr Lys Asn Val Pro
            245                 250                 255

Val Val Tyr Asn Gly Asp Val Gly Phe Phe Glu Pro Asp Glu His
        260                 265                 270

Gly Val Ile Lys Val Cys Asp Glu Phe Pro Gly Phe Thr Arg Phe Lys
            275                 280                 285

Gln His Gln Pro Tyr Gly Ala Lys Ala Pro Lys Arg Ile Ser Val Pro
        290                 295                 300

Arg Ser Ala Ala Lys His Pro Thr Asp Thr Tyr Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
            340                 345                 350

Ala Ala Leu Leu Met Cys Glu His Pro Glu Trp Lys Asn Phe Val Leu
            355                 360                 365

Ala Thr Gly Asp Ser Gly His Thr Phe Lys Leu Leu Pro Asn Ile Gly
370                 375                 380

Lys His Val Val Glu Leu Leu Glu Gly Thr Leu Ala Glu Asp Leu Ala
385                 390                 395                 400

His Ala Trp Arg Trp Arg Pro Gly Thr Gly Asp Ala Leu Lys Ser Arg
                405                 410                 415

Arg Ala Ala Pro Ala Lys Asp Leu Ala Asp Met Pro Gly Trp Lys His
                420                 425                 430

Asp Asp Val Val Lys Ser Lys Leu
            435                 440

<210> SEQ ID NO 7
<211> LENGTH: 441
<212> TYPE: PRT
<213> ORGANISM: Neocosmospora vasinfecta

<400> SEQUENCE: 7

Met Thr Thr Pro Arg Lys Glu Thr Thr Val Leu Ile Ile Gly Gly Gly
1               5                   10                  15

Gly Thr Ile Gly Ser Ser Thr Ala Leu His Leu Leu Arg Ala Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe Phe His Asn Thr Gly Arg Leu Asp
                85                  90                  95

Cys Glu Ser Ser Ala Glu Gly Val Glu Gly Leu Arg Arg Glu Tyr Gln
            100                 105                 110

Lys Leu Val Glu Ala Gly Val Gly Leu Glu Glu Thr His Glu Trp Leu
        115                 120                 125

Asp Ser Glu Glu Ala Ile Leu Glu Lys Ala Pro Leu Leu Gln Arg Glu
    130                 135                 140

Glu Ile Glu Gly Trp Lys Ala Ile Trp Ser Glu Glu Gly Gly Trp Leu
```

```
            145                 150                 155                 160
        Ala Ala Ala Lys Ala Ile Asn Ala Ile Gly Glu Glu Leu Gln Arg Gln
                        165                 170                 175

Gly Val Arg Phe Gly Phe Gly Ala Gly Ser Phe Lys Arg Pro Leu
                        180                 185                 190

Phe Ala Asp Asp Gly Thr Thr Cys Ile Gly Val Glu Thr Val Asp Gly
                        195                 200                 205

Thr Gln Tyr His Ala Asp Lys Val Val Leu Ala Gly Ala Trp Ser
                        210                 215                 220

Pro Ala Leu Val Asp Leu Glu Glu Gln Cys Cys Ser Lys Ala Trp Val
        225                 230                 235                 240

Tyr Ala His Met Gln Leu Thr Pro Glu Glu Ala Ala Val Tyr Lys Gly
                        245                 250                 255

Cys Pro Val Val Tyr His Gly Asp Val Gly Phe Phe Glu Pro Asn
                        260                 265                 270

Glu Asn Gly Val Ile Lys Val Cys Asp Glu Phe Pro Gly Phe Thr Arg
                        275                 280                 285

Phe Lys Gln His Gln Pro Tyr Gly Ala Pro Ala Pro Lys Pro Val Ser
                        290                 295                 300

Val Pro Arg Ser His Ala Lys His Pro Thr Asp Thr Tyr Pro Asp Ala
        305                 310                 315                 320

Ser Glu Glu Ser Ile Lys Arg Ala Val Ser Thr Phe Leu Pro Arg Phe
                        325                 330                 335

Lys Asp Lys Pro Leu Phe Asn Arg Ala Leu Cys Trp Cys Thr Asp Thr
                        340                 345                 350

Ala Asp Ser Ala Leu Leu Ile Cys Glu His Pro Arg Trp Lys Asn Phe
                        355                 360                 365

Ile Leu Ala Thr Gly Asp Ser Gly His Ser Phe Lys Leu Leu Pro Ile
                        370                 375                 380

Ile Gly Lys His Val Val Glu Leu Val Glu Gly Arg Leu Ala Asp Asp
        385                 390                 395                 400

Leu Ala Glu Ala Trp Arg Trp Arg Pro Gly Gln Gly Asp Ala Arg Lys
                        405                 410                 415

Ser Ile Arg Ala Ala Pro Ala Lys Asp Leu Ala Asp Met Pro Gly Trp
                        420                 425                 430

Lys His Asp Gln Asp Ser Glu Ser Arg
                        435                 440

<210> SEQ ID NO 8
<211> LENGTH: 477
<212> TYPE: PRT
<213> ORGANISM: Cryptococcus neoformans

<400> SEQUENCE: 8

Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
                20                  25                  30

Thr Pro Ser Asn Ile Thr Val Leu Asp Thr Tyr Leu Ile Pro Ser Ala
                35                  40                  45

Gln Ser Ala Gly Asn Asp Leu Asn Lys Ile Met Gly Ile Arg Ile Arg
                50                  55                  60

Asn Pro Val Asp Lys Gln Leu Ser Leu Glu Ala Arg Asp Met Trp Arg
65              70                  75                  80
```

Asn Asp Glu Val Phe Lys Pro Tyr Phe His Asn Thr Gly Arg Leu Asp
                85                  90                  95

Cys Ala His Thr Pro Glu Ser Ile Ala Ser Leu Arg Lys Ser Tyr Glu
            100                 105                 110

Ala Ile Leu Lys Ala Gly Ser Gly Leu Glu Lys Thr His His Trp Leu
        115                 120                 125

Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
        195                 200                 205

Thr Gln Tyr Phe Ala Asp Lys Val Val Leu Ala Ala Gly Ala Trp Ser
    210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Glu Pro Asn
            260                 265                 270

Glu Lys Gly Val Ile Lys Val Cys Asp Glu Phe Pro Gly Phe Thr Arg
        275                 280                 285

Phe Lys Gln His Gln Pro Tyr Gly Ala Ser Ser Thr Lys His Ile Ser
    290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
            420                 425                 430

Asn His Asp Glu Pro Ser Asp Asp Met Asp Val Lys Asp Val Ala
        435                 440                 445

Val Ser Leu Ala Ser Val Lys Ile Gly Glu Asn Ile Gly Glu Lys Val
    450                 455                 460

Val Glu Asp Gly Ala Arg Val Gly Val Lys Val Leu Ala
465                 470                 475

<210> SEQ ID NO 9
<211> LENGTH: 437
<212> TYPE: PRT

<213> ORGANISM: Phaeosphaeria nodorum

<400> SEQUENCE: 9

```
Met Ala Pro Ser Arg Ala Asn Thr Ser Val Ile Val

```
Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
        435

<210> SEQ ID NO 10
<211> LENGTH: 438
<212> TYPE: PRT
<213> ORGANISM: Aspergillus nidulans

<400> SEQUENCE: 10

Met Thr Pro Arg Ala Asn Thr Lys Ile Ile Val Val Gly Gly Gly
  1               5                  10                  15

Thr Met Gly Ser Ser Thr Ala Leu His Leu Leu Arg Ala Gly Tyr Thr
                 20                  25                  30

Pro Ser Asn Ile Thr Val Leu Asp Thr Cys Pro Ile Pro Ser Ala Gln
             35                  40                  45

Ser Ala Gly Tyr Asp Leu Asn Lys Ile Met Ser Ile Arg Leu Arg Asn
 50                  55                  60

Lys Pro Asp Leu Gln Leu Ser Leu Glu Ala Leu Asp Met Trp Lys Asn
 65                  70                  75                  80

Asp Pro Leu Phe Lys Pro Phe His Asn Val Gly Met Ile Asp Val
                 85                  90                  95

Ser Ser Thr Glu Glu Gly Ile Glu Gly Leu Arg Lys Lys Tyr Gln Ser
                100                 105                 110

Leu Leu Asp Ala Gly Ile Gly Leu Glu Lys Thr Asn Phe Met Leu Glu
            115                 120                 125

Ser Glu Asp Glu Ile Leu Ala Lys Ala Pro His Phe Thr Gln Glu Gln
130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Phe Glu Pro Asn
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Ala Pro Lys Pro Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335
```

```
Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
            435

<210> SEQ ID NO 11
<211> LENGTH: 438
<212> TYPE: PRT
<213> ORGANISM: Emericella nidulans

<400> SEQUENCE: 11

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Arg Leu Arg Asn
    50                  55                  60

Lys Pro Asp Leu Gln Leu Tyr Leu Glu Ala Leu Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Lys Leu Arg Met Arg Tyr Gln Ser
            100                 105                 110

Leu Leu Asp Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
```

```
            260                 265                 270
Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435
```

<210> SEQ ID NO 12
<211> LENGTH: 441
<212> TYPE: PRT
<213> ORGANISM: Ulocladium sp.

<400> SEQUENCE: 12

```
Met Ala Pro Asn Arg Ala Asn Ile Ser Val Ile Val Gly Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Gln Met Trp Thr
65                  70                  75                  80

Glu Asp Asp Leu Phe Lys Glu Tyr Phe His Lys Thr Gly Arg Leu Asp
                85                  90                  95

Cys Ala His Gly Glu Lys Gly Leu Ala Asp Leu Lys Gln Ala Tyr Gln
            100                 105                 110

Ala Leu Leu Asp Ala Asn Ala Gly Leu Glu Ala Thr Thr Glu Trp Leu
        115                 120                 125

Asp Ser Glu Asp Lys Ile Leu Glu Lys Met Pro Leu Leu Asn Arg Asp
    130                 135                 140

Gln Ile Lys Gly Trp Lys Ala Val Phe Ser Glu Asp Gly Gly Trp Leu
145                 150                 155                 160

Ala Ala Ala Lys Ala Ile Asn Ala Ile Gly Arg Phe Leu Arg Asp Gln
                165                 170                 175

Gly Val Lys Phe Gly Phe Gly Ala Gly Ser Phe Lys Gln Pro Leu
            180                 185                 190
```

-continued

Leu Ala Glu Gly Val Cys Val Gly Val Glu Thr Val Asp Gly Thr Arg
        195                 200                 205

Tyr Tyr Ala Asp Lys Val Val Leu Ala Ala Gly Ala Trp Ser Pro Ala
        210                 215                 220

Leu Val Asp Leu Gln Asp Gln Cys Val Ser Lys Ala Trp Val Tyr Ala
225                 230                 235                 240

His Ile Gln Leu Ser Pro Ser Glu Ala Ala Glu Tyr Lys Asn Val Pro
                245                 250                 255

Val Val Tyr Asn Gly Asp Val Gly Phe Phe Glu Pro Asp Glu Tyr
        260                 265                 270

Gly Val Ile Lys Val Cys Asp Glu Phe Pro Gly Phe Thr Arg Phe Lys
        275                 280                 285

Gln His Gln Pro Phe Gly Ala Ser Ala Pro Lys Arg Ile Ser Val Pro
    290                 295                 300

Arg Ser Ala Ala Lys His Pro Thr Asp Thr Tyr Pro Asp Ala Ser Glu
305                 310                 315                 320

Val Ser Ile Arg Lys Ala Ile Ala Thr Phe Leu Pro Lys Phe Thr Glu
                325                 330                 335

Lys Glu Val Phe Asn Arg His Leu Cys Trp Cys Thr Asp Thr Ala Asp
        340                 345                 350

Ala Ala Leu Leu Met Cys Glu His Pro Glu Trp Lys Asn Phe Val Leu
    355                 360                 365

Ala Thr Gly Asp Ser Gly His Thr Phe Lys Leu Leu Pro Asn Ile Gly
        370                 375                 380

Lys His Val Val Glu Leu Leu Glu Gly Thr Leu Ala Asp Asp Leu Ala
385                 390                 395                 400

His Ala Trp Arg Trp Arg Pro Gly Thr Gly Asp Ala Leu Lys Ser Arg
                405                 410                 415

Arg Ala Ala Arg Ala Lys Asp Leu Ala Asp Met Pro Gly Trp Asn His
        420                 425                 430

Asp Gly Glu Ala Pro Arg Ala Lys Leu
        435                 440

<210> SEQ ID NO 13
<211> LENGTH: 437
<212> TYPE: PRT
<213> ORGANISM: Penicillium janthinellum

<400> SEQUENCE: 13

Met Ala His Ser Arg Glu Ser Thr Lys Ile Val Ile Val Gly Gly Gly
1               5                   10                  15

Gly Thr Met Gly Ser Ser Thr Ala Leu His Leu Ile Arg Ser Gly Tyr
                20                  25                  30

Thr Pro Ser Asn Ile Thr Val Leu Asp Val Tyr Pro Ile Pro Ser Leu
            35                  40                  45

Gln Ser Ala Gly Tyr Asp Leu Asn Lys Ile Met Ser Ile Arg Leu Arg
        50                  55                  60

Asn Gly Pro Asp Leu Gln Leu Ser Leu Glu Ala Leu Asp Met Trp Lys
65                  70                  75                  80

Asn Asp Pro Leu Phe Lys Pro Phe Phe His Asn Val Gly Met Leu Asp
                85                  90                  95

Cys Ser Ser Ser Gln Glu Gly Ile Ala Ser Leu Arg Arg Lys His Gln
            100                 105                 110

Asp Leu Ile Asp Ala Asn Ile Gly Leu Glu Lys Thr Asn Ile Trp Leu
        115                 120                 125

```
Glu Ser Glu Asp Asp Ile Leu Ala Lys Ala Pro His Phe Thr Arg Glu
    130                 135                 140

Gln Ile Lys Gly Trp Lys Gly Leu Phe Cys Gly Asp Gly Gly Trp Leu
145                 150                 155                 160

Ala Ala Ala Lys Ala Ile Asn Ala Ile Gly Thr Phe Leu Lys Ser Gln
                165                 170                 175

Gly Val Lys Phe Gly Phe Gly Ser Ala Gly Thr Phe Lys Arg Pro Leu
            180                 185                 190

Phe Ala Pro Asp Gly Ala Thr Cys Ser Gly Val Glu Thr Val Asp Gly
        195                 200                 205

Thr Lys Tyr Phe Ala Asp Lys Val Val Leu Ala Ala Gly Ala Trp Ser
    210                 215                 220

Ser Thr Leu Val Asp Leu Glu Asp Gln Cys Val Ser Lys Ala Trp Val
225                 230                 235                 240

Phe Ala His Ile Gln Leu Thr Pro Gln Glu Ser Ala Gln Tyr Lys Asp
                245                 250                 255

Val Pro Val Val Tyr Asp Gly Asp Tyr Gly Phe Phe Glu Pro Asn
            260                 265                 270

Glu His Gly Val Ile Lys Val Cys Asp Glu Phe Pro Gly Phe Ser Arg
        275                 280                 285

Phe Lys Leu His Gln Pro Tyr Gly Ala Thr Ser Pro Lys Leu Ile Ser
    290                 295                 300

Val Pro Arg Ser His Ala Lys His Pro Thr Asp Thr Tyr Pro Asp Ser
305                 310                 315                 320

Ser Glu Glu Thr Ile Arg Lys Ala Ile Ala Arg Phe Met Pro Arg Phe
                325                 330                 335

Lys Asp Lys Glu Leu Phe Asn Arg Ser Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Val Leu Pro Asn
    370                 375                 380

Ile Gly Lys His Val Val Glu Leu Ile Glu Gly Arg Leu Pro Gln Asp
385                 390                 395                 400

Leu Ala Gly Ala Trp Arg Trp Arg Pro Gly Gly Asp Ala Leu Lys Ser
                405                 410                 415

Lys Arg Ser Ala Pro Ala Lys Asp Leu Ala Glu Met Pro Gly Trp Lys
            420                 425                 430

His Asp Ala Lys Leu
        435

<210> SEQ ID NO 14
<211> LENGTH: 436
<212> TYPE: PRT
<213> ORGANISM: Aspergillus oryzae

<400> SEQUENCE: 14

Met Thr Val Ala Lys Ser Ser Ile Leu Ile Gly Ala Gly Thr
1               5                   10                  15

Trp Gly Ala Ser Thr Ala Leu His Leu Gly Arg Arg Gly Tyr Thr Asn
                20                  25                  30

Val Thr Val Leu Asp Pro Tyr Thr Val Pro Ser Ala Ile Ser Ala Gly
            35                  40                  45

Asn Asp Val Asn Lys Ile Ile Ser Ser Gly Gln Tyr Ser Asn Lys Lys
```

```
            50                  55                  60
Asp Glu Ile Glu Val Asn Glu Ile Leu Ala Glu Ala Phe Lys Gly
 65                  70                  75                  80

Trp Thr Thr Asp Pro Leu Phe Lys Pro Tyr Tyr His Asp Thr Gly Val
                 85                  90                  95

Val Met Ser Ala Cys Ser Ser Ala Gly Leu Asp Arg Leu Gly Ile Arg
                100                 105                 110

Val Arg Pro Glu Glu Pro Asp Val Ser Glu Val Thr Lys Pro Glu
            115                 120                 125

His Phe Arg Gln Leu Ala Pro Ala Val Leu Lys Gly Asn Phe Pro Gly
        130                 135                 140

Trp Arg Gly Tyr His Ile Arg Ser Asn Ala Gly Trp Ala His Ala Arg
145                 150                 155                 160

Asn Ala Leu Val Ala Ala Ile Arg Glu Ala Lys Leu Gly Val Lys
                165                 170                 175

Phe Val Thr Gly Thr Gln Gly Arg Val Ile Thr Leu Ile Phe Glu Asn
                180                 185                 190

Asn Asp Val Lys Gly Ala Val Thr Ala Asp Gly Lys Ile Trp Arg Ala
            195                 200                 205

Glu Gln Thr Val Leu Cys Ala Gly Ala Asn Ala Ala Gln Phe Leu Asp
        210                 215                 220

Phe Lys Asp Gln Leu Arg Pro Thr Ala Trp Thr Leu Ala His Ile Arg
225                 230                 235                 240

Leu Lys Pro Glu Glu Arg Ala Leu Tyr Lys Asn Leu Pro Val Ile Phe
                245                 250                 255

Asn Ile Glu Lys Gly Phe Phe Phe Glu Pro Asp Glu Glu Arg Gly Glu
                260                 265                 270

Ile Lys Ile Cys Asp Glu His Pro Gly Tyr Thr Asn Met Val Lys Ser
            275                 280                 285

Ala Asp Gly His Leu Thr Ser Leu Pro Phe Gly Lys Thr Gln Ile Pro
        290                 295                 300

Lys Glu Ser Glu Ala Arg Val Arg Ala Leu Leu Ser Glu Thr Met Pro
305                 310                 315                 320

Gln Leu Ala Asp Arg Pro Phe Ser Phe Ala Arg Val Cys Trp Cys Ala
                325                 330                 335

Asp Thr Ala Asn Arg Glu Phe Ile Ile Asp Arg His Pro Glu His Pro
            340                 345                 350

Ser Leu Val Leu Gly Cys Gly Ala Ser Gly Arg Gly Phe Lys Tyr Leu
        355                 360                 365

Pro Ser Ile Gly Asn Leu Ile Val Asp Ala Ile Glu Asp Lys Val Pro
370                 375                 380

Glu Lys Val His Lys Leu Thr Arg Trp Ser Pro Asp Ile Ala Val Asp
385                 390                 395                 400

Arg Lys Trp Arg Asp Thr Leu Gly Arg Phe Gly Gly Pro Asn Arg Val
                405                 410                 415

Met Asp Phe His Asp Val Lys Glu Trp Thr Asn Val Gln Asn Lys Asp
            420                 425                 430

Thr Ala Lys Leu
        435

<210> SEQ ID NO 15
<211> LENGTH: 438
<212> TYPE: PRT
<213> ORGANISM: Aspergillus fumigatus
```

<400> SEQUENCE: 15

```
Met Ala Val Thr Lys Ser Ser Leu Leu Ile Val Gly Ala Gly Thr
1               5                   10                  15

Trp Gly Thr Ser Thr Ala Leu His Leu Ala Arg Arg Gly Tyr Thr Asn
                20                  25                  30

Val Thr Val Leu Asp Pro Tyr Pro Val Pro Ser Ala Ile Ser Ala Gly
            35                  40                  45

Asn Asp Val Asn Lys Val Ile Ser Ser Gly Gln Tyr Ser Asn Asn Lys
50                  55                  60

Asp Glu Ile Glu Val Asn Glu Ile Leu Ala Glu Glu Ala Phe Asn Gly
65                  70                  75                  80

Trp Lys Asn Asp Pro Leu Phe Lys Pro Tyr Tyr His Asp Thr Gly Leu
                85                  90                  95

Leu Met Ser Ala Cys Ser Gln Glu Gly Leu Asp Arg Leu Gly Val Arg
                100                 105                 110

Val Arg Pro Gly Glu Asp Pro Asn Leu Val Glu Leu Thr Arg Pro Glu
            115                 120                 125

Gln Phe Arg Lys Leu Ala Pro Glu Gly Val Leu Gln Gly Asp Phe Pro
130                 135                 140

Gly Trp Lys Gly Tyr Phe Ala Arg Ser Gly Ala Gly Trp Ala His Ala
145                 150                 155                 160

Arg Asn Ala Leu Val Ala Ala Ala Arg Glu Ala Gln Arg Met Gly Val
                165                 170                 175

Lys Phe Val Thr Gly Thr Pro Gln Gly Arg Val Val Thr Leu Ile Phe
            180                 185                 190

Glu Asn Asn Asp Val Lys Gly Ala Val Thr Gly Asp Gly Lys Ile Trp
            195                 200                 205

Arg Ala Glu Arg Thr Phe Leu Cys Ala Gly Ala Ser Ala Gly Gln Phe
210                 215                 220

Leu Asp Phe Lys Asn Gln Leu Arg Pro Thr Ala Trp Thr Leu Val His
225                 230                 235                 240

Ile Ala Leu Lys Pro Glu Glu Arg Ala Leu Tyr Lys Asn Ile Pro Val
                245                 250                 255

Ile Phe Asn Ile Glu Arg Gly Phe Phe Phe Glu Pro Asp Glu Glu Arg
            260                 265                 270

Gly Glu Ile Lys Ile Cys Asp Glu His Pro Gly Tyr Thr Asn Met Val
            275                 280                 285

Gln Ser Ala Asp Gly Thr Met Met Ser Ile Pro Phe Glu Lys Thr Gln
290                 295                 300

Ile Pro Lys Glu Ala Glu Thr Arg Val Arg Ala Leu Leu Lys Glu Thr
305                 310                 315                 320

Met Pro Gln Leu Ala Asp Arg Pro Phe Ser Phe Ala Arg Ile Cys Trp
                325                 330                 335

Cys Ala Asp Thr Ala Asn Arg Gly Phe Leu Ile Asp Arg His Pro Gln
                340                 345                 350

Tyr His Ser Leu Val Leu Gly Cys Gly Ala Ser Gly Arg Gly Phe Lys
            355                 360                 365

Tyr Leu Pro Ser Ile Gly Asn Leu Ile Val Asp Ala Met Glu Gly Lys
            370                 375                 380

Val Pro Gln Lys Ile His Glu Leu Ile Lys Trp Asn Pro Asp Ile Ala
385                 390                 395                 400

Ala Asn Arg Asn Trp Arg Asp Thr Leu Gly Arg Phe Gly Gly Pro Asn
```

-continued

```
                405                 410                 415
Arg Val Met Asp Phe His Asp Val Lys Glu Trp Thr Asn Val Gln Tyr
            420                 425                 430

Arg Asp Ile Ser Lys Leu
            435

<210> SEQ ID NO 16
<211> LENGTH: 437
<212> TYPE: PRT
<213> ORGANISM: Aspergillus terreus

<400> SEQUENCE: 16

Met Pro Val Thr Lys Ser Ser Ile Leu Ile Ile Gly Ala Gly Thr
1               5                   10                  15

Trp Gly Cys Ser Thr Ala Leu His Leu Ala Arg Arg Gly Tyr Thr Asn
            20                  25                  30

Val Thr Val Leu Asp Pro Tyr Pro Val Pro Ser Ala Ile Ser Ala Gly
            35                  40                  45

Asn Asp Val Asn Lys Ile Ile Ser Ser Gly Gln Tyr Ser Ser Lys Lys
50                  55                  60

Asp Glu Val Glu Val Asn Glu Ile Ile Ala Glu Gln Ala Phe Asn Gly
65                  70                  75                  80

Trp Lys Asn Asp Pro Ile Phe Lys Pro Tyr Tyr His Asp Thr Gly Val
            85                  90                  95

Val Met Ser Ala Thr Thr Gln Glu Gly Leu Glu Arg Leu Gly Val Arg
            100                 105                 110

Val Arg Pro Glu Asp Glu Pro Asp Val Ala Glu Leu Thr Arg Pro Glu
            115                 120                 125

Gln Phe Arg Gln Leu Ala Pro Gly Val Leu Lys Gly Asn Phe Pro Gly
            130                 135                 140

Trp Arg Gly Tyr His Ile Arg Ser Asn Ala Gly Trp Ala His Ala Arg
145                 150                 155                 160

Asn Ala Leu Val Ala Ala Ala Arg Glu Ala Gln Arg Leu Gly Val Arg
            165                 170                 175

Phe Val Ala Gly Ser Pro Gln Gly Arg Val Ile Thr Leu Ile Phe Glu
            180                 185                 190

Asn Asn Asp Val Lys Gly Ala Val Thr Ala Asp Gly Lys Ile Trp Arg
            195                 200                 205

Ala Glu Gln Thr Ile Leu Cys Ala Gly Ala Ala Ala Gly Gln Phe Leu
            210                 215                 220

Asp Phe Lys Asp Gln Leu Arg Pro Thr Ala Trp Thr Leu Val His Ile
225                 230                 235                 240

Gln Leu Lys Pro Glu Glu Arg Ala Gln Tyr Lys Asn Met Pro Val Val
            245                 250                 255

Phe Asn Ile Glu Lys Gly Phe Phe Glu Pro Asp Glu Glu Arg Gly
            260                 265                 270

Glu Ile Lys Ile Cys Asp Glu His Pro Gly Tyr Thr Asn Met Thr Thr
            275                 280                 285

Gly Ala Asp Gly Arg Val Arg Ser Ile Pro Phe Glu Lys Thr Gln Val
            290                 295                 300

Pro Arg Glu Ala Glu Met Arg Val Arg Lys Leu Leu Ser Glu Thr Met
305                 310                 315                 320

Pro Gln Leu Ala Asp Arg Pro Phe Ser Phe Ala Arg Ile Cys Trp Cys
            325                 330                 335
```

Ala Asp Thr Pro Asn Arg Glu Phe Ile Ile Asp Arg His Pro Glu Tyr
            340                 345                 350

Pro Ser Leu Val Leu Gly Cys Gly Ala Ser Gly Arg Gly Phe Lys Tyr
        355                 360                 365

Leu Pro Ser Ile Gly Ser Ile Ile Ala Asp Ala Met Glu Asp Lys Thr
    370                 375                 380

Pro Ala Lys Ile His Lys Leu Ile Arg Trp Ser Pro Glu Ile Ala Ile
385                 390                 395                 400

Asn Arg Asn Trp Gly Asp Arg Leu Gly Arg Phe Gly Pro Asn Arg
                405                 410                 415

Val Met Asp Phe Asn Glu Val Lys Glu Trp Thr Asn Val Thr Gln Arg
            420                 425                 430

Asp Ile Ser Lys Leu
            435

<210> SEQ ID NO 17
<211> LENGTH: 440
<212> TYPE: PRT
<213> ORGANISM: Fusarium oxysporum

<400> SEQUENCE: 17

Ala Ser Thr Leu Thr Lys Gln Ser Gln Ile Leu Ile Val Gly Gly Gly
1               5                   10                  15

Thr Trp Gly Cys Ser Thr Ala Leu His Leu Ala Arg Arg Gly Tyr Thr
            20                  25                  30

Asn Val Thr Val Leu Asp Val Asn Arg Ile Pro Ser Pro Ile Ser Ala
        35                  40                  45

Gly His Asp Val Asn Lys Leu Ala Gly Arg Leu Ser Thr Ala Asp Ser
    50                  55                  60

Lys Gly Asp Asp Glu Asp Ser Ile Trp Lys Ala Leu Ser Tyr Ala Ala
65                  70                  75                  80

Ala Gln Gly Trp Leu His Asp Pro Val Phe Gln Pro Phe Cys His Asn
                85                  90                  95

Thr Gly Ser Val Val Ala Gly Ser Thr Pro Lys Ser Ile Lys Gln Leu
            100                 105                 110

Val Glu Asp Glu Ile Gly Asp Ile Asp Gln Tyr Thr Pro Leu Asn
        115                 120                 125

Thr Ala Glu Asp Phe Arg Lys Thr Met Pro Gly Ile Leu Thr Gly
    130                 135                 140

Asn Phe Pro Gly Trp Lys Gly Phe Tyr Lys Pro Thr Gly Ser Gly Trp
145                 150                 155                 160

Val His Ala Arg Lys Ala Met Lys Ala Ala Phe Glu Glu Ser Glu Arg
                165                 170                 175

Leu Gly Val Lys Phe Ile Thr Gly Ser Pro Glu Gly Lys Val Glu Ser
            180                 185                 190

Leu Ile Phe Glu Asp Gly Asp Val Arg Gly Ala Lys Thr Ala Asp Gly
        195                 200                 205

Lys Glu His Arg Ala Asp Arg Thr Ile Leu Ser Ala Gly Ala Ser Ala
    210                 215                 220

Glu Phe Phe Leu Asp Phe Glu Asn Gln Ile Gln Pro Thr Ala Trp Thr
225                 230                 235                 240

Leu Gly His Ile Gln Ile Thr Pro Glu Glu Thr Lys Leu Tyr Lys Asn
                245                 250                 255

Leu Pro Pro Leu Phe Asn Ile Asn Gln Gly Phe Phe Met Glu Pro Asp
            260                 265                 270

-continued

```
Glu Asp Leu His Gln Leu Lys Met Cys Asp Glu His Pro Gly Tyr Cys
        275                 280                 285

Asn Trp Val Glu Lys Pro Gly Ser Lys Tyr Pro Gln Ser Ile Pro Phe
        290                 295                 300

Ala Lys His Gln Val Pro Thr Glu Ala Glu Arg Arg Met Lys Gln Phe
305                 310                 315                 320

Leu Lys Asp Ile Met Pro Gln Leu Ala Asp Arg Pro Leu Val His Ala
                325                 330                 335

Arg Ile Cys Trp Cys Ala Asp Thr Gln Asp Arg Met Phe Leu Ile Thr
                340                 345                 350

Tyr His Pro Arg His Pro Ser Leu Val Ile Ala Ser Gly Asp Cys Gly
                355                 360                 365

Thr Gly Tyr Lys His Ile Thr Ser Ile Gly Lys Phe Ile Ser Asp Cys
        370                 375                 380

Met Glu Gly Thr Leu Glu Glu Arg Phe Ala Lys Tyr Trp Arg Trp Arg
385                 390                 395                 400

Pro Glu Lys Phe Thr Glu Phe Trp Gly Lys Asp Pro Leu Asp Arg Phe
                405                 410                 415

Gly Ala Asp Asp Lys Ile Met Asp Leu Pro Lys Ser Val Glu Gly
                420                 425                 430

Trp Thr Asn Ile Lys Asn Asp Ile
        435                 440

<210> SEQ ID NO 18
<211> LENGTH: 445
<212> TYPE: PRT
<213> ORGANISM: Aspergillus oryzae

<400> SEQUENCE: 18

Met Thr Ser Ser Lys Leu Thr Pro Thr Ser Ile Leu Ile Val Gly
1               5                   10                  15

Ala Gly Thr Trp Gly Cys Ser Thr Ala Leu His Leu Ala Arg Arg Gly
                20                  25                  30

Tyr Lys Asn Val Thr Val Leu Asp Pro His Pro Val Pro Ser Pro Ile
        35                  40                  45

Ala Ala Gly Asn Asp Ile Asn Lys Ile Met Glu His Arg Glu Val Lys
50                  55                  60

Ala Ser Glu Thr Asp Pro Trp Ser Ile Ala Phe Ser Thr Cys Thr Arg
65                  70                  75                  80

Ala Ala Leu Lys Gly Trp Lys Asn Asp Pro Val Phe Gln Pro Tyr Phe
                85                  90                  95

His Glu Thr Gly Ala Ile Val Ser Gly His Thr Ala Ser Leu Ile Lys
                100                 105                 110

His Ile Gln Glu His Glu Ile Asp Ser Ser Asp Ala Glu Phe Ile Lys
        115                 120                 125

Leu Asn Thr Ala Glu Asp Phe Arg Lys Thr Met Pro Pro Gly Ile Leu
        130                 135                 140

Thr Gly Asn Phe Pro Gly Trp Lys Gly Trp Leu Asn Lys Thr Gly Ala
145                 150                 155                 160

Gly Trp Ile His Ala Lys Lys Ala Met Phe Ser Ala Tyr Thr Glu Ala
                165                 170                 175

Lys Arg Leu Gly Val Thr Phe Ile Thr Gly Ser Pro Glu Gly Asp Val
                180                 185                 190

Val Ser Leu Ile Tyr Glu Asn Gly Asp Val Val Gly Ala Arg Thr Ala
```

```
                195                 200                 205
Asp Gly Thr Val His Arg Ala Asp His Thr Ile Leu Ser Ala Gly Ala
210                 215                 220

Gly Ser Asp Arg Leu Leu Asp Phe Lys Lys Gln Leu Arg Pro Thr Ala
225                 230                 235                 240

Trp Thr Leu Cys His Ile Arg Met Thr Pro Asp Glu Ala Lys Lys Tyr
                245                 250                 255

Arg Asn Leu Pro Val Leu Phe Asn Val Ala Lys Gly Phe Phe Met Glu
            260                 265                 270

Pro Asp Glu Asp Asn His Glu Leu Lys Ile Cys Asp Glu His Pro Gly
        275                 280                 285

Tyr Cys Asn Phe Val Pro Asp Pro Lys His Gly Gly Glu Val Arg Ser
    290                 295                 300

Ile Pro Phe Ala Lys His Gln Ile Pro Leu Glu Ala Glu Ala Arg Ala
305                 310                 315                 320

Arg Asp Phe Leu Arg Asp Thr Met Pro His Leu Ala Asp Arg Pro Leu
                325                 330                 335

Ser Phe Ala Arg Ile Cys Trp Asp Ala Asp Thr Val Asp Arg Ala Phe
            340                 345                 350

Leu Ile Asp Arg His Pro Glu Tyr Arg Ser Leu Leu Leu Ala Val Gly
        355                 360                 365

Gly Ser Gly Asn Gly Ala Met Gln Met Pro Thr Ile Gly Gly Phe Ile
    370                 375                 380

Ala Asp Ala Leu Glu Gly Asn Leu Gln Lys Glu Leu Lys His Ala Leu
385                 390                 395                 400

Arg Trp Arg Pro Glu Ile Ala Ala Gln Arg Asp Trp Lys Asp Thr Gln
                405                 410                 415

Asn Arg Phe Gly Gly Pro Asn Lys Val Met Asp Phe Gln Lys Val Gly
            420                 425                 430

Glu Asn Glu Trp Thr Lys Ile Gly Asp Lys Ser Arg Leu
        435                 440                 445

<210> SEQ ID NO 19
<211> LENGTH: 445
<212> TYPE: PRT
<213> ORGANISM: Aspergillus fumigatus

<400> SEQUENCE: 19

Met Ala Pro Ser Ile Leu Ser Thr Glu Ser Ile Ile Val Ile Gly
1               5                   10                  15

Ala Gly Thr Trp Gly Cys Ser Thr Ala Leu His Leu Ala Arg Arg Gly
                20                  25                  30

Tyr Lys Asp Val Thr Val Leu Asp Pro His Pro Val Pro Ser Pro Ile
            35                  40                  45

Ala Ala Gly Asn Asp Ile Asn Lys Ile Met Glu His Ser Glu Leu Lys
        50                  55                  60

Asp Gly Ser Ser Asp Pro Arg Ser Ala Ala Phe Ser Thr Phe Thr Arg
65                  70                  75                  80

Ala Ala Leu Lys Ala Trp Lys Thr Asp Pro Val Phe Gln Pro Tyr Phe
                85                  90                  95

His Glu Thr Gly Phe Ile Ile Ser Gly His Thr Pro Ala Leu Ile Asp
            100                 105                 110

His Ile Arg Lys Asp Glu Val Glu Pro Ser Glu Thr Asn Phe Val Lys
        115                 120                 125
```

Leu Glu Thr Ala Glu Asp Phe Arg Arg Thr Met Pro Pro Gly Val Leu
130                 135                 140

Thr Gly Asp Phe Pro Gly Trp Lys Gly Trp Leu His Lys Ser Gly Ala
145                 150                 155                 160

Gly Trp Ile His Ala Lys Lys Ala Met Ile Ser Ala Phe Asn Glu Ala
                165                 170                 175

Lys Arg Leu Gly Val Arg Phe Val Thr Gly Ser Pro Glu Gly Asn Val
            180                 185                 190

Val Ser Leu Val Tyr Glu Asp Gly Asp Val Val Gly Ala Arg Thr Ala
        195                 200                 205

Asp Gly Arg Val His Lys Ala His Arg Thr Ile Leu Ser Ala Gly Ala
    210                 215                 220

Gly Ser Asp Ser Leu Leu Asp Phe Lys Lys Gln Leu Arg Pro Thr Ala
225                 230                 235                 240

Trp Thr Leu Cys His Ile Gln Met Gly Pro Glu Glu Val Lys Gln Tyr
                245                 250                 255

Arg Asn Leu Pro Val Leu Phe Asn Ile Ala Lys Gly Phe Phe Met Glu
            260                 265                 270

Pro Asp Glu Asp Lys His Glu Leu Lys Ile Cys Asp Glu His Pro Gly
        275                 280                 285

Tyr Cys Asn Phe Leu Pro Asp Pro Asn Arg Pro Gly Gln Glu Lys Ser
    290                 295                 300

Val Pro Phe Ala Lys His Gln Ile Pro Leu Glu Ala Glu Ala Arg Ala
305                 310                 315                 320

Arg Asp Phe Leu His Asp Thr Met Pro His Leu Ala Asp Arg Pro Leu
                325                 330                 335

Ser Phe Ala Arg Ile Cys Trp Asp Ala Asp Thr Pro Asp Arg Ala Phe
            340                 345                 350

Leu Ile Asp Arg His Pro Glu His Pro Ser Leu Leu Val Ala Val Gly
        355                 360                 365

Gly Ser Gly Asn Gly Ala Met Gln Met Pro Thr Ile Gly Gly Phe Ile
    370                 375                 380

Ala Asp Ala Leu Glu Ser Lys Leu Gln Lys Glu Val Lys Asp Ile Val
385                 390                 395                 400

Arg Trp Arg Pro Glu Thr Ala Val Asp Arg Asp Trp Arg Ala Thr Gln
                405                 410                 415

Asn Arg Phe Gly Gly Pro Asp Arg Ile Met Asp Phe Gln Gln Val Gly
            420                 425                 430

Glu Asp Gln Trp Thr Lys Ile Gly Glu Ser Arg Gly Pro
        435                 440                 445

<210> SEQ ID NO 20
<211> LENGTH: 427
<212> TYPE: PRT
<213> ORGANISM: Pichia sp.

<400> SEQUENCE: 20

Met Glu Ser Ile Ile Ile Val Gly Ala Gly Thr Phe Gly Leu Ser Thr
1               5                   10                  15

Ala Leu Gln Leu Ala Arg Asp Gly Tyr Lys Asn Ile Lys Cys Phe Asp
            20                  25                  30

Lys Phe Pro Val Pro Ser Glu Ile Ala Ala Gly Asn Asp Ser Asn Lys
        35                  40                  45

Ile Phe His Tyr Asp Tyr Val Ala Pro Leu Ala Lys Pro Asn Ser Lys
    50                  55                  60

Glu Arg Leu Ser Leu Glu Ala Leu His Leu Trp Lys Thr Asp Pro Val
65                  70                  75                  80

Tyr Lys Pro Tyr Tyr His Pro Val Gly Phe Ile Leu Ala Ala Ser Ser
                85                  90                  95

Asp Ala Pro Leu Leu His Asp Lys Glu Tyr Tyr Glu Glu Leu Gln Lys
            100                 105                 110

Asn Gly Leu Arg Asn Tyr Arg Tyr Ile Ser Thr Pro Glu Glu Phe Arg
        115                 120                 125

Glu Tyr Leu Pro Ile Leu Lys Gly Pro Leu Pro Asn Trp Arg Gly Tyr
    130                 135                 140

Val Leu Asp Gly Asp Asn Gly Trp Leu His Ala Arg Asp Ser Leu Lys
145                 150                 155                 160

Ser Ala Tyr Glu Glu Cys Lys Arg Leu Gly Val Glu Phe Val Phe Gly
                165                 170                 175

Asp Asp Gly Glu Ile Val Glu Leu Leu Asn Glu Asn Gly Lys Leu Thr
            180                 185                 190

Gly Ile Arg Ala Arg Ser Gly Ala Ile Phe Ser Ala Gln Lys Tyr Val
        195                 200                 205

Leu Ser Ser Gly Ala Asn Ala Val Thr Leu Leu Asn Phe Gln Arg Gln
    210                 215                 220

Leu Glu Gly Lys Cys Phe Thr Leu Ala His Phe Lys Val Thr Asp Glu
225                 230                 235                 240

Glu Ala Lys Ala Phe Lys Ser Leu Pro Val Leu Phe Asn Ala Glu Lys
                245                 250                 255

Gly Phe Phe Phe Glu Ala Asp Glu Asn Glu Ile Lys Ile Cys Asn
            260                 265                 270

Glu Tyr Pro Gly Phe Thr His Thr Asn Glu Ser Gly Glu Ser Ile Pro
        275                 280                 285

Leu Tyr Arg Met Glu Ile Pro Leu Glu Ser Ala Leu Glu Ile Arg Gln
    290                 295                 300

Tyr Leu Lys Glu Thr Met Pro Gln Phe Ala Asp Arg Pro Phe Thr Lys
305                 310                 315                 320

Thr Arg Ile Cys Trp Cys Thr Asp Ser Pro Asp Met Gln Leu Ile Leu
                325                 330                 335

Cys Thr His Pro Glu Tyr Thr Asn Leu Ile Val Ala Ser Gly Asp Ser
            340                 345                 350

Gly Asn Ser Phe Lys Ile Met Pro Ile Ile Gly Lys Tyr Val Ser Lys
        355                 360                 365

Val Val Thr Lys Gly Asp Lys Gly Leu Asp Pro Glu Asp Lys Glu Cys
    370                 375                 380

Trp Lys Trp Arg Pro Glu Thr Trp Asp Lys Arg Gly Gln Val Arg Trp
385                 390                 395                 400

Gly Gly Arg Tyr Arg Val Ala Asp Leu Asn Glu Ile Glu Glu Trp Val
                405                 410                 415

Ser Val Glu Asn Pro Thr Pro His Lys Leu Glu
            420                 425

<210> SEQ ID NO 21
<211> LENGTH: 426
<212> TYPE: PRT
<213> ORGANISM: Debaryomyces hansenii

<400> SEQUENCE: 21

Met Asp Lys Pro Gly Lys Ile Leu Ile Ile Gly Ala Gly Thr Phe Gly

-continued

```
1               5                   10                  15
Leu Ser Thr Ala Leu His Leu Leu Arg Gln Gly Glu Lys Asp Val Ile
                20                  25                  30
Leu Val Asp Pro Tyr Ala Val Pro Ser Pro Phe Ser Ala Gly Asn Asp
                35                  40                  45
Val Asn Lys Ile Ile Gln Thr Thr Ser Asp Asp Phe Tyr Ser Lys
    50                  55                  60
Leu Ala Leu Glu Ala Leu Glu Met Trp Arg Glu Asp Asn Val Phe Asn
65                  70                  75                  80
Lys Ala Phe Ala Glu Thr Gly Ile Ile Tyr Ala Ala Thr Gly Lys Glu
                85                  90                  95
Gln Arg Glu Ser Ile Asp Tyr Arg Tyr Glu Tyr Leu Leu Gly Arg Lys
                100                 105                 110
Asp Lys Val Val Lys Leu Asn Ser Val Glu Asp Tyr Glu Lys Tyr Val
                115                 120                 125
Pro Asn Lys Glu Gly Ser Lys Ser Tyr Pro Asn Lys Phe Gln Lys Trp
            130                 135                 140
Tyr Gly Tyr Tyr Gln Glu Lys Asn Cys Gly Trp Ala Phe Ala Arg Leu
145                 150                 155                 160
Ala Leu Glu Asn Cys Val Glu Glu Cys Arg Lys Leu Gly Ala Lys Phe
                165                 170                 175
Val Ile Asp Ser Ala Glu Glu Leu Leu Phe Ser Glu Asp Gly Ala Cys
                180                 185                 190
Val Gly Val His Thr Ser Asn Gly Asn Ile Ile Glu Ala Asp Arg Thr
                195                 200                 205
Ile Ile Cys Ala Gly Ala Asn Ser Phe Lys Phe Leu Asn Phe Glu Gln
                210                 215                 220
Gln Leu Leu Ala Lys Cys Tyr Thr Leu Gly His Ile Lys Leu Thr Asp
225                 230                 235                 240
Asp Glu Ala Ala Leu Leu Lys Gly Met Pro Val Val Leu Asn Leu Asp
                245                 250                 255
Gly Gly Phe Val Phe Glu Pro Asp Leu Asn Asn Glu Ile Lys Phe Cys
                260                 265                 270
Asn Glu Phe Pro Gly Tyr Val Asn Ile Val Asn Glu Asp Ser Val Pro
                275                 280                 285
Ser Phe Lys Asp Ser Ile Pro Lys Glu Ala Glu Asp Gln Met Arg Ala
                290                 295                 300
Phe Leu Arg Gln Val Phe Pro Glu Phe Ala Glu Arg Glu Phe Ser Leu
305                 310                 315                 320
Ala Arg Ile Cys Trp Cys Thr Asp Thr Pro Asp Arg His Phe Leu Ile
                325                 330                 335
Cys Glu His Pro Gly His Lys Asn Leu Val Leu Gly Thr Gly Asp Ser
                340                 345                 350
Gly Gln Gly Phe Lys Tyr Met Pro Asn Val Gly Lys Tyr Ile Ser Gln
                355                 360                 365
Val Ala Leu Lys Gly Glu Asn Ser Leu Asp Lys Asp Lys Lys Glu Leu
                370                 375                 380
Trp Arg Trp Arg Pro Asp Met Gly Lys Lys Arg Asp Leu Lys Asp Leu
385                 390                 395                 400
Gln Gly Arg Tyr Gly Gly Ser Asn Glu Val Leu Asp Leu Lys Asn Val
                405                 410                 415
Lys Gln Trp Ser Asn Gly Lys Ser His Leu
                420                 425
```

```
<210> SEQ ID NO 22
<211> LENGTH: 437
<212> TYPE: PRT
<213> ORGANISM: Coniochaeta sp.

<400> SEQUENCE: 22
```

Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Asp His Gly
    50                  55                  60

Asn Lys Val Asn Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Lys Gly Ile Glu Lys Leu Lys Lys Tyr Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ser Thr Leu Leu Met Cys Glu His Pro Lys Trp Lys Asn Phe
        355                 360                 365

Ile Leu Ala Thr Gly Asp Ser Gly His Ser Phe Lys Ile Leu Pro Asn

```
                    370                 375                 380
Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 23
<211> LENGTH: 1314
<212> TYPE: DNA
<213> ORGANISM: Coniochaeta sp.

<400> SEQUENCE: 23
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatcatg caacaaggt gaacctgcaa atgagtctag aggctagaca gatgtggaag      240
gaggatgagt tattccagcc cttctttcac aataccggca gaatggactg cgaacacacg     300
cctaagggta tcgagaaact gaaaaagtat taccagaaac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtgg tgtaaagttc      540 ggattcggcg cgctggatc cttcaagcaa ccccttttcg acgatgaagg cacaacttgc      600
attggcgttg agacggcaga tggtaccaaa tattacgctg acaaggtggt cttagcagct     660
ggcgcatgga gcccaaccct ggtggacctg aagatcaat gttgctcgaa ggcttgggtg      720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc ccatctccg      900 aaacggatat cagtaccacg atcgcacgcc aagcatccca cagacactta tccgacgca     960 tccgaagtca gcatcaaaaa agcaatcgcg acgtttctcc ctcgatttca ggacaaggag    1020
ctcttcaatc gcgccttgtg ctggtgtaca gacactgcgg actctactct cttgatgtgt    1080
gaacacccca atggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314

<210> SEQ ID NO 24
<211> LENGTH: 437
<212> TYPE: PRT
<213> ORGANISM: Coniochaeta sp.

<400> SEQUENCE: 24

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30
```

```
Ala Pro Ala Asn Ile Thr Val Leu Asp Thr Phe Glu Ile Pro Ser Ala
         35                  40                  45

Gln Ser Ala Gly His Asp Leu Asn Lys Ile Met Gly Ile Asp His Gly
    50                  55                  60

Asn Lys Val Asn Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu Ser Thr Pro Lys Gly Ile Glu Lys Leu Lys Lys Tyr Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
        210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Ser Glu Tyr Gly Phe Phe Phe Glu Pro Asp
            260                 265                 270

Glu Phe Gly Val Ile Lys Val Cys Asn Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ser Thr Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
            435
```

<210> SEQ ID NO 25
<211> LENGTH: 30
<212> TYPE: DNA
<213> ORGANISM: Artificial
<220> FEATURE:
<223> OTHER INFORMATION: primer

<400> SEQUENCE: 25
gcacaccttt attacaccaa actcatcagg                                       30

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
ataaaggtgt gcaacgagtt cccaggattc                                       30

<210> SEQ ID NO 27
<211> LENGTH: 30
<212> TYPE: DNA
<213> ORGANISM: Artificial
<220> FEATURE:
<223> OTHER INFORMATION: primer

<400> SEQUENCE: 27
gctattatac acaactggga caccttata                                        30

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
gaatatggct tcttctttga gcctgatgag                                       30

<210> SEQ ID NO 29
<211> LENGTH: 30
<212> TYPE: DNA
<213> ORGANISM: Artificial
<220> FEATURE:
<223> OTHER INFORMATION: primer

<400> SEQUENCE: 29
ttcgcagtcc attctgccgg tattgtgaaa                                       30

<210> SEQ ID NO 30
<211> LENGTH: 30
<212> TYPE: DNA
<213> ORGANISM: Artificial
<220> FEATURE:
<223> OTHER INFORMATION: primer

<400> SEQUENCE: 30
atggactgcg aaagcacgcc taagggtatc                                       30

<210> SEQ ID NO 31
<211> LENGTH: 30
<212> TYPE: DNA
<213> ORGANISM: Artificial
<220> FEATURE:
<223> OTHER INFORMATION: primer

```
<400> SEQUENCE: 31
aggcgtgctt tcgcagtcca ttctgccggt                                         30

<210> SEQ ID NO 32
<211> LENGTH: 30
<212> TYPE: DNA
<213> ORGANISM: Artificial
<220> FEATURE:
<223> OTHER INFORMATION: primer

<400> SEQUENCE: 32
gaaagcacgc ctgcgggtat cgagaaactg                                         30

<210> SEQ ID NO 33
<211> LENGTH: 30
<212> TYPE: DNA
<213> ORGANISM: Artificial
<220> FEATURE:
<223> OTHER INFORMATION: primer

<400> SEQUENCE: 33
gaaagcacgc ctgagggtat cgagaaactg                                         30

<210> SEQ ID NO 34
<211> LENGTH: 30
<212> TYPE: DNA
<213> ORGANISM: Artificial
<220> FEATURE:
<223> OTHER INFORMATION: primer

<400> SEQUENCE: 34
ctcgataccc ttaggcgtgc tttcgcagtc                                         30

<210> SEQ ID NO 35
<211> LENGTH: 30
<212> TYPE: DNA
<213> ORGANISM: Artificial
<220> FEATURE:
<223> OTHER INFORMATION: primer

<400> SEQUENCE: 35
aagggtatcg aggcactgaa aaagtattac                                         30

<210> SEQ ID NO 36
<211> LENGTH: 30
<212> TYPE: DNA
<213> ORGANISM: Artificial
<220> FEATURE:
<223> OTHER INFORMATION: primer

<400> SEQUENCE: 36
aagggtatcg aggatctgaa aaagtattac                                         30

<210> SEQ ID NO 37
<211> LENGTH: 30
<212> TYPE: DNA
<213> ORGANISM: Artificial
<220> FEATURE:
<223> OTHER INFORMATION: primer

<400> SEQUENCE: 37
ctggtaatac tttttcagtt tctcgatacc                                         30

<210> SEQ ID NO 38
```

```
<211> LENGTH: 30
<212> TYPE: DNA
<213> ORGANISM: Artificial
<220> FEATURE:
<223> OTHER INFORMATION: primer

<400> SEQUENCE: 38
aaagtattac caggcactgc acgatgccgg                                    30

<210> SEQ ID NO 39
<211> LENGTH: 30
<212> TYPE: DNA
<213> ORGANISM: Artificial
<220> FEATURE:
<223> OTHER INFORMATION: primer

<400> SEQUENCE: 39
aaagtattac caggaactgc acgatgccgg                                    30

<210> SEQ ID NO 40
<211> LENGTH: 30
<212> TYPE: DNA
<213> ORGANISM: Artificial
<220> FEATURE:
<223> OTHER INFORMATION: primer

<400> SEQUENCE: 40
aaagtattac cagagcctgc acgatgccgg                                    30

<210> SEQ ID NO 41
<211> LENGTH: 30
<212> TYPE: DNA
<213> ORGANISM: Artificial
<220> FEATURE:
<223> OTHER INFORMATION: primer

<400> SEQUENCE: 41
aaagtattac cagaccctgc acgatgccgg                                    30

<210> SEQ ID NO 42
<211> LENGTH: 30
<212> TYPE: DNA
<213> ORGANISM: Artificial
<220> FEATURE:
<223> OTHER INFORMATION: primer

<400> SEQUENCE: 42
aaagtattac cagaacctgc acgatgccgg                                    30

<210> SEQ ID NO 43
<211> LENGTH: 30
<212> TYPE: DNA
<213> ORGANISM: Artificial
<220> FEATURE:
<223> OTHER INFORMATION: primer

<400> SEQUENCE: 43
aaagtattac cagcaactgc acgatgccgg                                    30

<210> SEQ ID NO 44
<211> LENGTH: 30
<212> TYPE: DNA
<213> ORGANISM: Artificial
<220> FEATURE:
<223> OTHER INFORMATION: primer

<400> SEQUENCE: 44
```
aaagtattac caggatctgc acgatgccgg                                          30

<210> SEQ ID NO 45
<211> LENGTH: 438
<212> TYPE: PRT
<213> ORGANISM: Emericella nidulans

<400> SEQUENCE: 45

Met Ala Pro Arg Ala Asn Thr Lys Ile Ile Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Ser Gly Ala Asn
        50                  55                  60

Lys His Asp Leu Gln Leu Ser Leu Glu Ala Phe Asp Met Trp Lys Asn
65              70                  75                  80

Asp Pro Leu Phe Lys Pro Phe Phe His Asn Val Gly Gln Met Asp Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
        130                 135                 140

Ile Lys Gly Trp Lys Gly Leu Phe Cys Gly Asp Gly Gly Trp Leu Ala
145             150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225             230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305             310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
            370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 46
<211> LENGTH: 1317
<212> TYPE: DNA
<213> ORGANISM: Emericella nidulans

<400> SEQUENCE: 46
atggctccgc gtgcgaatac gaaaatcatt gttgtcggtg gtggtggtac gatgggttca      60
agtacggctc tgcatctgct gcgtgcgggc tataccccga gcaacattac cgtgctggat     120
acgtatccga tcccgtcagc gcagtcggcc ggttacgacc tgaacaaaat ttttggtatc     180
agcggtgcaa ataaacatga tctgcaactg tctctggaag cgtttgatat gtggaaaaac     240
gacccgctgt ttaaaccgtt tttccacaat gtgggccaga tggatgttag ctctaccgaa     300
gaaggtatta aacgcctgcg tcgccgttac caaagtctgc tgcgtgccgg catcggtctg     360
gaaaaaacca acttcctgct ggaatccgaa gatgaaattc tggcgaaagc cccgcatttc     420
acgcgcgaac agatcaaagg ctggaaaggt ctgttttgcg gtgatggcgg ttggctggcc     480
gcagcaaaag caattaatgc tatcggccag tttctgaaag aacaaggtgt gaaatttggc     540
ttcggtgaag cgggtacctt caaaaaaccg ctgtttgcag atgctgacga aaaaacgtgc     600
attggcgttg aaaccgtcga tggtacgaaa tattacgcag acaaagtggt tctggctgcg     660
ggcgcttgga gttccaccct ggttgatctg gaagaacagt gtgtcagcaa agcgtgggtg     720
tttgcccaca tccaactgac cccggccgaa gccgcagctt ataaaaacac gccggtgatt     780
tatgatggcg actacggctt tttcatcgaa ccggatgaaa atggcattat caaagtttgc     840
gacgaatttc cgggtttcac ccattttaaa atgcaccagc cgtatggctc accggttccg     900
aaactgatta gtgtcccgcg ttcccatgca aaacacccga ccgatacgta cccgcatgca     960
tcggaagtca cgattaagaa agcgatcaac cgcttcctgc gcgtttttaa cgacaaagaa    1020
ctgttcaatc gcgcgatgtg ctggtgtacc gatacggccg acagcaatct gctggtttgt    1080
gaacacccgc gttggaaagg tttctatctg gcgaccggcg atagcggtca ttcttttaaa    1140
ctgctgccga atattggcaa acacgtcgtg gaactgctgg aaggtcgcct ggaatctgtg    1200
tttaaagatg cgtggcgctg gcgtccgggc tcaggtgatg cactgaaatc gcgtcgcgca    1260
gcaccggcga aagacctggc ggatatgccg ggttggcgta atgaagcgaa aatgtaa      1317

<210> SEQ ID NO 47
<211> LENGTH: 30
<212> TYPE: DNA
<213> ORGANISM: Artificial
<220> FEATURE:
<223> OTHER INFORMATION: primer

<400> SEQUENCE: 47
tttaatacct tcttcggtag agctaacatc                                      30

```
<210> SEQ ID NO 48
<211> LENGTH: 30
<212> TYPE: DNA
<213> ORGANISM: Artificial
<220> FEATURE:
<223> OTHER INFORMATION: primer

<400> SEQUENCE: 48
gccctgcgtc gccgttacca aagtctgctg                                          30

<210> SEQ ID NO 49
<211> LENGTH: 30
<212> TYPE: DNA
<213> ORGANISM: Artificial
<220> FEATURE:
<223> OTHER INFORMATION: primer

<400> SEQUENCE: 49
agcctgcgtc gccgttacca aagtctgctg                                          30

<210> SEQ ID NO 50
<211> LENGTH: 30
<212> TYPE: DNA
<213> ORGANISM: Artificial
<220> FEATURE:
<223> OTHER INFORMATION: primer

<400> SEQUENCE: 50
ctcctgcgtc gccgttacca aagtctgctg                                          30

<210> SEQ ID NO 51
<211> LENGTH: 10
<212> TYPE: DNA
<213> ORGANISM: Artificial
<220> FEATURE:
<223> OTHER INFORMATION: primer

<400> SEQUENCE: 51
aaaaaaaaaa                                                                10

<210> SEQ ID NO 52
<211> LENGTH: 30
<212> TYPE: DNA
<213> ORGANISM: Artificial
<220> FEATURE:
<223> OTHER INFORMATION: primer

<400> SEQUENCE: 52
aacctgcgtc gccgttacca aagtctgctg                                          30

<210> SEQ ID NO 53
<211> LENGTH: 30
<212> TYPE: DNA
<213> ORGANISM: Artificial
<220> FEATURE:
<223> OTHER INFORMATION: primer

<400> SEQUENCE: 53
cagctgcgtc gccgttacca aagtctgctg                                          30

<210> SEQ ID NO 54
<211> LENGTH: 30
<212> TYPE: DNA
<213> ORGANISM: Artificial
<220> FEATURE:
```

<223> OTHER INFORMATION: primer

<400> SEQUENCE: 54
gacctgcgtc gccgttacca aagtctgctg                              30

<210> SEQ ID NO 55
<211> LENGTH: 30
<212> TYPE: DNA
<213> ORGANISM: Artificial
<220> FEATURE:
<223> OTHER INFORMATION: primer

<400> SEQUENCE: 55
gaactgcgtc gccgttacca aagtctgctg                              30

<210> SEQ ID NO 56
<211> LENGTH: 30
<212> TYPE: DNA
<213> ORGANISM: Artificial
<220> FEATURE:
<223> OTHER INFORMATION: primer

<400> SEQUENCE: 56
acgcaggcgt ttaataccttt cttcggtaga                             30

<210> SEQ ID NO 57
<211> LENGTH: 30
<212> TYPE: DNA
<213> ORGANISM: Artificial
<220> FEATURE:
<223> OTHER INFORMATION: primer

<400> SEQUENCE: 57
gcccgttacc aaagtctgct gcgtgccggc                              30

<210> SEQ ID NO 58
<211> LENGTH: 30
<212> TYPE: DNA
<213> ORGANISM: Artificial
<220> FEATURE:
<223> OTHER INFORMATION: primer

<400> SEQUENCE: 58
agccgttacc aaagtctgct gcgtgccggc                              30

<210> SEQ ID NO 59
<211> LENGTH: 30
<212> TYPE: DNA
<213> ORGANISM: Artificial
<220> FEATURE:
<223> OTHER INFORMATION: primer

<400> SEQUENCE: 59
ctccgttacc aaagtctgct gcgtgccggc                              30

<210> SEQ ID NO 60
<211> LENGTH: 10
<212> TYPE: DNA
<213> ORGANISM: Artificial
<220> FEATURE:
<223> OTHER INFORMATION: primer

<400> SEQUENCE: 60
aaaaaaaaaa                                                    10

```
<210> SEQ ID NO 61
<211> LENGTH: 30
<212> TYPE: DNA
<213> ORGANISM: Artificial
<220> FEATURE:
<223> OTHER INFORMATION: primer

<400> SEQUENCE: 61
cagcgttacc aaagtctgct gcgtgccggc                                            30

<210> SEQ ID NO 62
<211> LENGTH: 30
<212> TYPE: DNA
<213> ORGANISM: Artificial
<220> FEATURE:
<223> OTHER INFORMATION: primer

<400> SEQUENCE: 62
gaccgttacc aaagtctgct gcgtgccggc                                            30

<210> SEQ ID NO 63
<211> LENGTH: 30
<212> TYPE: DNA
<213> ORGANISM: Artificial
<220> FEATURE:
<223> OTHER INFORMATION: primer

<400> SEQUENCE: 63
gaacgttacc aaagtctgct gcgtgccggc                                            30

<210> SEQ ID NO 64
<211> LENGTH: 30
<212> TYPE: DNA
<213> ORGANISM: Artificial
<220> FEATURE:
<223> OTHER INFORMATION: primer

<400> SEQUENCE: 64
ttggtaacgg cgacgcaggc gtttaatacc                                            30

<210> SEQ ID NO 65
<211> LENGTH: 30
<212> TYPE: DNA
<213> ORGANISM: Artificial
<220> FEATURE:
<223> OTHER INFORMATION: primer

<400> SEQUENCE: 65
gatctgctgc gtgccggcat cggtctggaa                                            30

<210> SEQ ID NO 66
<211> LENGTH: 30
<212> TYPE: DNA
<213> ORGANISM: Artificial
<220> FEATURE:
<223> OTHER INFORMATION: primer

<400> SEQUENCE: 66
gaactgctgc gtgccggcat cggtctggaa                                            30
```

GLYCATED HEMOGLOBIN OXIDASE VARIANT AND METHOD FOR MEASUREMENT

CROSS-REFERENCE TO RELATED APPLICATIONS

This application is the U.S. National Stage of PCT/JP2018/032389, filed Aug. 31, 2018, which claims priority to JP 2017-167890, filed Aug. 31, 2017.

The instant application contains a Sequence Listing which has been submitted in ASCII format via EFS-WEB and is hereby incorporated by reference in its entirety. Said ASCII copy, created on May 6, 2020, is named sequence.txt and is 100,412 bytes.

TECHNICAL FIELD

The present invention concerns glycated hemoglobin oxidase exerting activity on a plurality of types of glycated hemoglobin and a method for measurement of glycated hemoglobin using the same.

BACKGROUND ART

Glycated proteins are generated by non-enzymatic covalent bonding between aldehyde groups in aldoses, such as glucose (monosaccharides potentially containing aldehyde groups and derivatives thereof), and amino groups in proteins, followed by Amadori rearrangement.

In particular, hemoglobin A1c (HbA1c) has drawn attention as a glycemic control marker. HbA1c is a protein comprising glucose bound to the α-amino group at the N-terminal (amino-terminal) valine (Val) residue of the hemoglobin "β chain." The blood HbA1c level reflects the average blood glucose level for a given period of time in the past, and the measured value of HbA1c serves as an important indicator for diagnosis and control of diabetes conditions.

Several types of enzymatic methods involving the use of amadoriases have been known as methods for rapidly and simply measuring HbA1c.

Amadoriase is a collective term for enzymes that oxidize iminodiacetic acid or a derivative thereof (also referred to as an "amadori compound") in the presence of oxygen to catalyze a reaction to generate glyoxylic acid or α-ketoaldehyde, amino acid or peptide, and hydrogen peroxide. Amadoriases are known to be useful for measuring HbA1c by enzymatic methods. An example of a substrate that is known to be oxidized by amadoriases is α-fructosyl-valyl-histidine (hereafter referred to as "αFVH").

Amadoriases have been found in bacteria, yeast, and fungi. For example, amadoriases derived from the genera *Coniochaeta, Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Debaryomyces, Corynebacterium, Agrobacterium*, and *Arthrobacter* have been reported (e.g., Patent Documents 1 and 6 to 15 and Non-Patent Documents 1 to 9). These genera may be referred to as the genera *Coniochaeta* etc. in this description. In some of the documents mentioned above, an amadoriase may also be referred to as, for example, ketoamine oxidase, fructosyl amino acid oxidase, fructosyl peptide oxidase, or fructosyl amine oxidase and the like.

Methods for rapidly and readily measuring HbA1c with the use of various types of amadoriases as described above include a method in which HbA1c is degraded with a cleavage enzyme such as a protease or peptidase (hereafter referred to as "protease(s) or the like"), and a particular target substance released from the β chain amino terminus of HbA1c is quantified with the use of amadoriases as described above is known (e.g., Patent Documents 1 to 7).

Specifically, a method is known in which HbA1c is degraded with a particular protease or the like, αFVH is released from the β chain amino terminus thereof, and the released αFVH is quantified.

According to a further method, HbA1c is digested using a protease, α-fructosyl hexapeptide (α-fructosyl-valyl-histidyl-leucyl-threonyl-prolyl-glutamic acid, hereafter referred to as "aF6P") is released, and the released aF6P is then quantified (e.g., Patent Documents 16 to 18). This method is an enzymatic method for measurement of HbA1c in line with the HbA1c measurement method defined by the International Federation of Clinical Chemistry and Laboratory Medicine (IFCC) (Non-Patent Document 10).

In addition, an amadoriase that directly oxidizes the β chain of HbA1 to generate hydrogen peroxide without the need of pretreatment with a protease as well as a method for measurement of HbA1c using the same have been reported (Patent Documents 20, 21, and 22). Such amadoriase can be referred to as "A1c oxidase (A1cOX)."

PRIOR ART DOCUMENTS

Patent Documents

Patent Document 1: WO 2004/104203
Patent Document 2: WO 2005/49857
Patent Document 3: JP 2001-95598 A
Patent Document 4: JP H05-33997 B (1993)
Patent Document 5: JP H11-127895 A (1999)
Patent Document 6: WO 97/13872
Patent Document 7: JP 2011-229526 A
Patent Document 8: JP 2003-235585 A
Patent Document 9: JP 2004-275013 A
Patent Document 10: JP 2004-275063 A
Patent Document 11: JP 2010-35469 A
Patent Document 12: JP 2010-57474 A
Patent Document 13: WO 2010/41715
Patent Document 14: WO 2010/41419
Patent Document 15: WO 2011/15325
Patent Document 16: WO 2004/38034
Patent Document 17: WO 2008/108385
Patent Document 18: WO 2013/162035
Patent Document 19: WO 2015/005257
Patent Document 20: WO 2015/060429
Patent Document 21: WO 2016/159384
Patent Document 22: WO 2015/005257
Patent Document 23: WO 2012/018094

Non-Patent Documents

Non-Patent Document 1: Biochem. Biophys. Res. Commun. 311, 104-11, 2003
Non-Patent Document 2: Biotechnol. Bioeng. 106, 358-66, 2010
Non-Patent Document 3: J. Biosci. Bioeng. 102, 241-3, 2006
Non-Patent Document 4: Appl. Microbiol. Biotechnol. 74, 813-9, 2007

Non-Patent Document 5: Eur. J. Biochem. 242, 499-505, 1996
Non-Patent Document 6: March Biotechnol. 6, 625-32, 2004
Non-Patent Document 7: Biosci. Biotechnol. Biochem. 66, 1256-61, 2002
Non-Patent Document 8: Biosci. Biotechnol. Biochem. 66, 2323-29, 2002
Non-Patent Document 9: Biotechnol. Letters 27, 27-32, 2005
Non-Patent Document 10: Jeppsson J O, et al, Approved IFCC reference method for the measurement of HbA1c in human blood, Clin. Chem. Lab. Med. 40, 78-89, 2002
Non-Patent Document 11: J. Biol. Chem., 283, 27007-27016, 2008
Non-Patent Document 12: Proteins, 84, 744-758, 2016

SUMMARY OF THE INVENTION

Objects to Be Attained by the Invention

The present inventor reported a method for measurement of HbA1c using an amadoriase that directly oxidizes the β chain of HbA1c to generate hydrogen peroxide without the need of pretreatment with a protease; i.e., A1cOX (Patent Documents 20 and 21). The present inventor conducted various tests using such enzyme and obtained findings showing that relative activity of A1cOX on hemoglobin C in which the α-amino group of Val at the N terminus of the β chain has been glycated (referred to as "HbC1c" herein) or on hemoglobin S in which the α-amino group of Val at the N terminus of the β chain is glycated (referred to as "HbS1c" herein) would be unexpectedly lower than activity on HbA1c.

That is, three types of α-fructosyl octapeptides (αF8P) indicated below were prepared as model substrates:
  α-fru-V-H-L-T-P-E-E-K (referred to as "HbA1c-type αF8P" herein);
  α-fru-V-H-L-T-P-V-E-K (referred to as "HbS1c-type αF8P" herein); and
  α-fru-V-H-L-T-P-K-E-K (referred to as "HbC1c-type αF8P" herein).

The term "HbA1c-type αF8P" refers to α-fructosyl-valyl-histidyl-leucyl-threonyl-prolyl-glutamyl-glutamyl-lysine, which is a glycated substrate corresponding to N-terminal 8 amino acids of HbA1c. In HbA1c-type αF8P, position 6 is glutamic acid (E6). In HbS1c-type αF8P, position 6 is valine (E6V mutation). In HbC1c-type αF8P, position 6 is lysine (E6K mutation). That is, in HbS1c-type αF8P and HbC1c-type αF8P, a mutation has occurred at position 6, and each mutation corresponds to HbS1c and HbC1c, respectively.

Relative activity of A1cOX on these substrates described above (10 μM) was compared and it was found that when activity on HbA1c-type αF8P is designated 100%, activity on HbS1c-type αF8P was 39%, and activity on HbC1c-type αF8P was 11%.

Hemoglobin S (HbS) is an inherited variant of hemoglobin A observed in some populations, and glutamic acid at the 6th position from the N terminus of the β chain of hemoglobin A (i.e., position 6 when valine at the N terminus is designated to be the position 1) is substituted with valine (E6V mutation). Further, hemoglobin C (HbC) is an inherited variant of hemoglobin A observed in some populations, and glutamic acid at the 6th position from the N terminus of the β chain of hemoglobin A (i.e., position 6 when valine at the N terminus is designated to be the position 1) is been substituted with lysine (E6K mutation). When glycated hemoglobin is measured using A1cOX with regard to subject having the HbS or HbC genotype, in view of the finding that relative activity of the αF8P substrate corresponding to the inherited hemoglobin is low, the measured value may be different from the true value.

Under such circumstances, the present inventor discovered a novel object, namely that it is necessary to provide a glycated hemoglobin oxidase that can react not only with HbA1c but also with the genotypes such as HbS1c or HbC1c. That is, it is an object of the present invention to provide a glycated hemoglobin oxidase that can act not only on HbA1c but also on HbS1c and/or HbC1c, and a method for measurement using the same.

Means for Attaining the Object

The present inventor carried out concentrated studies in order to attain the above objects. As a result, the present inventor found that by introducing a particular amino acid substitution into A1cOX, a modified amadoriase exhibiting improved relative activity on HbS1c and/or HbC1c, compared with activity on HbA1c could be obtained, thereby completing the present invention.

Specifically, the present invention encompasses the following.

[1] A method for measurement of HbS1c or HbC1c in a sample comprising a step of allowing glycated hemoglobin oxidase to act on a sample that can contain HbS1c or HbC1c.
[2] The method according to [1], wherein the amount of a reduced compound generated by the action of the glycated hemoglobin oxidase is measured.
[3] The method according to [2], wherein the reduced compound to be measured is hydrogen peroxide.
[4] The method according to any of [1] to [3], wherein the glycated hemoglobin oxidase has properties (a) and/or (b):
  (a) the ratio of activity on HbS1c-type αF8P to activity on HbA1c-type αF8P; i.e., the relative activity (HbS1c/HbA1c), is 0.45 or more; and
  (b) the ratio of activity on HbC1c-type αF8P to activity on HbA1c-type αF8P; i.e., the relative activity (HbC1c/HbA1c), is 0.15 or more.
[5] The method according to any of [1] to [4], wherein the glycated hemoglobin oxidase has an optimal pH range of 6 to 8, an operative pH range of 5 to 9, an optimal temperature range of 25° C. to 40° C., and a molecular weight of about 45 to 55 KDa on SDS-PAGE.
[6] The method according to any of [1] to [5], wherein the glycated hemoglobin oxidase is a glycated hemoglobin oxidase variant selected from the group consisting of (i) to (viii) below:
  (i) a glycated hemoglobin oxidase variant, wherein, when the amino acid sequence of the glycated hemoglobin oxidase is aligned with the amino acid sequence of SEQ ID NO: 1, the amino acid at the position corresponding to position 113 of the amino acid sequence of SEQ ID NO: 1 is modified into an amino acid selected from the group consisting of glutamic acid, aspartic acid, alanine, serine, threonine, asparagine, glutamine, cysteine, glycine, proline, valine, isoleucine, leucine, methionine, phenylalanine, tyrosine, and tryptophan;
  (ii) a glycated hemoglobin oxidase variant, wherein, when the amino acid sequence of the glycated hemoglobin oxidase is aligned with the amino acid sequence of SEQ ID NO: 1, the amino acid at the position corresponding to position 109 of the amino acid sequence of SEQ ID NO: 1 is modified into an amino acid selected from the group consisting of glutamic acid, alanine, aspartic acid, serine, threonine, asparagine, glutamine, cysteine, glycine, proline, valine, isoleucine, leucine, methionine, phenylalanine, tyrosine, and tryptophan;
(iii) a glycated hemoglobin oxidase variant, wherein, when the amino acid sequence of the glycated hemoglobin oxidase is aligned with the amino acid sequence of SEQ ID NO: 1, the amino acid at the position corresponding to position 106 of the amino acid sequence of SEQ ID NO: 1 is modified into an amino acid selected from the group consisting of glutamic acid, alanine, aspartic acid, serine, threonine, asparagine, glutamine, cysteine, glycine, proline, valine, isoleucine, leucine, methionine, phenylalanine, tyrosine, and tryptophan;
(iv) a glycated hemoglobin oxidase variant, wherein, when the amino acid sequence of the glycated hemoglobin oxidase is aligned with the amino acid sequence of SEQ ID NO: 1, the amino acid at the position corresponding to position 102 of the amino acid sequence of SEQ ID NO: 1 is modified into an amino acid selected from the group consisting of alanine, aspartic acid, glutamic acid, serine, threonine, asparagine, glutamine, cysteine, glycine, proline, valine, isoleucine, leucine, methionine, phenylalanine, tyrosine, and tryptophan;
(v) the glycated hemoglobin oxidase variant as defined in (i), (ii), (iii), or (iv) comprising an amino acid sequence having a substitution, deletion, or addition of 1 or several amino acids at positions other than those corresponding to positions 113, 109, 106, and 102 of the amino acid sequence of SEQ ID NO: 1;
(vi) the glycated hemoglobin oxidase variant as defined in (i), (ii), (iii), or (iv) comprising an amino acid sequence having 70% or higher sequence identity with the amino acid sequence of SEQ ID NO: 1 or SEQ ID NO: 45 over the full length, wherein the amino acid at the position corresponding to position 60 of SEQ ID NO: 1 is glycine, the amino acid at the position corresponding to position 239 of SEQ ID NO: 1 is tryptophan, phenylalanine, or tyrosine, the amino acid at the position corresponding to position 282 of SEQ ID NO: 1 is glutamic acid, the amino acid at the position corresponding to position 376 of SEQ ID NO: 1 is glycine, the amino acid at the position corresponding to position 418 of SEQ ID NO: 1 is arginine, and the amino acid sequence of the positions corresponding to positions 15 to 20 of SEQ ID NO: 1 is Gly-Xaa-Gly-Xaa-Xaa-Gly, wherein Xaa indicates any amino acid;
(vii) the glycated hemoglobin oxidase variant as defined in (i), (ii), (iii), or (iv) comprising an amino acid sequence having 70% or higher sequence identity with the amino acid sequence of SEQ ID NO: 1 or SEQ ID NO: 45 over the full length and having 90% or higher sequence identity between the amino acid sequence of the homologous region of SEQ ID NO: 1 or SEQ ID NO: 45 and the amino acid sequence of the homologous region of the corresponding positions of the glycated hemoglobin oxidase; and
(viii) the glycated hemoglobin oxidase variant as defined in (i), (ii), (iii), or (iv) comprising an amino acid sequence having 50% or higher sequence identity with the amino acid sequence of SEQ ID NO: 1 or SEQ ID NO: 45 over the full length and having 70% or higher sequence identity between the amino acid sequence of a homologous region of SEQ ID NO: 1 or SEQ ID NO: 45 and the amino acid sequence of a homologous region of the corresponding positions of the glycated hemoglobin oxidase, wherein the amino acid at the position corresponding to position 60 of SEQ ID NO: 1 is glycine, the amino acid at the position corresponding to position 239 of SEQ ID NO: 1 is tryptophan, phenylalanine, or tyrosine, the amino acid at the position corresponding to position 282 of SEQ ID NO: 1 is glutamic acid, the amino acid at the position corresponding to position 376 of SEQ ID NO: 1 is glycine, the amino acid at the position corresponding to position 418 of SEQ ID NO: 1 is arginine, and the amino acid sequence of the positions corresponding to positions 15 to 20 of SEQ ID NO: 1 is Gly-Xaa-Gly-Xaa-Xaa-Gly, wherein Xaa indicates any amino acid.

[7] Glycated hemoglobin oxidase for measurement of HbS1c or HbC1c in a sample.

[8] The glycated hemoglobin oxidase according to [7], which is allowed to act on HbS1c or HbC1c and used to measure the amount of the reduced compound generated.

[9] The glycated hemoglobin oxidase according to [8], wherein the reduced compound generated is hydrogen peroxide.

[10] The glycated hemoglobin oxidase according to any of [7] to [9], which has properties (a) and/or (b):
(a) the ratio of activity on HbS1c-type αF8P to activity on HbA1c-type αF8P; i.e., the relative activity (HbS1c/HbA1c), is 0.45 or more; and
(b) the ratio of activity on HbC1c-type αF8P to activity on HbA1c-type αF8P; i.e., the relative activity (HbC1c/HbA1c), is 0.15 or more.

[11] The glycated hemoglobin oxidase according to any of [7] to [10], which has an optimal pH range of 6 to 8, an operative pH range of 5 to 9, an optimal temperature range of 25° C. to 40° C., and a molecular weight of about 45 to 55 KDa on SDS-PAGE.

[12] The glycated hemoglobin oxidase according to any of [7] to [11], which is selected from the group consisting of (i) to (viii) below:
(i) a glycated hemoglobin oxidase variant, wherein, when the amino acid sequence of the glycated hemoglobin oxidase is aligned with the amino acid sequence of SEQ ID NO: 1, the amino acid at the position corresponding to position 113 of the amino acid sequence of SEQ ID NO: 1 is modified into an amino acid selected from the group consisting of glutamic acid, aspartic acid, alanine, serine, threonine, asparagine, glutamine, cysteine, glycine, proline, valine, isoleucine, leucine, methionine, phenylalanine, tyrosine, and tryptophan;
(ii) a glycated hemoglobin oxidase variant, wherein, when the amino acid sequence of the glycated hemoglobin oxidase is aligned with the amino acid sequence of SEQ ID NO: 1, the amino acid at the position corresponding to position 109 of the amino acid sequence of SEQ ID NO: 1 is modified into an amino acid selected from the group consisting of glutamic acid, alanine, aspartic acid, serine, threonine, asparagine, glutamine, cysteine, glycine, proline, valine, isoleucine, leucine, methionine, phenylalanine, tyrosine, and tryptophan;
(iii) a glycated hemoglobin oxidase variant, wherein, when the amino acid sequence of the glycated hemoglobin oxidase is aligned with the amino acid sequence of SEQ ID NO: 1, the amino acid at the position corresponding to position 106 of the amino acid sequence of SEQ ID NO: 1 is modified into an amino acid selected from the group consisting of glutamic acid, alanine, aspartic acid, serine, threonine, asparagine, glutamine, cysteine, glycine, proline, valine, isoleucine, leucine, methionine, phenylalanine, tyrosine, and tryptophan;

(iv) a glycated hemoglobin oxidase variant, wherein, when the amino acid sequence of the glycated hemoglobin oxidase is aligned with the amino acid sequence of SEQ ID NO: 1, the amino acid at the position corresponding to position 102 of the amino acid sequence of SEQ ID NO: 1 is modified into an amino acid selected from the group consisting of alanine, aspartic acid, glutamic acid, serine, threonine, asparagine, glutamine, cysteine, glycine, proline, valine, isoleucine, leucine, methionine, phenylalanine, tyrosine, and tryptophan;

(v) the glycated hemoglobin oxidase variant as defined in (i), (ii), (iii), or (iv) comprising an amino acid sequence having a substitution, deletion, or addition of 1 or several amino acids at positions other than those corresponding to positions 113, 109, 106, and 102 of the amino acid sequence of SEQ ID NO: 1;

(vi) the glycated hemoglobin oxidase variant as defined in (i), (ii), (iii), or (iv) comprising an amino acid sequence having 70% or higher sequence identity with the amino acid sequence of SEQ ID NO: 1 or SEQ ID NO: 45 over the full length, wherein the amino acid at the position corresponding to position 60 of SEQ ID NO: 1 is glycine, the amino acid at the position corresponding to position 239 of SEQ ID NO: 1 is tryptophan, phenylalanine, or tyrosine, the amino acid at the position corresponding to position 282 of SEQ ID NO: 1 is glutamic acid, the amino acid at the position corresponding to position 376 of SEQ ID NO: 1 is glycine, the amino acid at the position corresponding to position 418 of SEQ ID NO: 1 is arginine, and the amino acid sequence of the positions corresponding to positions 15 to 20 of SEQ ID NO: 1 is Gly-Xaa-Gly-Xaa-Xaa-Gly, wherein Xaa indicates any amino acid;

(vii) the glycated hemoglobin oxidase variant as defined in (i), (ii), (iii), or (iv) comprising an amino acid sequence having 70% or higher sequence identity with the amino acid sequence of SEQ ID NO: 1 or SEQ ID NO: 45 over the full length and having 90% or higher sequence identity between the amino acid sequence of the homologous region of SEQ ID NO: 1 or SEQ ID NO: 45 and the amino acid sequence of the homologous region of the corresponding positions of the glycated hemoglobin oxidase; and (viii) the glycated hemoglobin oxidase variant as defined in (i), (ii), (iii), or (iv) comprising an amino acid sequence having 50% or higher sequence identity with the amino acid sequence of SEQ ID NO: 1 or SEQ ID NO: 45 over the full length and having 70% or higher sequence identity between the amino acid sequence of a homologous region of SEQ ID NO: 1 or SEQ ID NO: 45 and the amino acid sequence of a homologous region of the corresponding positions of the glycated hemoglobin oxidase, wherein the amino acid at the position corresponding to position 60 of SEQ ID NO: 1 is glycine, the amino acid at the position corresponding to position 239 of SEQ ID NO: 1 is tryptophan, phenylalanine, or tyrosine, the amino acid at the position corresponding to position 282 of SEQ ID NO: 1 is glutamic acid, the amino acid at the position corresponding to position 376 of SEQ ID NO: 1 is glycine, the amino acid at the position corresponding to position 418 of SEQ ID NO: 1 is arginine, and the amino acid sequence of the positions corresponding to positions 15 to 20 of SEQ ID NO: 1 is Gly-Xaa-Gly-Xaa-Xaa-Gly, wherein Xaa indicates any amino acid.

[13] The glycated hemoglobin oxidase according to any of [7] to [12], based on an amadoriase of the genus *Coniochaeta, Eupenicillium, Pyrenochaeta, Arthrinium, Curvularia, Neocosmospora, Cryptococcus, Phaeosphaeria, Aspergillus, Emericella, Ulocladium*, or *Penicillium*.

[14] The glycated hemoglobin oxidase according to [13], wherein the amadoriase is derived from *Coniochaeta* sp., *Eupenicillium terrenum, Pyrenochaeta* sp., *Arthrinium* sp., *Curvularia clavata, Neocosmospora vasinfecta, Cryptococcus neoformans, Phaeosphaeria nodorum, Aspergillus nidulans, Emericella nidulans, Ulocladium* sp., *Penicillium* janthinelum, or *Penicillium chrysogenum*.

[15] A reagent composition for measurement of HbS1c or HbC1c comprising the glycated hemoglobin oxidase according to any of [7] to [14].

[16] A gene encoding the glycated hemoglobin oxidase according to any of [7] to [14].

[17] A vector comprising the gene according to [16].

[18] A host cell comprising the vector according to [17].

[19] A method for producing glycated hemoglobin oxidase comprising the following steps:
   (i) culturing the host cell according to [18] under conditions where the glycated hemoglobin oxidase can be expressed; and
   (ii) isolating the glycated hemoglobin oxidase from a culture product or culture solution.

[20] A method for producing glycated hemoglobin oxidase by modifying an amadoriase or A1c oxidase comprising the following steps:
   (i) obtaining an amadoriase gene or A1c oxidase gene;
   (ii) integrating the amadoriase gene or A1c oxidase gene into a vector, transforming a host cell, expressing the amadoriase or A1c oxidase, and isolating the expressed product;
   (iii) measuring the relative activity (HbS1c/HbA1c) and/or the relative activity (HbC1c/HbA1c) of the expressed product;
   (iv) modifying the amadoriase gene or A1c oxidase gene such that, when the amino acid sequence of the amadoriase or A1c oxidase is aligned with the amino acid sequence of SEQ ID NO: 1, the amino acid at the position corresponding to position 113, 109, 106, or 102 of the amino acid sequence of SEQ ID NO: 1 is modified into an amino acid selected from the group consisting of glutamic acid, aspartic acid, alanine, serine, threonine, asparagine, glutamine, cysteine, glycine, proline, valine, isoleucine, leucine, methionine, phenylalanine, tyrosine, and tryptophan;
   (v) integrating the modified gene into a vector, transforming a host cell, expressing the modified amadoriase or A1c oxidase, and isolating the expressed product;
   (vi) measuring the relative activity (HbS1c/HbA1c) and/or the relative activity (HbC1c/HbA1c) of the expressed product of the modified amadoriase or A1c oxidase and comparing the measured values with the values measured in step (iii);
   (vii) when the relative activity (HbS1c/HbA1c) of the modified amadoriase or A1c oxidase is 1.1 times or greater than the relative activity (HbS1c/HbA1c) of the amadoriase or A1c oxidase before modification and/or the relative activity (HbC1c/HbA1c) of the modified amadoriase or A1c oxidase is 1.1 times or greater than the relative activity (HbC1c/HbA1c) of the amadoriase or A1c oxidase before modification, designating the modified amadoriase or A1c oxidase as the glycated hemoglobin oxidase; and (viii) repeating steps (iv) to (vi) on the glycated hemoglobin oxidase of step (vii), according to need.

The present specification encompasses the contents described in the description and/or drawings of Japanese Patent Application No. 2017-167890, which is a priority document of the present application.

Effects of the Invention

The present invention provides a glycated hemoglobin oxidase that recognizes not only HbA1c but also glycated hemoglobins of genotypes such as HbS1c and HbC1c. Such enzyme can be used for a reagent for measurement of glycated hemoglobin that can be applied to various genotypes.

BRIEF DESCRIPTION OF THE DRAWINGS

FIG. 1-1 is a first diagram showing amino acid sequence identity among various known amadoriases. In addition to Co (*Coniochaeta* sp.), Et (*Eupenicillium terrenum*), Py (*Pyrenochaeta* sp.), Ar (*Arthrinium* sp.), Cc (*Curvularia clavata*), and Nv (*Neocosmospora vasinfecta*), Cn (*Cryptococcus neoformans*), Pn (*Phaeosphaeria nodorum*), An (*Aspergillus nidulans*), En (*Emericella nidulans*), Ul (*Ulocladium* sp.), and Pj (*Penicillium janthinelum*) are aligned.

FIG. 1-2 is continued from FIG. 1-1.
FIG. 1-3 is continued from FIG. 1-2.
FIG. 1-4 is continued from FIG. 1-3.
FIG. 1-5 is continued from FIG. 1-4.

FIG. 2-1 is a diagram showing amino acid sequence identity and similar amino acids among various known amadoriases. In addition to the amadoriases shown in FIG. 1, Ao2, Af2, At, Fo, Ao1, Af1, Pi, and Dh were aligned.

FIG. 2-2 is continued from FIG. 2-1.
FIG. 2-3 is continued from FIG. 2-2.
FIG. 2-4 is continued from FIG. 2-3.
FIG. 2-5 is continued from FIG. 2-4.
FIG. 2-6 is continued from FIG. 2-5.
FIG. 2-7 is continued from FIG. 2-6.
FIG. 2-8 is continued from FIG. 2-7.
FIG. 2-9 is continued from FIG. 2-8.
FIG. 2-10 is continued from FIG. 2-9.

EMBODIMENTS FOR CARRYING OUT THE INVENTION

The present invention is described in detail as follows.
(Glycated Hemoglobin, Hemoglobin A1c, Glycated HbS, and Glycated HbC)

Examples of hemoglobin include, hemoglobin A (HbA) as normal hemoglobin, as well as abnormal hemoglobin, such as hemoglobin S (HbS) and hemoglobin C (HbC). The term "glycated hemoglobin" used herein refers to non-enzymatically glycated hemoglobin. The term "glycated hemoglobin" used herein encompasses not only glycated HbA but also glycated abnormal hemoglobin, such as glycated HbS and glycated HbC. Glycated hemoglobin is present in, for example, the blood in vivo. Among various types of glycated hemoglobin, in particular, glycated hemoglobin in which valine at the N-terminus of the HbA β chain is glycated is referred to as "hemoglobin A1c (HbA1c)." Various types of glycated HbS or HbC may be present depending on a type of sugar bound to the β chain. For the convenience of description, the term "glycated HbS" used herein refers to glycated HbS in which valine at the amino terminus of the HbS β chain is glycated (which may also be referred to as "HbS1c"), unless otherwise specified. Further, the term "glycated HbC" used herein refers to glycated HbC in which valine at the amino terminus of the HbC β chain is glycated (which may also be referred to as "HbC1c"), unless otherwise specified.

(Glycated Peptide and Fructosyl Peptide)

The term "glycated peptide" used herein refers to a non-enzymatically-glycated peptide derived from a glycated protein and this includes peptides that are directly and non-enzymatically glycated, products of degradation of glycated proteins by a protease or the like, and products of glycation of (poly)peptides constituting glycated proteins are included in glycated peptides. A "glycated peptide" may also be referred to as a "fructosyl peptide." Regarding glycated proteins, examples of amino groups in the glycated peptide side chain include an amino terminal α-amino group and a ε-amino group in the lysine side chain within a peptide. In the present invention, however, the glycated peptide is, more specifically, an α-glycated peptide in which an α-amino group is glycated (α-fructosyl peptide).

(Substrate Specificity)

The glycated hemoglobin oxidase of the present invention acts directly on HbA1c and more specifically, on the β chain of HbA1c. The phrase glycated hemoglobin oxidase acts directly means an amadoriase acts on the fructosyl group at the N-terminus of the β chain of the glycated hemoglobin in the presence of oxygen, and 2-keto-D-glucose, hydrogen peroxide, and hemoglobin β chain are generated. In addition, the glycated hemoglobin oxidase of the present invention acts on HbA1c-type αF8P. More significantly, the glycated hemoglobin oxidase of the present invention acts not only on HbA1c-type αF8P but also on HbS1c-type αF8P and/or HbC1c-type αF8P. Since it is known that amadoriase that acts on HbA1c-type αF8P also acts on HbA1c (Patent Document 21), it is rationally considered that the glycated hemoglobin oxidase of the present invention acts not only on HbA1c but also on glycated HbS and/or glycated HbC. That is, in one embodiment, the glycated hemoglobin oxidase of the present invention acts not only on HbA1c but also on glycated HbS and/or Glycated HbC.

(Relative activity of glycated hemoglobin oxidase variant)

In one embodiment, the glycated hemoglobin oxidase variant of the present invention has improved relative activity on HbS1c-type αF8P, compared with the A1c oxidase before modification. The term "relative activity on HbS1c-type αF8P" refers to the ratio of activity on HbS1c-type αF8P to activity on HbA1c-type αF8P (normal αF8P), that is, activity on HbS1c-type αF8P/activity on HbA1c-type αF8P, when the enzyme amount and reaction conditions are maintained constant. For the convenience of description, activity on HbS1c-type αF8P/activity on HbA1c-type αF8P may be referred to herein as relative activity (HbS1c/HbA1c).

In one embodiment, the glycated hemoglobin oxidase variant of the present invention has improved relative activity on HbC1c-type αF8P, compared with the A1c oxidase before modification. The term "relative activity on HbC1c-type αF8P" refers to the ratio of activity on HbC1c-type αF8P to activity on HbA1c-type αF8P, that is, activity on HbC1c-type αF8P/activity on HbA1c-type αF8P, when the enzyme amount and the reaction conditions are maintained constant. For the convenience of description, activity on HbC1c-type αF8P/activity on HbA1c-type αF8P may be referred to herein as relative activity (HbC1c/HbA1c).

That is, the glycated hemoglobin oxidase variant of the present invention has enhanced relative activity (HbS1c/HbA1c) and/or relative activity (HbC1c/HbA1c), compared with the A1c oxidase before modification. Incidentally, while the relative activity is defined herein with reference to the model substrate αF8P, this is merely for the convenience of description and it is rationally considered that such feature is applicable to relative activity on various types of glycated hemoglobins as well.

In one embodiment, the glycated hemoglobin oxidase variant of the present invention may have the relative activity (HbS1c/HbA1c) that is, for example, 1.1 times, 1.2 times, 1.3 times, 1.4 times, 1.5 times, 2.0 times, 2.5 times, or for example 2.6 times or greater than the relative activity (HbS1c/HbA1c) of the amadoriase before modification. For example, when the relative activity (HbS1c/HbA1c) of A1cOX before modification is 0.39 and the relative activity (HbS1c/HbA1c) of the glycated hemoglobin oxidase after modification is 0.77, then the relative activity (HbS1c/HbA1c) after modification is about 1.97 times greater than that before modification.

In one embodiment, the glycated hemoglobin oxidase variant of the present invention may have the relative activity (HbC1c/HbA1c) that is, for example, 1.1 times, 1.2 times, 1.3 times, 1.4 times, 1.5 times, 2.0 times, 2.5 times, 3.0 times, 4.0 times, 5.0 times, 6.0 times, 7.0 times, 8.0 times, or for example 8.3 times or greater than the relative activity (HbC1c/HbA1c) of the amadoriase before modification. For example, when the relative activity (HbC1c/HbA1c) of A1cOX before modification is 0.11 and the relative activity (HbC1c/HbA1c) of the glycated hemoglobin oxidase after modification is 0.91, then the relative activity (HbS1c/HbA1c) after modification is about 8.3 times greater than that before modification.

In one embodiment, the glycated hemoglobin oxidase of the present invention may have the relative activity (HbS1c/HbA1c) that is, for example, 0.4 or greater, 0.41 or greater, 0.42 or greater, 0.43 or greater, 0.44 or greater, 0.45 or greater, 0.5 or greater, 0.55 or greater, 0.6 or greater, 0.65 or greater, 0.7 or greater, 0.75 or greater, 0.8 or greater, 0.85 or greater, 0.9 or greater, or for example 0.95 or greater. In one embodiment, the glycated hemoglobin oxidase of the present invention may have the relative activity (HbC1c/HbA1c) that is, for example, 0.10 or greater, 0.11 or greater, 0.12 or greater, 0.13 or greater, 0.14 or greater, 0.15 or greater, 0.16 or greater, 0.17 or greater, 0.18 or greater, 0.19 or greater, 0.2 or greater, 0.25 or greater, 0.3 or greater, 0.35 or greater, 0.4 or greater, 0.5 or greater, 0.6 or greater, 0.7 or greater, 0.8 or greater, or for example 0.9 or greater.

The glycated hemoglobin oxidase variant of the present invention not only acts on HbA1c but also has enhanced relative activity (HbS1c/HbA1c) and/or relative activity (HbC1c/HbA1c) and, therefore, can be used for measurement of a sample containing glycated HbS or glycated HbC, and the problem of deviation occurring between the measured value and the true value can be avoided.

In one embodiment, the glycated hemoglobin oxidase of the present invention is capable of accurately measuring glycated hemoglobin in a sample, and does not cause a deviation (discrepancy) between the measured value and the true value. In one embodiment, the phrase no deviation (discrepancy) between the measured value and the true value refers to the measured value not being less than 90 (an arbitrary unit) or over 110 when the level of glycated hemoglobin that is actually contained in the sample is 100 (an arbitrary unit).

(Amadoriase)

An amadoriase is also referred to as ketoamine oxidase, fructosyl amino acid oxidase, fructosyl peptide oxidase, or fructosyl amine oxidase, and is an enzyme that catalyzes a chemical reaction that oxidizes iminodiacetic acid or a derivative thereof (Amadori compound) in the presence of oxygen to generate glyoxylic acid or α-ketoaldehyde, an amino acid or peptide, and hydrogen peroxide. Amadoriases are widely distributed in nature and can be obtained by searching for enzymes from sources of microorganisms, animals, or plants. With regard to microorganisms, amadoriases can be obtained from, for example, filamentous fungi, yeast, or bacteria.

An amadoriase can be obtained from microorganisms of the genera, for example, *Coniochaeta*, *Eupenicillium*, *Pyrenochaeta*, *Arthrinium*, *Curvularia*, *Neocosmospora*, *Cryptococcus*, *Phaeosphaeria*, *Aspergillus*, *Emericella*, *Ulocladium*, *Penicillium*, *Fusarium*, *Achaetomiella*, *Achaetomium*, *Thielavia*, *Chaetomium*, *Gelasinospora*, *Microascus*, *Leptosphaeria*, *Ophiobolus*, *Pleospora*, *Coniochaetidium*, *Pichia*, *Corynebacterium*, *Agrobacterium*, or *Arthrobacter*.

(Obtaining a Gene Encoding an Amadoriase)

In order to obtain a gene encoding an amadoriase (hereinafter, also referred to simply as "amadoriase gene"), common gene cloning methods can be employed. For example, chromosomal DNA or mRNA can be extracted from a microorganism fungus body or various cells having an ability to produce an amadoriase by a conventional technique, such as a method described in "Current Protocols in Molecular Biology" (WILEY Interscience, 1989). In addition, cDNA can be synthesized using mRNA as the template. A chromosomal DNA or cDNA library can be made using the chromosomal DNA or cDNA obtained in such a manner.

Subsequently, DNA including the entire sequence of a target amadoriase gene can be obtained by a method of synthesizing an appropriate probe DNA based on the amino acid sequence of the amadoriase mentioned above and selecting an amadoriase gene from a chromosomal DNA or cDNA library using the probe DNA. Alternatively, an appropriate primer DNA may be produced based on the amino acid sequence mentioned above, a DNA including the target gene fragment encoding the amadoriase may be amplified by using an appropriate polymerase chain reaction (PCR) technique, such as the 5' RACE or 3' RACE method, and the resulting DNA fragments may then be linked.

An example of an amadoriase gene is an amadoriase gene derived from the genus *Coniochaeta* (JP 2003-235585 A). Other examples include amadoriase genes derived from the genus *Phaeosphaeria*, amadoriase genes derived from the genus *Neocosmospora*, amadoriase genes derived from the genus *Aspergillus*, amadoriase genes derived from the genus *Cryptococcus*, amadoriase genes derived from the genus *Curvularia*, and amadoriase genes derived from the genus *Eupenicillium*.

An amadoriase gene may be linked to a vector. Any vector, such as a plasmid, bacteriophage, or cosmid vector can be used, and an example thereof is pBluescriptII SK+ (manufactured by Stratagene Corporation). The amadoriase gene derived from the strain *Coniochaeta* sp. NISL 9330 and the plasmid comprising the same are disclosed in WO 2007/125779. The amadoriase gene derived from the strain *Eupenicillium* terrenum ATCC 18547 and the plasmid comprising the same are disclosed in WO 2007/125779. The amadoriase gene derived from the strain *Aspergillus nidulans* FGSC A26 and the plasmid comprising the same are disclosed in WO 2012/018094. The amadoriase gene derived from a strain of *Cryptococcus neoformans* and the plasmid comprising the same are disclosed in WO 2012/018094. The amadoriase gene derived from a strain of *Neocosmospora vasinfecta* and the plasmid comprising the same are disclosed in WO 2012/018094. A plasmid may be obtained in accordance with conventional techniques. For example, a plasmid comprising an amadoriase gene can be extracted and purified with the use of the GenElute Plasmid Miniprep Kit (manufactured by Sigma-Aldrich). For example, the obtained amadoriase gene may be subjected to engineering to prepare an A1cOX gene or a purified enzyme can be obtained therefrom with reference to the teaching of Patent Documents 20 to 22.

(Mutation Treatment of Amadoriase Gene)

Mutation treatment of an amadoriase gene can be performed by any known method depending on the intended form of mutation. More specifically, a method of bringing a chemical mutagen into contact with and allowing to act on an amadoriase gene or recombinant DNA comprising such gene integrated therein, an ultraviolet irradiation method, a genetic engineering technique, a method of making full use of a protein engineering technique, or various other methods can be extensively used.

Examples of chemical mutagens used in the mutation mentioned above include hydroxylamine, N-methyl-N'-nitro-N-nitrosoguanidine, nitrous acid, sulfurous acid, hydrazine, formic acid, and 5-bromouracil.

Various conditions for the contact/reactions may be employed depending on the type of a drug to be used, and such conditions are not particularly limited where a desired mutation can be actually induced in an amadoriase gene. In general, the desired mutation can be induced by contact/reactions performed at 20° C. to 80° C. for 10 minutes or longer, and preferably 10 to 180 minutes, with the use of the drug mentioned above at the concentration of 0.5 M to 12 M. The ultraviolet irradiation may be also performed according to a conventional technique as described above (Gendai Kagaku, pp. 24-30, June, 1989).

As a method making extensive use of protein engineering techniques, in general, a technique known as site-specific mutagenesis can be used. Examples include the Kramer method (Nucleic Acids Res., 12, 9441, 1984; Methods Enzymol., 154, 350, 1987; Gene, 37, 73, 1985), the Eckstein method (Nucleic Acids Res., 13, 8749, 1985; Nucleic Acids Res., 13, 8765, 1985; Nucleic Acids Res, 14, 9679, 1986), and the Kunkel method (Proc. Natl. Acid. Sci. U.S.A., 82, 488, 1985; Methods Enzymol., 154, 367, 1987).

A general PCR technique can also be used (Technique, 1, 11, 1989). In addition to the conventional genetic mutation technique, the modified amadoriase genes of interest or the glycated hemoglobin oxidase gene can be directly synthesized by an organic synthesis method or an enzyme synthesis method.

The nucleotide sequences of the amadoriase genes may be verified by, for example, using a multi-capillary DNA analysis system or Applied Biosystems 3130x Genetic Analyzer (Life Technologies).

(Transformation/Transduction)

The amadoriase gene can be integrated into a vector such as a bacteriophage vector, a cosmid vector, or a plasmid vector used in transformation of a procaryotic or eucaryotic cell by conventional techniques. With the use thereof, a host corresponding to each vector can be transformed or transduced by conventional techniques. Examples of hosts of E. coli include, but are not limited to, various strains of E. coli, such as a K-12 strain, a JM109 strain (Takara Bio Inc.), and an DH5a strain (Takara Bio Inc.).

(A1cOX)

Among amadoriases, those that act directly on HbA1c may be referred to as "A1c oxidase (A1cOX)." An A1cOX gene can be prepared from the amadoriase gene described above based on the teaching of Patent Documents 20 to 22. Genes equivalent thereto can also be utilized in the present invention.

For example, Patent Documents 20 and 21 disclose A1cOX based on the amadoriase derived from Coniochaeta sp. NISL 9330 (SEQ ID NO: 1). Patent Document 21 discloses A1cOX having high specific activity on αF8P. The descriptions thereof are incorporated herein by reference in their entirety. The table below shows the mutations that A1cOX can have and the positions thereof. In the table, the amino acid (one letter code) at the left of the indicated position is the wild-type amino acid and the amino acid at the right is the amino acid after substitution. When a plurality of amino acids are disclosed as amino acids after substitution, candidates are separated by commas.

TABLE 1

| | WO 2015/060429 | WO 2016/159384 |
|---|---|---|
| | | Name |
| | A1cOX (CFP-T7 variants) | A1cOX (CFP-T7 variants) |
| | | Origin |
| | Coniochaeta sp. | Coniochaeta sp. |
| | | SEQ ID NO |
| aa position | SEQ 1 | SEQ 1 |
| 62 | R62(A, N, D, Q, E, G, V, L, I, C, S, T, P) | R62(A, N, D, Q, E, G, V, L, I, C, S, M, T, P) |
| 63 | L63(H, A) | L63(H, A, G) |
| 102 | E102(K) | E102(K) |
| 106 | D106(A, K, R) | D106(A, K, R) |
| 110 | Q110(L, Y) | Q110(L, Y, F, H) |
| 113 | A113(K, R) | A113(K, R) |
| 355 | A355(S) | A355(S) |
| 419 | A419(K) | A419(K) |
| 68 | D68(N) | D68(N) |
| 356 | A356(T) | A356(T) |
| 64 | | R64(G, S, M, L, T, V, I) |
| 99 | | H99(S) |

Positions in the sequences of amadoriases of other origins that correspond to positions 62, 63, 102, 106, 110, 113, 355, 419, 68, 356, 64, and 99 of SEQ ID NO: 1 are as shown in the table below. Corresponding positions will be explained elswhere.

TABLE 2

| | Name | | | | | |
|---|---|---|---|---|---|---|
| | CFP-T7 | EFP-T5 | PyFX | ArFX | CcFX | NvFX |
| | | | Origin | | | |
| | Coniochaeta sp. | E. terrenum | Pyrenochaeta sp. | Arthrinium sp. | C. clavata | N. vasinfecta |
| aa | | | SEQ ID NO | | | |
| position | SEQ 1 | SEQ 3 | SEQ 4 | SEQ 5 | SEQ 6 | SEQ 7 |
| 62 | R62 | R62 | R62 | R62 | R62 | R62 |
| 63 | L63 | L63 | L63 | L63 | L63 | L63 |
| 102 | E102 | E102 | K102 | K102 | E102 | E102 |
| 106 | D106 | N106 | D106 | A106 | D106 | G106 |
| 110 | Q110 | K110 | A110 | Q110 | A110 | E110 |

TABLE 2-continued

| | | | | | | |
|---|---|---|---|---|---|---|
| 113 | A113 | T113 | T113 | T113 | A113 | K113 |
| 355 | A355 | A355 | A353 | A356 | A353 | S355 |
| 419 | A419 | G419 | A418 | A421 | A418 | A420 |
| 68 | D68 | D68 | D68 | D68 | D68 | D68 |
| 356 | A356 | N356 | A354 | A357 | A354 | A356 |
| 64 | R64 | R64 | R64 | R64 | R64 | R64 |
| 99 | H99 | S99 | H99 | G99 | H99 | S99 |

| | Name | | | | | |
|---|---|---|---|---|---|---|
| | CnFX | PnFX | AnFX | EnFX | UlFX | PjFX |
| | | | | Origin | | |
| aa | C. neoformans | P. nodorum | A. nidulans | E. nidulans | Ulocladium sp. | P. janthinellum |
| | | | | SEQ ID NO | | |
| position | SEQ 8 | SEQ 9 | SEQ 10 | SEQ 11 | SEQ 12 | SEQ 13 |
| 62 | R62 | S62 | R61 | R61 | R62 | R62 |
| 63 | I63 | L63 | L62 | L62 | L63 | L63 |
| 102 | E102 | K102 | E101 | E101 | K102 | E102 |
| 106 | S106 | D106 | G105 | K105 | D106 | S106 |
| 110 | S110 | G110 | K109 | R109 | A110 | K110 |
| 113 | A113 | A113 | S112 | S112 | A113 | D113 |
| 355 | A355 | A351 | A355 | A355 | A353 | A355 |
| 419 | A420 | S416 | A420 | A420 | A418 | S419 |
| 68 | D68 | D68 | D67 | D67 | D68 | D68 |
| 356 | N356 | A352 | N356 | N356 | A354 | N356 |
| 64 | R64 | R64 | R63 | R63 | R64 | R64 |
| 99 | H99 | H99 | S98 | S98 | H99 | S99 |

TABLE 3

| | Name | | | | | | | |
|---|---|---|---|---|---|---|---|---|
| | CFP-T7 | Ao2 | Af2 | At | Fo | Ao1 | Af1 | Pi | Dh |
| | | | | | Origin | | | | |
| aa | Coniochaeta sp. | A. oryzae | A. fumigatus | A. terreus | F. oxysporum | A. oryzae | A. fumigatus | Pichia sp. | D. hansenii |
| | | | | | SEQ ID NO | | | | |
| position | SEQ 1 | SEQ 14 | SEQ 15 | SEQ 16 | SEQ 17 | SEQ 18 | SEQ 19 | SEQ 20 | SEQ 21 |
| 62 | R62 | G58 | G58 | G58 | L59 | R61 | S61 | D53 | T56 |
| 63 | L63 | Q59 | Q59 | Q59 | S60 | E62 | E62 | Y54 | S57 |
| 102 | E102 | A104 | E104 | E104 | K107 | S109 | A109 | A98 | E96 |
| 106 | D106 | R108 | R108 | R108 | Q111 | H113 | H113 | H102 | S100 |
| 110 | Q110 | R112 | R112 | R112 | D115 | H117 | D117 | Y106 | R104 |
| 113 | A113 | P115 | P115 | P115 | G118 | D120 | E109 | Y107 | |
| 355 | A355 | R341 | R343 | R342 | R347 | R350 | R350 | M332 | R332 |
| 419 | A419 | F410 | F412 | F411 | F416 | F419 | F419 | W400 | Y404 |
| 68 | D68 | K64 | K64 | K64 | K65 | E67 | S67 | A59 | — |
| 356 | A356 | E342 | E344 | E343 | M348 | A351 | A351 | Q333 | H333 |
| 64 | R64 | Y60 | Y60 | Y60 | T61 | V63 | L63 | V55 | D58 |
| 99 | H99 | C101 | C101 | T101 | S104 | H106 | H106 | S95 | T93 |

Further, Patent Document 22 discloses a variant based on the amadoriase derived from *Emericella nidulans* (FPDX). The descriptions thereof are incorporated herein by reference in their entirety. The table below shows the mutations that the FPDX variant can have and the positions thereof. In the table, the positions shown in the left column indicate the positions corresponding to SEQ ID NO: 1 herein, and the positions shown in the right column indicate the corresponding positions of the amadoriase. In the table, the amino acid at the left of the indicated position is the wild-type amino acid and the amino acid at the right is the amino acid after substitution. When a plurality of amino acids are disclosed as amino acids after substitution, candidates are separated by commas.

TABLE 4

| | WO 2015/005257 |
|---|---|
| | Name |
| | FPOX variants |
| | Origin |
| | *Emericella nidulans* |
| | SEQ ID NO |
| aa position | SEQ 11 |
| 62 | R61(S) |
| 63 | L62(G) |
| 64 | R63(A) |
| 72 | Y71(S) |
| 109 | M108(K, R) |

TABLE 4-continued

| aa position | WO 2015/005257<br>Name<br>FPOX variants<br>Origin<br>*Emericella nidulans*<br>SEQ ID NO<br>SEQ 11 |
|---|---|
| 116 | D115(R) |
| 76 | L75(A, F) |
| 67 | P66(H) |
| 96 | D95(E) |
| 106 | K105(R) |
| 355 | A355(S) |

Positions in the sequences of amadoriases of other origins that correspond to positions 62, 63, 64, 72, 109, 116, 76, 67, 96, 106, and 355 of SEQ ID NO: 1 are as shown in the table below.

TABLE 5

| | Name | | | | | |
|---|---|---|---|---|---|---|
| | CFP-T7 | EFP-T5 | PyFX | ArFX | CcFX | NvFX |
| | | | Origin | | | |
| aa position | *Coniochaeta* sp. | *E. terrenum* | *Pyrenochaeta* sp. | *Arthrinium* sp. | *C. clavata* | *N. vasinfecta* |
| | | | SEQ ID NO | | | |
| | SEQ 1 | SEQ 3 | SEQ 4 | SEQ 5 | SEQ 6 | SEQ 7 |
| 62 | R62 | R62 | R62 | R62 | R62 | R62 |
| 63 | L63 | L63 | L63 | L63 | L63 | L63 |
| 64 | R64 | R64 | R64 | R64 | R64 | R64 |
| 72 | S72 | S72 | S72 | S72 | S72 | S72 |
| 109 | K109 | R109 | Q109 | Q109 | Q109 | R109 |
| 116 | D116 | D116 | D116 | D116 | D116 | E116 |
| 76 | R76 | L76 | R76 | Q76 | R76 | R76 |
| 67 | V67 | P67 | V67 | V67 | V67 | V67 |
| 96 | O96 | D96 | D96 | D96 | D96 | D96 |
| 106 | D106 | N106 | D106 | A106 | D106 | G106 |
| 355 | A355 | A355 | A353 | A356 | A353 | S355 |

| | Name | | | | | |
|---|---|---|---|---|---|---|
| | CnFX | PnFX | AnFX | EnFX | UlFX | PjFX |
| | | | Origin | | | |
| aa position | *C. neoformans* | *P. nodorum* | *A. nidulans* | *E. nidulans* | *Ulocladium* sp. | *P. janthinellum* |
| | | | SEQ ID NO | | | |
| | SEQ 8 | SEQ 9 | SEQ 10 | SEQ 11 | SEQ 12 | SEQ 13 |
| 62 | R62 | S62 | R61 | R61 | RS2 | R62 |
| 63 | I63 | L63 | L62 | L62 | L63 | L63 |
| 64 | R64 | R64 | R63 | R63 | R64 | R64 |
| 72 | S72 | A72 | S71 | Y71 | S72 | S72 |
| 109 | K109 | S109 | K108 | M108 | Q109 | R109 |
| 116 | K116 | D116 | D115 | D115 | D116 | D116 |
| 76 | R76 | R76 | L75 | L75 | R76 | L76 |
| 67 | V67 | V67 | P66 | P66 | V67 | P67 |
| 96 | D96 | D96 | D95 | D95 | D96 | D96 |
| 106 | S106 | D106 | G105 | K105 | D106 | S106 |
| 355 | A355 | A351 | A355 | A355 | A353 | A355 |

TABLE 6

| | | | | | Name | | | | |
|---|---|---|---|---|---|---|---|---|---|
| | CFP-T7 | Ao2 | Af2 | At | Fo | Ao1 | Af1 | Pi | Dh |
| | | | | | Origin | | | | |
| aa | Coniochaeta sp. | A. oryzae | A. fumigatus | A. terreus | F. oxysporum | A. oryzae | A. fumigatus | Pichia sp. | D. hansenii |
| | | | | | SEQ ID NO | | | | |
| position | SEQ 1 | SEQ 14 | SEQ 15 | SEQ 16 | SEQ 17 | SEQ 18 | SEQ 19 | SEQ 20 | SEQ 21 |
| 62 | R62 | G58 | G58 | G58 | L59 | R61 | S61 | D53 | T56 |
| 63 | L63 | Q59 | Q59 | Q59 | S60 | E62 | E62 | Y54 | S57 |
| 64 | R64 | Y60 | Y60 | Y60 | T61 | V63 | L63 | V55 | D58 |
| 72 | S72 | A74 | A74 | A74 | S77 | T79 | T79 | S68 | A66 |
| 109 | K109 | I111 | V111 | V111 | E114 | E116 | K116 | E105 | Y103 |
| 118 | D116 | E118 | D118 | E118 | I121 | D123 | E123 | K112 | G110 |
| 76 | R76 | F78 | F78 | F78 | A81 | L83 | L83 | L72 | L70 |
| 67 | V67 | K63 | N63 | K63 | S64 | S66 | G66 | L58 | — |
| 96 | D96 | M98 | M98 | M98 | V101 | V103 | I103 | L92 | Y90 |
| 106 | D106 | R108 | R108 | R108 | Q111 | H113 | H113 | H102 | S100 |
| 355 | A355 | R341 | R343 | R342 | R347 | R350 | R350 | M332 | R332 |

A1cOX may comprise the mutation(s) indicated above. A person skilled in the art can produce an A1cOX gene with reference to Patent Documents 20 to 22 and the description provided above. In one embodiment, for example, A1cOX may comprise, at the position corresponding to position 62 of SEQ ID NO: 1, amino acid substitution with an amino acid other than arginine, such as the amino acid indicated in the table above, and further, lysine, histidine, phenylalanine, tryptophan, tyrosine, or other amino acid. In addition, A1cOX may comprise substitution of 1 or more or 2 or more amino acids, such as 3 amino acids at positions selected from the group consisting of the position corresponding to position 63, the position corresponding to position 355, and the position corresponding to position 419 of SEQ ID NO: 1. Substituted amino acids (amino acids post substitution) may be any of those shown in the table above. Alternatively, A1cOX may comprise substitution of 1 or more, 2 or more, 3 or more, 4 or more, 5 or more, 6 or more, 7 or more, or 8 or more amino acids, such as 9 amino acids at positions selected from the group consisting of the position corresponding to position 63, the position corresponding to position 64, the position corresponding to position 72, the position corresponding to position 109, the position corresponding to position 116, the position corresponding to position 76, the position corresponding to position 67, the position corresponding to position 96, and the position corresponding to position 355 of SEQ ID NO: 1. Substituted amino acids (amino acids post substitution) may be any of those shown in the table above. Optionally, A1cOX may comprise substitution of 1 or more, 2 or more, or 3 or more amino acids, such as 4 amino acids at positions selected from the group consisting of the position corresponding to position 68, the position corresponding to position 356, the position corresponding to position 64, and the position corresponding to position 99 of SEQ ID NO: 1. Substituted amino acids (amino acids post substitution) may be any of those shown in the table above.

(A1cOX Variant)

An A1cOX variant may be produced by introducing the mutation of the present invention into the A1cOX gene, and glycated hemoglobin oxidase having enhanced relative activity on glycated HbS or glycated HbC can be produced.

(Mutations of the Present Invention)

The glycated hemoglobin oxidase of the present invention may comprise mutation(s) at the position(s) corresponding to position 113, 109, 106, and/or 102 of SEQ ID NO: 1. Corresponding positions are explained below. In one embodiment, one or a plurality of amino acid substitutions may be introduced at the positions indicated below into A1cOX based on the amadoriase derived from Coniochaeta sp. NISL 9330 (SEQ ID NO: 1) or the amadoriase (e.g., SEQ ID NO: 45) based on the amadoriase derived from Emericella nidulans (SEQ ID NO: 11):

(a) the position corresponding to position 113 of SEQ ID NO: 1;

(a') the position corresponding to position 109 of SEQ ID NO: 1;

(b) the position corresponding to position 106 of SEQ ID NO: 1; and/or (c) the position corresponding to position 102 of SEQ ID NO: 1.

With regard to the positions indicated above, the amino acid(s) at the position(s) corresponding to position(s) (a) 113, (a') 109, (b) 106, and/or (c) 102 of SEQ ID NO: 1 may be substituted with amino acid(s) other than positively-charged amino acids (lysine, histidine, and arginine), such as aspartic acid, glutamic acid, serine, threonine, asparagine, glutamine, cysteine, glycine, proline, alanine, valine, isoleucine, leucine, methionine, phenylalanine, tyrosine, or tryptophan, for example glutamic acid, aspartic acid, alanine, leucine, valine, glutamine, or asparagine, and for example with glutamic acid, aspartic acid, or alanine.

In some limited embodiments, reverse mutations (back mutations) from the amino acid after substitution to the amino acid in the sequence of the naturally-occurring amadoriase (i.e., the naturally-occurring amino acid) are excluded. In other embodiments, the amino acid after substitution at the position corresponding to position 102, 106, 109, or 113 of SEQ ID NO: 1 can be identical to the amino acid at the position in the sequence of the naturally-occurring amadoriase (i.e., the naturally-occurring amino acid). Such substitution may appear as a reverse mutation (back mutation). However, when the naturally-occurring amino acid is substituted with another amino acid when preparing an A1c oxidase from the naturally-occurring amadoriase, such substitution is understood as a preferable or necessary constitution for the A1c oxidase. Under such circumstance, in order to obtain a glycated hemoglobin oxidase that acts not only on HbA1c but also on glycated HbS or glycated HbC, from said A1c oxidase, an amino acid substitution that modifies the configuration considered to be preferable or configuration considered to be necessary can be understood not as a reverse mutation to the naturally-occurring amadoriase but rather as a substrate-specificity-modifying-amino-acid-substitution in order to achieve the object of the present invention. Accordingly, in one embodiment of the present invention, substitution that may appear to be a reverse mutation into a naturally-occurring amino acid is within the scope of an amino acid substitution that is capable of achieving the object of the present invention.

In one embodiment, the glycated hemoglobin oxidase of the present invention may have specific activity on 10 μM HbS1c-type αF8P that is, for example, 20 mU/mg or greater, 30 mU/mg or greater, 40 mU/mg or greater, 50 mU/mg or greater, 60 mU/mg or greater, 70 mU/mg or greater, 80 mU/mg or greater, 90 mU/mg or greater, 100 mU/mg or greater, 110 mU/mg or greater, 120 mU/mg or greater, 130 mU/mg or greater, 140 mU/mg or greater, 150 mU/mg or greater, 160 mU/mg or greater, 170 mU/mg or greater, or for example, 180 mU/mg or greater. In one embodiment, the glycated hemoglobin oxidase of the present invention may have specific activity on 10 μM HbC1c-type αF8P that is, for example, 20 mU/mg or greater, 30 mU/mg or greater, 40 mU/mg or greater, 50 mU/mg or greater, 60 mU/mg or greater, 70 mU/mg or greater, 80 mU/mg or greater, 90 mU/mg or greater, 100 mU/mg or greater, 110 mU/mg or greater, 120 mU/mg or greater, 130 mU/mg or greater, 140 mU/mg or greater, 150 mU/mg or greater, 160 mU/mg or greater, 170 mU/mg or greater, or for example, 180 mU/mg or greater. In one embodiment, the glycated hemoglobin oxidase of the present invention may have the specific activity on 10 μM HbA1c-type αF8P that is, for example, 20 mU/mg or greater, 30 mU/mg or greater, 40 mU/mg or greater, 50 mU/mg or greater, 60 mU/mg or greater, 70 mU/mg or greater, 80 mU/mg or greater, 90 mU/mg or greater, 100 mU/mg or greater, 110 mU/mg or greater, 120 mU/mg or greater, 130 mU/mg or greater, 140 mU/mg or greater, 150 mU/mg or greater, 160 mU/mg or greater, 170 mU/mg or greater, or for example, 180 mU/mg or greater.

(Corresponding Position)

When a particular position in the reference amino acid sequence corresponds to a particular position in another amino acid sequence similar thereto, such position is referred to as a "corresponding position" in the present specification. Further, an amino acid at a corresponding position is referred to as a "corresponding amino acid." For the convenience of description, a corresponding position is described with reference to the amino acid sequence of the amadoriase derived from the genus *Coniochaeta* of SEQ ID NO: 1. In such a case, a "corresponding position" in an amino acid sequence is a position in the amino acid sequence of an amadoriase derived from another organism species that corresponds to the particular position in the amino acid sequence of the amadoriase derived from the genus *Coniochaeta* of SEQ ID NO: 1.

A method of identifying a "corresponding position" of an amino acid sequence can be performed by, for example, comparing amino acid sequences using a known algorithm such as the Lipman-Pearson method to assign maximum identity to conserved amino acid residues present in the amino acid sequence of each amadoriase. By aligning the amino acid sequences of the amadoriases by such method, the positions of the homologous amino acid residues in each of the amadoriase sequences can be determined, regardless of insertion or deletion of amino acid residues in the amino acid sequences. Corresponding positions (homologous positions) are considered to exist at the same positions in the three-dimensional structures, and amino acid residues at such homologous positions are expected to exert similar effects in terms of specific function of the amadoriase of interest.

(Corresponding Position of Mutation)

The term "the position corresponding to position 113 of the amino acid sequence of SEQ ID NO: 1" used herein refers to the position corresponding to position 113 of SEQ ID NO: 1, when the amino acid sequence of the target amadoriase is compared with the amino acid sequence of SEQ ID NO: 1. The corresponding position can be identified based on FIG. 1 or 2 showing the amino acid sequences aligned by the method described above. The same applies to the position corresponding to position 109, the position corresponding to position 106, and the position corresponding to position 102 of SEQ ID NO: 1.

In various amadoriase sequences, the positions corresponding to positions 102, 106, 109, and 113 of SEQ ID NO: 1 are as shown in the following table.

TABLE 7

| | Name | | | | | |
|---|---|---|---|---|---|---|
| | CFP-T7 | EFP-T5 | PyFX | ArFX | CcFX | NvFX |
| | | | Origin | | | |
| aa | *Coniochaeta* sp. | *E. terrenum* | *Pyrenochaeta* sp. | *Arthrinium* sp. | *C. clavata* | *N. vasinfecta* |
| | | | SEQ ID NO | | | |
| position | SEQ 1 | SEQ 3 | SEQ 4 | SEQ 5 | SEQ 6 | SEQ 7 |
| 102 | E102 | E102 | K102 | K102 | E102 | E102 |
| 106 | D106 | N106 | D106 | A106 | D106 | G106 |
| 109 | K109 | R109 | Q109 | Q109 | Q109 | R109 |
| 113 | A113 | T113 | T113 | T113 | A113 | K113 |

| | Name | | | | | |
|---|---|---|---|---|---|---|
| | CnFX | PnFX | AnFX | EnFX | UlFX | PjFX |
| | | | Origin | | | |
| aa | *C. neoformans* | *P. nodorum* | *A. nidulans* | *E. nidulans* | *Ulocladium* sp. | *P. janthinellum* |
| | | | SEQ ID NO | | | |
| position | SEQ 8 | SEQ 9 | SEQ 10 | SEQ 11 | SEQ 12 | SEQ 13 |
| 102 | E102 | K102 | E101 | E101 | K102 | E102 |
| 106 | S106 | D106 | G105 | K105 | D106 | S106 |

TABLE 7-continued

| 109 | K109 | S109 | K108 | M108 | Q109 | R109 |
| 113 | A113 | A113 | S112 | S112 | A113 | D113 |

In addition, the positions in various amadoriase sequences corresponding to positions 102, 106, 109, and 113 of SEQ ID NO: 1 are as shown in the following table.

TABLE 8

| | | | | | Name | | | | |
|---|---|---|---|---|---|---|---|---|---|
| | | CFP-T7 | Ao2 | Af2 | At | Fo | Ao1 | Af1 | Pi | Dh |
| | | | | | | Origin | | | | |
| | aa | *Coniochaeta* sp. | *A. oryzae* | *A. fumigatus* | *A. terreus* | *F. oxysporum* | *A. oryzae* | *A. fumigates* | *Pichia* sp. | *D. hansenii* |
| | | | | | | SEQ ID NO | | | | |
| position | SEQ 1 | SEQ 14 | SEQ 15 | SEQ 16 | SEQ 17 | SEQ 18 | SEQ 19 | SEQ 20 | SEQ 21 |
| 102 | E102 | A104 | E104 | E104 | K107 | S109 | A109 | A98 | E96 |
| 106 | D106 | R108 | R108 | R108 | Q111 | H113 | H113 | H102 | S100 |
| 109 | K109 | I111 | V111 | V111 | E114 | E116 | K116 | E105 | Y103 |
| 113 | A113 | P115 | P115 | P115 | G118 | D120 | E120 | E109 | Y107 |

(Amino Acid Sequence Homology, Identity, or Similarity)

The amino acid sequence homology, identity, or similarity can be calculated by a program such as maximum matching or search homology of GENETYX (manufactured by GENETYX), a program such as maximum matching or multiple alignment of DNASIS Pro (manufactured by Hitachi Solutions, Ltd.), or a program such as multiple alignment of CLUSTALW. In order to calculate amino acid sequence identity, two or more amadoriases may be aligned, and the positions of identical amino acids in such two or more amadoriases may be determined. The identical regions in amino acid sequences can be determined based on such information. The percent identity of two or more amino acid sequences is determined by subjecting two or more amino acid sequences to alignment using the algorithm such as Blosum62 by designating the total number of amino acids in the aligned region as the denominator and the number of identical amino acids relative to the total number as the numerator. As such, if no identity is found in parts of the two or more amino acid sequences, for example, an amino acid sequence comprises at its C terminus an additional sequence in which no identity is observed, in general, such regions cannot be aligned and, therefore, such regions are not used for calculation of the percent identity.

Further, positions of similar amino acids in two or more amadoriases can be inspected. For example, a plurality of amino acid sequences can be subjected to alignment with the use of CLUSTALW. In such a case, Blosum62 is used as the algorithm and a plurality of amino acid sequences are subjected to alignment. Amino acids determined to be similar as a result of alignment may be referred to as "similar amino acids." In the variant of the present invention, amino acid substitution can be carried out between such similar amino acids. Through such alignment, amino acid sequences composed of the identical amino acids or similar amino acids among a plurality of amino acid sequences can be investigated. Based on such information, the homologous region (conserved region) in the amino acid sequences can be determined.

(Homologous Region)

The term "homologous region(s)" used herein refers to region(s) consisting of identical or similar amino acids at corresponding positions of the reference amadoriase and in the amadoriase being compared, when two or more amadoriases are aligned, wherein the region(s) consist(s) of 3 or more, 4 or more, 5 or more, 6 or more, 7 or more, 8 or more, 9 or more, or 10 or more continuous amino acids. For example, FIG. 1 shows the alignment of amino acid sequences of amadoriases having 74% or higher sequence identity to the amadoriase sequence of SEQ ID NO: 1 over the full length. In such sequences, the region of positions 10 to 32 with reference to the sequence of the amadoriase derived from *Coniochaeta* sp. as shown in SEQ ID NO: 1 consists of identical or similar amino acids, and such region is considered to be (falls under) a homologous region. Similarly, regions of positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 with reference to the sequence of the amadoriase derived from *Coniochaeta* sp. as shown in SEQ ID NO: 1 can be homologous regions. In one embodiment, the homologous region of an amadoriase consists of the positions mentioned above. When another amadoriase is the reference, positions corresponding to positions of SEQ ID NO: 1 can constitute homologous regions. For example, likewise, with reference to the amadoriase derived from *Emericella nidulans* of SEQ ID NO: 45, positions 9 to 31, 35 to 40, 48 to 51, 53 to 57, 62 to 64, 72 to 74, 83 to 85, 87 to 89, 119 to 121, 144 to 149, 155 to 161, 163 to 169, 179 to 181, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 424 to 432 of SEQ ID NO: 45 can constitute homologous regions. In one embodiment, the homologous region of an amadoriase consists of the positions mentioned above. The same applies to SEQ ID NO: 11 from which SEQ ID NO: 45 is derived.

In one embodiment, the homologous region of an amadoriase consists of amino acid sequences of positions 11 to 32, 36 to 41, 50 to 52, 54 to 58, 84 to 86, 88 to 90, 145 to 150, 157 to 168, 202 to 205, 207 to 212, 215 to 225, 236 to 248, 258 to 261, 266 to 268, 270 to 273, 275 to 287, 347 to 354, 357 to 363, 370 to 383, 385 to 387, and 405 to 410 with reference to the sequence of the amadoriase derived from Coniochaeta sp. of SEQ ID NO: 1. In another embodiment, the homologous region of an amadoriase consists of amino acid sequences of positions 10 to 31, 35 to 40, 49 to 51, 53 to 57, 83 to 85, 87 to 89, 144 to 149, 156 to 167, 202 to 205, 207 to 212, 215 to 225, 236 to 248, 258 to 261, 266 to 268, 270 to 273, 275 to 287, 347 to 354, 357 to 363, 370 to 383, 385 to 387, and 405 to 410 with reference to the sequence of the amadoriase derived from Emericella nidulans of SEQ ID NO: 45. The same applies to SEQ ID NO: 11 from which SEQ ID NO: 45 is derived.

In one embodiment, the homologous region of an amadoriase consists of amino acid sequences of positions 11 to 18, 20 to 32, 50 to 52, 54 to 58, 266 to 268, 270 to 273, 277 to 286, and 370 to 383 with reference to the sequence of the amadoriase derived from Coniochaeta sp. of SEQ ID NO: 1. In another embodiment, the homologous region of an amadoriase consists of amino acid sequences of positions 10 to 17, 19 to 31, 49 to 51, 53 to 57, 266 to 268, 270 to 273, 277 to 286, and 370 to 383 with reference to the sequence of the amadoriase derived from Emericella nidulans of SEQ ID NO: 45. The same applies to SEQ ID NO: 11 from which SEQ ID NO: 45 is derived.

(Highly Conserved Amino Acid Residue)

Particular amino acid residues of amadoriases are known to interact with a the sugar portion (e.g., a fructosyl group) of the substrate. Such amino acid residues are highly conserved in various amadoriases. In an amadoriase of one embodiment, the amino acid at the position corresponding to position 239 of SEQ ID NO: 1 is tryptophan, phenylalanine, or tyrosine, the amino acid at the position corresponding to position 282 of SEQ ID NO: 1 is glutamic acid, the amino acid at the position corresponding to position 376 of SEQ ID NO: 1 is glycine, and the amino acid at the position corresponding to position 418 of SEQ ID NO: 1 is arginine. Such amino acid residues are known to recognize the sugar portion (e.g., a fructosyl group) of the substrate (J. Biol. Chem., 283, 27007-27016, 2008; Proteins, 84, 744-758, 2016).

An amadoriase is known to bind to a coenzyme through a particular amino acid sequence motif. In the case of a FAD-binding amadoriase, a motif sequence binding to the coenzyme FAD is Gly-Xaa-Gly-Xaa-Xaa-Gly, wherein Xaa indicates any amino acid (Eur. J. Biochem., 242, 499-505, 1996), and this sequence is highly conserved among various FAD-binding amadoriases. This motif sequence is observed in the amino acid sequence of the positions corresponding to positions 15 to 20 of SEQ ID NO: 1. In one embodiment, accordingly, the amadoriase comprises the amino acid sequence of the positions corresponding to positions 15 to 20 of SEQ ID NO: 1: Gly-Xaa-Gly-Xaa-Xaa-Gly, wherein Xaa indicates any amino acid.

In one embodiment, the amino acid at the position corresponding to position 60 of SEQ ID NO: 1 is preferably glycine, so that the amadoriase can recognize a glycated peptide as a substrate, in addition to a glycated amino acid (WO 2012/018094). In one embodiment, the amino acid at the position corresponding to position 60 of SEQ ID NO: 1 of the amadoriase is not serine, glutamic acid, histidine, or glutamine.

The positions corresponding to positions 239, 282, 376, 418, 15, 17, 20, and 60 of SEQ ID NO: 1 in various amadoriase sequences are as shown in the following table.

TABLE 9

| | Name | | | | | |
|---|---|---|---|---|---|---|
| | CFP-T7 | EFP-T5 | PyFX | ArFX | CcFX | NvFX |
| | Origin | | | | | |
| aa | Coniochaeta sp. | E. terrenum | Pyrenochaeta sp. | Arthrinium sp. | C. clavata | N. vasinfecta |
| | SEQ ID NO | | | | | |
| position | SEQ 1 | SEQ 3 | SEQ 4 | SEQ 5 | SEQ 6 | SEQ 7 |
| 239 | W239 | W239 | W237 | W239 | W237 | W239 |
| 282 | E282 | E282 | E280 | E282 | E280 | E282 |
| 376 | G376 | G376 | G374 | G377 | G374 | G378 |
| 418 | R418 | R418 | R417 | R420 | R417 | R419 |
| 15 | G15 | G15 | G15 | G15 | G15 | G15 |
| 17 | G17 | G17 | G17 | G17 | G17 | G17 |
| 20 | G20 | G20 | G20 | G20 | G20 | G20 |
| 60 | G60 | G60 | G60 | G60 | G60 | G60 |

| | Name | | | | | |
|---|---|---|---|---|---|---|
| | CnFX | PnFX | AnFX | EnFX | UlFX | PjFX |
| | Origin | | | | | |
| aa | C. neoformans | P. nodorum | A. nidulans | E. nidulans | Ulocladium sp. | P. janthinellum |
| | SEQ ID NO | | | | | |
| position | SEQ 8 | SEQ 9 | SEQ 10 | SEQ 11 | SEQ 12 | SEQ 13 |
| 239 | W239 | W235 | W239 | W239 | W237 | W239 |
| 282 | E282 | E278 | E282 | E282 | E280 | E282 |
| 376 | G376 | G372 | G376 | G376 | G374 | G376 |
| 418 | R419 | R415 | R419 | R419 | R417 | R418 |

TABLE 9-continued

| 15 | G15 | G15 | G14 | G14 | G15 | G15 |
| 17 | G17 | G17 | 616 | G16 | G17 | G17 |
| 20 | G20 | G20 | G19 | G19 | G20 | G20 |
| 60 | G60 | G60 | S59 | G59 | G60 | S60 |

In addition, the positions in various amadoriase sequences corresponding to positions 239, 282, 376, 418, 15, 17, 20, and 60 of SEQ ID NO: 1 are as shown in the following table.

TABLE 10

| | Name | | | | | | | | |
|---|---|---|---|---|---|---|---|---|---|
| | CFP-T7 | Ao2 | Af2 | At | Fo | Ao1 | Af1 | Pi | Dh |
| | | | | | Origin | | | | |
| aa | *Coniochaeta* sp. | *A. oryzae* | *A. fumigatus* | *A. terreus* | *E. oxysporum* SEQ ID NO | *A. oryzae* | *A. fumigatus* | *Pichia* sp. | *D. hansenii* |
| position | SEQ 1 | SEQ 14 | SEQ 15 | SEQ 16 | SEQ 17 | SEQ 18 | SEQ 19 | SEQ 20 | SEQ 21 |
| 239 | W239 | W234 | W236 | W235 | W239 | W241 | W241 | F230 | Y231 |
| 282 | E282 | E278 | E280 | E279 | E283 | E285 | E285 | E273 | E274 |
| 376 | G376 | G362 | G364 | G363 | G368 | G371 | G371 | G353 | G353 |
| 418 | R418 | R409 | R411 | R410 | R415 | R418 | R418 | R399 | R403 |
| 15 | G15 | G13 | G13 | G13 | G14 | G16 | G16 | G8 | G11 |
| 17 | G17 | G15 | G15 | G1S | G16 | G18 | G18 | G10 | G13 |
| 20 | G20 | G18 | G18 | G18 | G19 | G21 | G21 | G13 | G16 |
| 60 | G60 | S56 | S56 | S56 | G57 | E59 | E59 | H51 | Q54 |

In one embodiment, the glycated hemoglobin oxidase variant of the present invention has, for example, 50% or higher, 55% or higher, 60% or higher, 61% or higher, 62% or higher, 63% or higher, 64% or higher, 65% or higher, 66% or higher, 67% or higher, 68% or higher, 69% or higher, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher amino acid sequence identity to the amino acid sequence of the amadoriase of SEQ ID NO: 1 over the full length, when the amino acid sequence thereof is aligned with the amadoriase having the amino acid sequence of SEQ ID NO: 1, and has enhanced relative activity (HbS1c/HbA1c) and/or relative activity (HbC1c/A1cOX), compared with those of the A1cOX before modification. In addition, the amino acid sequence of the homologous region of the glycated hemoglobin oxidase variant of the present invention can exhibit, for example, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or for example, 99% or higher sequence identity to the amino acid sequence of the homologous region of SEQ ID NO: 1.

In one embodiment, the glycated hemoglobin oxidase variant of the present invention comprises an amino acid sequence derived from the amino acid sequence of SEQ ID NO: 1 by modification or mutation or deletion, substitution, addition, and/or insertion of 1 or several amino acids at positions other than the positions corresponding to 113, 109, 106, and 102 of SEQ ID NO: 1 and has enhanced relative activity (HbS1c/HbA1c) and/or relative activity (HbC1c/HbA1c), compared with the A1cOX before modification. The term "1 or several amino acids" used herein refers to, for example, 1 to 15, 1 to 10, 1 to 7, 1 to 5, 1 to 4, 1 to 3, or for example 1 or 2 amino acids.

In one embodiment, the glycated hemoglobin oxidase of the present invention is selected from the following:

(i) a glycated hemoglobin oxidase, wherein, when the amino acid sequence of the glycated hemoglobin oxidase is aligned with the amino acid sequence of SEQ ID NO: 1, the amino acid(s) at the position(s) corresponding to position(s) 113, 109, 106, and/or 102 of the amino acid sequence of SEQ ID NO: 1 is(are) modified into an amino acid (or amino acids) selected from the group consisting of glutamic acid, alanine, aspartic acid, serine, threonine, asparagine, glutamine, cysteine, glycine, proline, valine, isoleucine, leucine, methionine, phenylalanine, tyrosine, and tryptophan;

(ii) the glycated hemoglobin oxidase as defined in (i) comprising an amino acid sequence having a substitution, deletion, or addition of 1 or several amino acids at positions other than those corresponding to positions 113, 109, 106, and 102 of the amino acid sequence of SEQ ID NO: 1;

(iii) the glycated hemoglobin oxidase as defined in (i) or (ii) comprising an amino acid sequence having, for example, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, or 95% or higher sequence identity with the amino acid sequence of SEQ ID NO: 1, SEQ ID NO: 22, SEQ ID NO: 24, SEQ ID NO: 11, or SEQ ID NO: 45 over the full length;

(iv) the glycated hemoglobin oxidase as defined in (i) or (ii) comprising an amino acid sequence having, for example, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 90% or higher, or 95% or higher sequence identity with the amino acid sequence of SEQ ID NO: 1, SEQ ID NO: 11, or SEQ ID NO: 45 over the full length, wherein the amino acid at the position corresponding to position 60 of SEQ ID NO: 1 is glycine, the amino acid at the position corresponding to position 239 of SEQ ID NO: 1 is tryptophan, phenylalanine, or tyrosine, the amino acid at the position corresponding to position 282 of SEQ ID NO: 1 is glutamic acid, the amino acid at the position corresponding to position 376 of SEQ ID NO: 1 is glycine, the amino acid at the position corresponding to position 418 of SEQ ID NO: 1 is arginine, and the amino acid sequence of the positions corresponding to positions 15 to 20 of SEQ ID NO: 1 is Gly-Xaa-Gly-Xaa-Xaa-Gly, wherein Xaa indicates any amino acid;

(v) the glycated hemoglobin oxidase as defined in (i), (ii), or (iii) comprising an amino acid sequence having 70% or higher, 71% or higher, 72% or higher, 73% or higher, 74% or higher, 75% or higher, 80% or higher, 85% or higher, or 90% or higher sequence identity with the amino acid sequence of SEQ ID NO: 1, SEQ ID NO: 22, SEQ ID NO: 24, SEQ ID NO: 11, or SEQ ID NO: 45 over the full length and 80% or higher, 85% or higher, 90%, 95% or higher, 98% or higher, or 99% or higher sequence identity between amino acid sequences of the homologous region consisting of amino acids at positions 10 to 32, 36 to 41, 49 to 52, 54 to 58, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of SEQ ID NO: 1, SEQ ID NO: 22, or SEQ ID NO: 24 and the amino acid sequence of the homologous region of the corresponding positions of the glycated hemoglobin oxidase; and (vi) the glycated hemoglobin oxidase as defined in (i) or (ii) comprising an amino acid sequence having, 50% or higher, 55% or higher, 60% or higher, 61% or higher, 62% or higher, 63% or higher, 64% or higher, 65% or higher, 66% or higher, 67% or higher, 68% or higher, 69% or higher, 70% or higher, 71% or higher, 72% or higher, 73% or higher, 74% or higher, 75% or higher, 76% or higher, 77% or higher, 78% or higher, 79% or higher, 80% or higher, 85% or higher, or for example 90% or higher sequence identity with the amino acid sequence of SEQ ID NO: 1, SEQ ID NO: 11, or SEQ ID NO: 45 over the full length and 65% or higher, 66% or higher, 67% or higher, 68% or higher, 69% or higher, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, or for example 90% or higher sequence identity between the amino acid sequence of the homologous region consisting of amino acids at positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of SEQ ID NO: 1 and the amino acid sequence of the homologous region of the corresponding positions of the glycated hemoglobin oxidase, wherein the amino acid at the position corresponding to position 60 of SEQ ID NO: 1 is glycine, the amino acid at the position corresponding to position 239 of SEQ ID NO: 1 is tryptophan, phenylalanine, or tyrosine, the amino acid at the position corresponding to position 282 of SEQ ID NO: 1 is glutamic acid, the amino acid at the position corresponding to position 376 of SEQ ID NO: 1 is glycine, the amino acid at the position corresponding to position 418 of SEQ ID NO: 1 is arginine, and the amino acid sequence of the positions corresponding to positions 15 to 20 of SEQ ID NO: 1 is Gly-Xaa-Gly-Xaa-Xaa-Gly, wherein Xaa indicates any amino acid. This glycated hemoglobin oxidase has the following features:

(a) the ratio of activity on HbS1c-type αF8P to activity on HbA1c-type αF8P; i.e., relative activity (HbS1c/HbA1c), is enhanced, compared with the A1c oxidase before modification;

(b) the ratio of activity on HbC1c-type αF8P to activity on HbA1c-type αF8P; i.e., relative activity (HbC1c/HbA1c), is enhanced, compared with the A1c oxidase before modification;

(c) the ratio of activity on HbS1c-type αF8P to activity on HbA1c-type αF8P; i.e., relative activity (HbS1c/HbA1c), is, for example, 0.45 or more, 0.5 or more, 0.6 or more, 0.7 or more, 0.8 or more, or 0.9 or more, compared with the A1c oxidase before modification; and/or (d) the ratio of activity on HbC1c-type αF8P to activity on HbA1c-type αF8P; i.e., relative activity (HbC1c/HbA1c), is, for example, 0.15 or more, 0.2 or more, 0.3 or more, 0.4 or more, 0.5 or more, 0.6 or more, 0.7 or more, 0.8 or more, or 0.9 or more.

In one embodiment, the glycated hemoglobin oxidase of the present invention has the following features:

(i) when the amino acid sequence of the glycated hemoglobin oxidase is aligned with the amino acid sequence of SEQ ID NO: 1, 1, 2, or 3 amino acid(s) at the position(s) corresponding to position(s) 113, 109, 106, and/or 102 of the amino acid sequence of SEQ ID NO: 1 is(are) modified into an amino acid (or amino acids) (or amino acids) selected from the group consisting of glutamic acid, aspartic acid, alanine, serine, threonine, asparagine, glutamine, cysteine, glycine, proline, valine, isoleucine, leucine, methionine, phenylalanine, tyrosine, and tryptophan; and (a) the ratio of activity on HbS1c-type αF8P to activity on HbA1c-type αF8P; i.e., the relative activity (HbS1c/HbA1c), is 0.45 or more, and/or (b) the ratio of activity on HbC1c-type αF8P to activity on HbA1c-type αF8P; i.e., the relative activity (HbC1c/HbA1c), is 0.15 or more, such as 0.2 or more.

The present inventor found that the glycated hemoglobin oxidase resulting from substitution of an amino acid at the position corresponding to position 102, 106, 109, or 113 of SEQ ID NO: 1 with an amino acid other than a positively-charged amino acid has enhanced relative activity (HbS1c/HbA1c) and/or relative activity (HbC1c/HbA1c), compared with the enzyme before modification. Based on such finding, a person skilled in the art will appreciate that other AlcOxs having substitution of an amino acid(s) at the position(s) corresponding to position 102, 106, 109, or 113 of the amino acid sequence of SEQ ID NO: 1 with an amino acid other than a positively-charged amino acid will also have the enhanced relative activity (HbS1c/HbA1c) and/or relative activity (HbC1c/HbA1c), will act on glycated hemoglobin of various genotypes, and can be used for the measurement thereof (Production of Glycated Hemoglobin Oxidase)

In one embodiment, the present invention provides a method for producing glycated hemoglobin oxidase comprising a step of culturing a strain capable of producing glycated hemoglobin oxidase under conditions where the glycated hemoglobin oxidase can be expressed and a step of isolating glycated hemoglobin oxidase from a culture product or culture solution. In such method, a host cell transformed with a vector comprising a gene encoding the glycated hemoglobin oxidase of the present invention integrated therein can be used. The phrase conditions where the glycated hemoglobin oxidase can be expressed refers to conditions where a glycated hemoglobin oxidase gene is transcribed and translated, and a polypeptide encoded by such gene is produced.

Further, examples of media to culture the strains mentioned above include media prepared by adding 1 or more inorganic salts selected from among, for example, sodium chloride, monopotassium phosphate, dipotassium phosphate, magnesium sulfate, magnesium chloride, ferric chloride, ferric sulfate, and manganese sulfate to 1 or more nitrogen sources, such as a yeast extract, tryptone, peptone, a meat extract, a corn steep liquor, and a leaching solution of soybean or wheat bran, and adequately adding saccharine materials (sugar sources), vitamins, and the like thereto, where necessary.

Further, a substrate with which the glycated hemoglobin oxidase can react or a compound similar thereto, such as a glycated protein, including a glycated amino acid, a glycated peptide, a degradation product of a glycated protein, glycated hemoglobin, or glycated albumin, may be added to the media, so as to increase the amount of the target enzyme to be produced.

It is appropriate to adjust the initial pH of the media to 7 to 9. Culture is preferably performed at 20° C. to 42° C., and more preferably at about 25° C. to 37° C. for 4 to 24 hours, and further preferably at about 25° C. to 37° C. for 8 to 16 hours, by, for example, aeration spinner submerged culture, shake culture, or stationary culture.

Following the completion of culture, glycated hemoglobin oxidase may be collected from the culture products with conventional enzyme collecting means. For example, a strain may be subjected to ultrasonic disintegration treatment or grinding treatment by a conventional method, the enzyme may be extracted using a lytic enzyme such as lysozyme, or bacteriolysis may be performed via shaking or still standing in the presence of toluene to excrete the enzyme from the microorganism body. The solution is filtered or centrifuged to remove solid content, and a nucleic acid is removed with the aid of streptomycin sulfate, protamine sulfate, or manganese sulfate, according to need. Thereafter, ammonium sulfate, alcohol, acetone, or the like is added thereto, so as to fractionate the solution, and sediments are then collected to obtain the crude enzymes.

The purified enzyme preparation can be obtained from the crude enzyme by a method appropriately selected from: gel filtration methods using Sephadex, Superdex, or Ultrogel; adsorption-elution methods using ion exchange carriers, hydrophobic carriers, or hydroxyapatite; electrophoretic methods using polyacrylamide gels, etc.; sedimentation methods such as sucrose density-gradient centrifugation; affinity chromatographic methods; and fractionation methods using a molecular sieve membrane, a hollow-fiber membrane, etc. Alternatively, the methods mentioned above can be performed in adequately combination. The purified glycated hemoglobin oxidase preparation can be thus obtained.

In one embodiment, the glycated hemoglobin oxidase of the present invention preferably:

recognizes HbA1c, and recognizes glycated HbS and/or glycated HbC as a substrate;

oxidizes the β chain of glycated hemoglobin to generate hydrogen peroxide;

has an optimal pH range of 6 to 8;

has an operative pH range of 5 to 9;

has an optimal temperature range of 25° C. to 40° C.; and has a molecular weight of about 45 to 55 KDa, such as about 48 to 50 KDa, on SDS-PAGE.

In one embodiment, the glycated hemoglobin oxidase of the present invention is subjected to heat treatment at 30° C. to 40° C., such as 35° C., for 30 minutes, and retains, for example, 50% or more, 60% or more, 70% or more, or 80% or more activity thereafter.

Amadoriases exerting no activity on glycated hemoglobin are excluded from the glycated hemoglobin oxidase variant of the present invention.

(Composition, Reagent, and Kit)

In one embodiment, the present invention provides a reagent composition for measurement of glycated hemoglobin or a reagent or kit used for measurement comprising glycated hemoglobin oxidase. In one embodiment, the present invention provides a reagent composition for measurement of HbS1c or HbC1c or a reagent or kit used for measurement comprising glycated hemoglobin oxidase. The composition, reagent, or kit may comprise a reagent for measurement of a reduced compound, a reagent for measurement of hydrogen peroxide, a buffer, a surfactant, a salt, a preservative, or the like. The composition, reagent, or kit may be supplemented with, for example, a solubilizer, a stabilizer, a reaction-improving agent, a glycated hemoglobin denaturation agent, a reducing agent, bovine serum albumin, or a saccharide (e.g., glycerin, lactose, or sucrose). The composition, reagent, or kit may be supplemented with other known stabilizers, or systems that delete contaminants, and the like, according to need. Techniques that are employed for various conventional reagents or kits for the purpose of measuring a glycated peptide by enzymatic methods using a protease or the like capable of reacting with glycated hemoglobin may be adequately modified, and such modified technique(s) can be employed for the composition, reagent, or kit of the present invention. The composition, reagent, or kit of the present invention may comprise a protease or need not comprise a protease.

Examples of surfactants include nonionic surfactants and ionic surfactants, such as cationic surfactants, anionic surfactants, and amphoteric surfactants.

Examples of nonionic surfactants include polyoxyethylene alkyl ether, sorbitan fatty acid ester, alkyl polyglucoside, fatty acid diethanol amide, and alkyl monoglyceryl ether.

Examples of cationic surfactants include alkyltrimethylammonium salt, dialkyldimethylammonium salt, alkylbenzyldimethylammonium salt, pyridinium salt, such as alkylpyridinium salt, phosphonium salt, such as alkylphosphonium salt, imidazolium salt, such as alkylimidazolium salt, and isoquinolinium salt, such as alkylisoquinolinium salt.

A reagent for measurement of hydrogen peroxide may comprise peroxidase and/or a color substrate. Examples of color substrates include, in addition to 4-aminoantipyrine, ADOS (N-ethyl-N-(2-hydroxy-3-sulfopropyl)-m-anisidine), ALOS (N-ethyl-N-(2-hydroxy-3-sulfopropyl)aniline), TOOS (N-ethyl-N-(2-hydroxy-3-sulfopropyl)-m-toluidine sodium), DA-67 (10-(carboxymethylaminocarbonyl)-3,7-bis(dimethylamino)-phenothiazine), and DA-64 (N-(carboxymethylaminocarbonyl)-4,4'-bis(dimethylamino)-diphenyl amine).

(Method for Measurement of Glycated Hemoglobin)

In one embodiment, the present invention provides a method for measurement of glycated hemoglobin. The method for measurement of glycated hemoglobin may be a qualitative or quantitative method. The quantitative method comprises a step of bringing a glycated hemoglobin-containing sample into contact with the glycated hemoglobin oxidase of the present invention and a step of measuring the amount of substances produced or consumed by the reaction. The glycated hemoglobin may be in a naturally occurring or denatured state. The term "contact" used in accordance with the quantifying method encompasses any aspect (form) of physical contact between the glycated hemoglobin oxidase and a sample, such that the glycated hemoglobin oxidase can catalyze the oxidation reaction of the glycated hemoglobin. For example, not only cases in which a free enzyme is mixed with glycated hemoglobin in a solution, but also cases in which a liquid sample comprising glycated hemoglobin can be added or dropped (added dropwise) to the enzyme immobilized on a solid support.

In one embodiment, the present invention provides a method for measurement of HbS1c or HbC1c. This method comprises a step of allowing glycated hemoglobin oxidase to act on a sample that may contain HbS1c or HbC1c. In one embodiment, the amount of a reduced compound generated by the action of glycated hemoglobin oxidase is measured. In one embodiment, the reduced compound to be measured is hydrogen peroxide.

A sample used for measurement can be any type of biological sample that can contain glycated hemoglobin, such as a sample derived from blood, body fluid, or lymph. A sample can appropriately be a processed sample.

In order to improve the reaction efficiency between the glycated hemoglobin oxidase and glycated hemoglobin, denatured glycated hemoglobin may be used. Examples of denaturing treatment include surfactant treatment, heat treatment, denaturing treatment with the aid of an acid or alkali, and combination of any thereof.

When the amount of the enzyme used and the duration of the reaction are maintained at constant levels and the amount of glycated hemoglobin to be added is altered, the range of glycated hemoglobin concentration in which the absorbance of the detected luminescent substrate proportionally decreases as the amount of added glycated hemoglobin decreases can be investigated in order to determine the lowest glycated hemoglobin concentration that can be detected (detection limit concentration) using the amadoriase. It is possible to configure the amount of enzyme and duration of reaction, so as to adjust the detection limit of glycated hemoglobin to a level lower than the glycated hemoglobin level in the sample or in the blood.

According to the quantitative method of measurement, a calibration curve can be prepared in advance by performing regression analysis such as the method of least squares based on the measured absorbance of the control sample comprising glycated hemoglobin at a known concentration. The measured value of the sample containing glycated hemoglobin at an unknown concentration may be plotted on the prepared calibration curve, to quantify the glycated hemoglobin level in the sample.

The time glycated hemoglobin oxidase is allowed to act on a sample containing glycated hemoglobin may be 5 seconds or longer, 10 seconds or longer, 20 seconds or longer, 30 seconds or longer, or 1 minute or longer to less than 60 minutes, less than 30 minutes, less than 10 minutes, or less than 5 minutes, for example, 0.5 minutes or more to less than 60 minutes, 1 minute or more to less than 30 minutes, 1 minute or more to less than 20 minutes, 1 minute or more to less than 10 minutes, or 1 minute or more to less than 5 minutes. While the reaction temperature may vary depending on the optimal temperature of the enzyme being used, the reaction temperature is, for example, from 20° C. to 45° C., and a temperature that is generally employed for an enzymatic reaction can adequately be selected.

While the amount of the glycated hemoglobin oxidase to be used varies depending on the amount of the substrate contained in the sample solution, the enzyme can be added to the solution to a final concentration of, for example, 0.1 to 50 U/ml or for example 0.2 to 10 U/ml. A pH level at the time of reaction can be adjusted using a buffer by taking a pH level at which an amadoriase can act, for example the optimal pH level, into consideration. The reaction pH level is, for example, 3 to 11, 5 to 9, or 6 to 8.

Measurement of hydrogen peroxide can be carried out simultaneously during the step of hydrogen peroxide generation, and measurement can be allowed to proceed simultaneously with the reaction with an amadoriase. A substance consumed by the reaction may be subjected to measurement instead of the reaction product. An example of the substance consumed by the reaction to be measured is dissolved oxygen, and the amount of dissolved oxygen in the reaction solution can be measured with the use of a dissolved oxygen meter or the like.

(Method for Measurement of Amadoriase Activity)

Hereinbelow, while an example of a method for measurement of amadoriase activity involving the use of, HbA1c-type αF8P, HbS1c-type αF8P, or HbC1c-type αF8P as a model substrate, is provided, the method for measurement is not limited thereto. Such substrates can be synthetic substrates (manufactured by Peptide Institute, Inc.). In the present specification, regarding the enzyme titer, unless otherwise specified, the amount of the enzyme that generates 1 μmol of hydrogen peroxide per minute, when carrying out measurement using HbA1c-type αF8P as the substrate, is defined as 1 U.

When evaluation using another substrate is necessary, a glycated peptide, such as aFL or αFVH, synthesized and purified based on the method of, for example, Sakaue et al. can be used (see JP 2001-95598 A). aF6P is obtained by treating HbA1c with endoproteinase Glu-C(Clin. Chem., 43, 1994-1951, 1997). aF6P provided as a synthetic substrate (manufactured by Peptide Institute, Inc.) can also be used.

A: Reagents for Measurement of Activity (Reagent 1): 0.1 M phosphate buffer (pH 6.5) containing 5 U/ml peroxidase (manufactured by Toyobo Co., Ltd.) and 0.49 mM 4-aminoantipyrine (manufactured by Wako Pure Chemical Industries, Ltd.)

(Reagent 2): 15 mM TOOS (N-ethyl-N-(2-hydroxy-3-sulfopropyl)-m-toluidine sodium, manufactured by Dojindo Laboratories) solution 500 mg of TOOS is dissolved in ion-exchange water and the volume of the solution is fixed to 100 ml.
(Reagent 3): 300 μM HbA1c-type, HbC1c-type, or HbS1c-type αF8P (manufactured by Peptide Institute, Inc.) solution (final concentration: 10 μM)
B: Method for Measurement of Activity 2.7 ml of Reagent 1, 100 μl of Reagent 2, and 100 μl of the enzyme solution are mixed, and the mixture is preliminarily heated at 37° C. for 5 minutes. Subsequently, 100 μl of Reagent 3 is added, the resultant is thoroughly mixed, and the absorbance at 555 nm with the elapse of time is then measured at 37° C. using a spectrophotometer (U-3900, manufactured by Hitachi High-Tech Science Corporation) to determine the change in absorbance per minute (ΔAs) at 555 nm. Incidentally, a control solution is prepared in the same manner described above, with the exception that 100 μl of ion-exchange water is added instead of 100 μl of Reagent 3, and the change in absorbance per minute (ΔAO) at 555 nm thereof is determined. The number of micromoles of hydrogen peroxide generated at 37° C. per minute is defined as an activity unit (U) in the enzyme solution and calculated in accordance with the equation shown below.

$$\text{Activity (U/ml)} = \{(\Delta As - \Delta A0) \times 3.0 \times df\} \div (39.2 \times 0.5 \times 0.1)$$

ΔAs: the change in absorbance of the reaction solution per minute
ΔA$_0$: the change in absorbance of the control solution per minute
39.2: the millimolar extinction coefficient of quinoneimine dye generated by the reaction (mM$^{-1}$·cm$^{-1}$)
0.5: the mole number of quinoneimine dye generated by 1 mol of hydrogen peroxide
df: the dilution factor
(Method for Preparing Further Glycated Hemoglobin Oxidase)

The present inventor found a novel object (problem), namely that glycated hemoglobin oxidase capable of reacting not only with HbA1c but also with HbS1c or HbC1c is necessary and further solved the object (problem) by introducing a particular amino acid substitution into A1cOX and producing glycated hemoglobin oxidase. Mutations of the present invention can appropriately be combined. Moreover, further modified variatnts can be prepared based on the finding of the present invention. In one embodiment, accordingly, the present invention provides a method of modifying an amadoriase or A1c oxidase to prepare glycated hemoglobin oxidase that comprises the following steps:

(i) obtaining an amadoriase gene or A1c oxidase gene;
(ii) integrating the amadoriase gene or A1c oxidase gene into a vector, transforming a host cell, expressing the amadoriase or A1c oxidase, and isolating the expressed product;
(iii) measuring the relative activity (HbS1c/HbA1c) and/or the relative activity (HbC1c/HbA1c) of the expressed product;
(iv) modifying the amadoriase gene or A1c oxidase gene such that, when the amino acid sequence of the amadoriase or A1c oxidase is aligned with the amino acid sequence of SEQ ID NO: 1, the amino acid at the position corresponding to position 113, 109, 106, or 102 of the amino acid sequence of SEQ ID NO: 1 is modified into an amino acid selected from the group consisting of glutamic acid, aspartic acid, alanine, serine, threonine, asparagine, glutamine, cysteine, glycine, proline, valine, isoleucine, leucine, methionine, phenylalanine, tyrosine, and tryptophan;
(v) integrating the modified gene into a vector, transforming a host cell, expressing the modified variant, and isolating the expressed product;
(vi) measuring the relative activity (HbS1c/HbA1c) and/or the relative activity (HbC1c/HbA1c) of the expressed product of the modified variant and comparing the measured values with the values measured in step (iii);
(vii) when the relative activity (HbS1c/HbA1c) of the modified variant is 1.1 times or greater than the relative activity (HbS1c/HbA1c) of the amadoriase or A1c oxidase before modification or the relative activity (HbC1c/HbA1c) of the modified variant is 1.1 times or greater than the relative activity (HbC1c/HbA1c) of the amadoriase or A1c oxidase before modification, designating the modified variant as a glycated hemoglobin oxidase; and
(viii) repeating steps (iv) to (vi) on the glycated hemoglobin oxidase of step (vii), according to need.

In the steps (iii) or (vi) above, while αF8P can be used as the evaluation substrate for convenience, other fructosyl substrates comprising 6 or more amino acids, or HbA1c, HbS1c, or HbC1c may also be used.

EXAMPLES

Hereafter, the present invention is described in greater detail with reference to the examples. However, the technical scope of the present invention is not limited to these examples.

1. Preparation of Recombinant Plasmid Encoding an Amadoriase Derived from the Genus *Coniochaeta*

A strain of *E. coli* JM109 (pKK223-3-CFP-T7-H38-GY) having the recombinant plasmid of an amadoriase gene derived from the genus *Coniochaeta* (SEQ ID NO: 23) (WO 2016/159384) was inoculated into 3 ml of LB-amp media (1% (w/v) bactotrypton, 0.5% (w/v) peptone, 0.5% (w/v) NaCl, and 50 μg/ml ampicillin) and shake culture was conducted at 37° C. for 16 hours to obtain a culture product.

The culture product was centrifuged at 10,000×g for 1 minute to collect strains. A recombinant plasmid pKK223-3-CFP-T7-H38-GY was extracted and purified therefrom using the GenElute Plasmid Mini-Prep Kit (manufactured by Sigma-Aldrich Corporation), and 2.5 μl of the recombinant plasmid pKK223-3-CFP-T7-H38-GY was obtained.

2. Site-Directed Modification Operation of Recombinant Plasmid Encoding an Amadoriase Derived from the Genus *Coniochaeta*

PCR was carried out under the conditions described below using the recombinant plasmid pKK223-3-CFP-T7-H38-GY as the template, synthetic oligonucleotides of SEQ ID NOs: 25 and 26, and KOD-Plus-Neo (manufactured by Toyobo Co., Ltd.).

That is, 5 μl of 10×PCR buffer for KOD-Plus-Neo, 5 μl of a dNTPs mixture in which each dNTP was adjusted at 2 mM, 3 μl of a 25 mM MgSO$_4$ solution, 50 ng of plasmid DNA as the template, 15 pmol each of the synthetic oligonucleotides, and 1 unit of KOD-Plus-Neo were mixed, and sterilized water was added thereto in order to bring the total amount of the solution to 50 μl. The prepared reaction solution was subjected to incubation using a thermal cycler (manufactured by Eppendorf Co.) at 94° C. for 2 minutes, and a cycle of 94° C. for 15 seconds, 50° C. for 30 seconds, and 68° C. for 3 minutes was then repeated 15 times.

The DNAs obtained were treated with a restriction enzyme Dpnl (manufactured by New England Biolabs), the remaining template DNAs were cleaved, strains of *E. coli*

JM109 were transformed, and the transformants were then spread on LB-amp agar media. The grown colonies were inoculated into LB-amp media and shake-cultured therein, and plasmid DNAs were isolated in accordance with a conventional technique. The nucleotide sequences of DNAs encoding amadoriases in the plasmids were determined using a multi-capillary DNA analysis system (Applied Biosystems 3130x1 Genetic Analyzer; manufactured by Life Technologies), and introduction of the mutation was confirmed. Thus, the recombinant plasmid encoding the modified amadoriase resulting from introduction of the mutation of interest was obtained (pKK223-3-CFP-T7-H39-1M).

PCR was carried out under the conditions described below using the recombinant plasmid pKK223-3-CFP-T7-H39-M as the template, synthetic oligonucleotides of SEQ ID NOs: 27 and 28, and KOD-Plus-Neo (manufactured by Toyobo Co., Ltd.).

That is, 5 µl of 10×PCR buffer for KOD-Plus-Neo, 5 µl of a dNTPs mixture in which each dNTP was adjusted at 2 mM, 3 µl of a 25 mM MgSO$_4$ solution, 50 ng of plasmid DNA as the template, 15 pmol each of the synthetic oligonucleotides, and 1 unit of KOD-Plus-Neo were mixed, and sterilized water was added thereto in order to bring the total amount of the solution to 50 µl. The prepared reaction solution was subjected to incubation using a thermal cycler (manufactured by Eppendorf Co.) at 94° C. for 2 minutes, and a cycle of 94° C. for 15 seconds and 68° C. for 3 minutes was then repeated 7 times.

The DNAs obtained were treated with a restriction enzyme Dpnl (manufactured by New England Biolabs), and the remaining template DNAs were cleaved. The reaction solution after the treatment with Dpnl (2 µl), 5 µl of Ligation high Ver.2 (manufactured by Toyobo Co., Ltd.), and 5 units of T4 Polynucleotide Kinase (manufactured by Toyobo Co., Ltd.) were mixed, sterilized water was added thereto in order to bring the total amount of the solution to 15 µl, and the resulting solution was subjected to ligation at 16° C. for 1 hour. The strains of E. coli JM109 were transformed using the resulting cyclic DNAs, and the transformants were then spread on LB-amp agar media. The grown colonies were inoculated into LB-amp media and shake-cultured therein, and plasmid DNAs were isolated in accordance with a conventional technique. The nucleotide sequences of DNAs encoding amadoriases in the plasmids were determined using a multi-capillary DNA analysis system (Applied Biosystems 3130x1 Genetic Analyzer; manufactured by Life Technologies), and introduction of the mutation was confirmed. Thus, the recombinant plasmid encoding the modified amadoriase resulting from introduction of the mutation of interest was obtained (pKK223-3-CFP-T7-H39-3M).

PCR was carried out under the conditions described below using the recombinant plasmid pKK223-3-CFP-T7-H39-3M as the template, synthetic oligonucleotides of SEQ ID NOs: 29 and 30, and KOD-Plus-Neo (manufactured by Toyobo Co., Ltd.).

That is, 5 µl of 10×PCR buffer for KOD-Plus-Neo, 5 µl of a dNTPs mixture in which each dNTP was adjusted at 2 mM, 3 µl of a 25 mM MgSO$_4$ solution, 50 ng of plasmid DNA as the template, 15 pmol each of the synthetic oligonucleotides, and 1 unit of KOD-Plus-Neo were mixed, and sterilized water was added thereto in order to bring the total amount of the solution to 50 µl. The prepared reaction solution was subjected to incubation using a thermal cycler (manufactured by Eppendorf Co.) at 94° C. for 2 minutes, and a cycle of 94° C. for 15 seconds, 50° C. for 30 seconds, and 68° C. for 3 minutes was then repeated 15 times.

The DNAs obtained were treated with a restriction enzyme Dpnl (manufactured by New England Biolabs), and the remaining template DNAs were cleaved. Thereafter, strains of E. coli JM109 were transformed, and the transformants were then spread on LB-amp agar media. The grown colonies were inoculated into LB-amp media and shake-cultured therein, and plasmid DNAs were isolated in accordance with a conventional technique. The nucleotide sequences of DNAs encoding amadoriases in the plasmids were determined using a multi-capillary DNA analysis system (Applied Biosystems 3130x1 Genetic Analyzer; manufactured by Life Technologies), and introduction of the mutation was confirmed. Thus, the recombinant plasmid encoding the modified amadoriase resulting from introduction of the mutation of interest was obtained (pKK223-3-CFP-T7-H40-3M).

3. Production and Purification of Amadoriase Derived from the Genus *Coniochaeta*

The transformed E. coli strains (JM109) producing amadoriases obtained in the manner described above were inoculated into 100 ml of LB-amp media supplemented with IPTG to a final concentration of 0.1 mM therein and cultured at 25° C. for 16 hours. The resulting cultured strains were washed with a 10 mM potassium phosphate buffer (pH 7.5), the washed strains were suspended in the same buffer, the resulting suspension was ultrasonically disintegrated, and the resultant was centrifuged at 20,000×g for 10 minutes to prepare 40 ml of a crude enzyme solution.

The HiScreen Capto Q column (manufactured by GE Healthcare) was equilibrated with a 10 mM potassium phosphate buffer (pH 7.5), and the crude enzyme solutions each containing a modified amadoriase was applied thereto, so as to allow amadoriases to bind to anion-exchange resin. Then, a 10 mM potassium phosphate buffer (pH 7.5) was applied in an amount equivalent to 20 column volumes, so as to elute contaminating proteins, the proteins bound to the resin were eluted while linearly increasing the NaCl concentration from 0 mM to 250 mM in the 10 mM potassium phosphate buffer (pH 7.5), and fractions exhibiting amadoriase activity were then collected.

Each of the obtained fractions exhibiting amadoriase activity was concentrated using Amicon Ultra Ultracel-30K (manufactured by Millipore) and purified using HiLoad 26/60 Superdex 200. Resin equilibration and elution were carried out using a 10 mM potassium phosphate buffer (pH 7.0) containing 150 mM NaCl. Purity of the eluted fractions was evaluated via SDS-PAGE, and fractions containing no contaminating proteins were collected, and the collected fractions were designated to be the purified amadoriase preparations. Substrate specificity of H40 was found to be equivalent to that of H40-3M.

4. Measurement of Activity of Amadoriase Derived from the Genus *Coniochaeta*

Using the purified CFP-T7-H40-3M preparation, activity when 10 µM HbA1c-type αF8P, HbS1c-type αF8P, and HbC1c-type αF8P were used as the substrates was measured. As a result, when activity of CFP-T7-H40-3M on HbA1c-type αF8P was designated as 100%, activity thereof on HbS1c-type αF8P was 39%, and activity thereof on HbC1c-type αF8P was found to be 11%.

5. Preparation of Modified Amadoriase Derived from the Genus *Coniochaeta*

Based on CFP-T7-H40-3M (A1cOX) described above, the mutations described below were introduced using pKK223-3-CFP-T7-H40-3M as the template and the primers shown below. Preparation of plasmids, confirmation of the sequences into which the mutations had been introduced, preparation of purified enzymes, and other operations were carried out in the manner described above. The composition of the reaction solutions and the reactions conditions for PCR at the time of mutation introduction were the same as those employed when preparing the recombinant plasmid pKK223-3-CFP-T7-H39-1M, except for the use of the primers indicated below.

SEQ ID NOs: 31 and 32: mutation introduced: K102A
SEQ ID NOs: 31 and 33: mutation introduced: K102E
SEQ ID NOs: 34 and 35: mutation introduced: K106A
SEQ ID NOs: 34 and 36: mutation introduced: K106D
SEQ ID NOs: 37 and 38: mutation introduced: K113A
SEQ ID NOs: 37 and 39: mutation introduced: K113E
SEQ ID NOs: 37 and 40: mutation introduced: K113S
SEQ ID NOs: 37 and 41: mutation introduced: K113T
SEQ ID NOs: 37 and 42: mutation introduced: K113N
SEQ ID NOs: 37 and 43: mutation introduced: K113Q
SEQ ID NOs: 37 and 44: mutation introduced: K113D 6. Evaluation of Modified Amadoriase Derived from the Genus *Coniochaeta*

Using the various purified enzyme preparations, activity when HbA1c-type αF8P and HbS1c-type αF8P were used as the substrates was measured. Results are shown in the table below. Relative activity of each enzyme on HbS1c-type αF8P when activity of each enzyme on HbA1c-type αF8P is designated as 100% is shown.

TABLE 11

| | Substrate | |
|---|---|---|
| Enzyme | α-fru-VHLTPEEK (HbA1c-type αF8P) | α-fru-VHLTPVEK (HbS1c-type αF8P) |
| H40-3M(A1cOX) | 100 | 39 |
| K102A | 100 | 77 |
| K102E | 100 | 68 |

As shown in the table above, the mutations K102A and K102E improved relative activity of amadoriases on the HbS1c-type substrate. The relative activity (HbS1c/HbA1c) of the K102A mutant was about 1.97 times greater than that prior to modification and that of the K102E mutant was about 1.74 times greater than that prior to modification.

Other mutants were tested using 3 types of substrates. With the use of the various purified enzyme preparations, activity when HbA1c-type αF8P, HbS1c-type αF8P, and HbC1c-type αF8P were used as the substrates was measured. Results are shown in the table below. Relative activity of each enzyme on HbS1c-type αF8P and HbC1c-type αF8P when activity of each enzyme on HbA1c-type αF8P is designated as 100% is shown.

TABLE 12

| | Substrate | | |
|---|---|---|---|
| Enzyme | α-fru-VHLTPEEK (HbA1c-type αF8P) | α-fru-VHLTPVEK (HbS1c-type αF8P) | α-fru-VHLTPKEK (HbC1c-type αF8P) |
| H40-3M(A1cOX) | 100 | 39 | 11 |
| K106A | 100 | 81 | 31 |
| K106D | 100 | 83 | 48 |
| K113A | 100 | 104 | 38 |
| K113E | 100 | 97 | 91 |
| K113S | 100 | 130 | 103 |
| K113T | 100 | 104 | 40 |
| K113N | 100 | 95 | 42 |

TABLE 12-continued

| | Substrate | | |
|---|---|---|---|
| Enzyme | α-fru-VHLTPEEK (HbA1c-type αF8P) | α-fru-VHLTPVEK (HbS1c-type αF8P) | α-fru-VHLTPKEK (HbC1c-type αF8P) |
| K113Q | 100 | 106 | 50 |
| K113D | 100 | 93 | 39 |

As shown in the table above, the mutations K106A, K106D, K113A, K113E K113S, K113T, K113N, K113Q, K113D, and K113H improved relative activity of amadoriases on the HbS1c-type and HbC1c-type substrates. As a result of modification, the relative activity (HbS1c/HbA1c) was improved by about 2.1 to 3.3 times, and the relative activity (HbC1c/HbA1c) was improved by about 2.8 to 9.4 times. The specific activity of all the mutants on the substrates was found to be at least 20 mU/mg. From the results indicated above, relative activity is also expected to be improved by mutation at the positions K113, K106, and K102 into amino acids other than positively-charged amino acids (K, H, and R), such as D, E, S, T, N, Q, C, G, P, A, V, I, L, M, F, Y, or W. For example, relative activity is also expected to be improved by mutation at the position K113 into C, G, P, V, I, L, M, F, Y, or W. For example, relative activity is also expected to be improved by mutation at the position K106 into E, S, T, N, Q, C, G, P, V, I, L, M, F, Y, or W. For example, relative activity is also expected to be improved by mutation into D, S, T, N, Q, C, G, P, V, I, L, M, F, Y, or W.

7. Site of Recombinant Plasmid Encoding Amadoriase Derived from the Genus *Emericella*

SEQ ID NO: 45 shows the amino acid sequence of glycated hexapeptide oxidase derived from *Emericella nidulans* (FPDX-42, referred to as "En42FX" herein), which is disclosed in WO 2015/005258, and this sequence is encoded by the gene shown in SEQ ID NO: 46. pET22b-En42FX resulting from subcloning of the En42FX gene into the pET22b plasmid vector (the method of preparation is described in WO 2016/063984) was used as the template, and the primers indicated below were used, so as to introduce the mutations indicated below. Preparation of plasmids was carried out in the same manner as described in "1. Preparation of recombinant plasmid encoding amadoriase derived from the genus *Coniochaeta*" and "2. Site-directed modification operation of recombinant plasmid encoding amadoriase derived from the genus *Coniochaeta*." PCR at the time of mutation introduction was carried out in accordance with the method described in "2. Site-directed modification operation of recombinant plasmid encoding amadoriase derived from the genus *Coniochaeta*" using pET22b-En42FX as the template and the primers indicated below. The reactions conditions for PCR, confirmation of the sequences into which the mutations had been introduced, and other operations were carried out in the same manner as described in "2. Site-directed modification operation of recombinant plasmid encoding amadoriase derived from the genus *Coniochaeta*."

SEQ ID NOs: 47 and 48: mutation introduced: R105A
SEQ ID NOs: 47 and 49: mutation introduced: R105S
SEQ ID NOs: 47 and 50: mutation introduced: R105L
SEQ ID NOs: 47 and 52: mutation introduced: R105N
SEQ ID NOs: 47 and 53: mutation introduced: R105Q
SEQ ID NOs: 47 and 54: mutation introduced: R105D
SEQ ID NOs: 47 and 55: mutation introduced: R105E SEQ ID NOs: 56 and 57: mutation introduced: R108A
SEQ ID NOs: 56 and 58: mutation introduced: R108S
SEQ ID NOs: 56 and 59: mutation introduced: R108L
SEQ ID NOs: 56 and 61: mutation introduced: R108Q
SEQ ID NOs: 56 and 62: mutation introduced: R108D
SEQ ID NOs: 56 and 63: mutation introduced: R108E
SEQ ID NOs: 64 and 65: mutation introduced: S112D
SEQ ID NOs: 64 and 66: mutation introduced: S112E The plasmids into which the mutations of interest were introduced were confirmed and then transduced into strains of E. coli BL21 (DE3), and various types of modified En42FX-producing strains were obtained.

8. Production of Amadoriase Derived from the Genus Emericella

Various types of modified En42FX-producing strains were cultured in 50 ml of LB-amp media supplemented with 0.1 mM IPTG at 25° C. for 16 hours. The resulting cultured strains were then washed with a 10 mM phosphate buffer (pH 7.0), ultrasonically disintegrated, and centrifuged at 15,000 rpm for 10 minutes to prepare 4.0 ml each of the various crude enzyme solutions. Each of the crude enzyme solutions was concentrated to the volume of about 1.0 ml using Amicon Ultra Ultracel-30K (manufactured by Millipore) and then subjected to activity measurement.

9. Evaluation of Modified Amadoriase Derived from the Genus Emericella

Using the various purified enzyme preparations, activity when HbA1c-type αF8P and HbS1c-type αF8P were used as the substrates was measured. Results are shown in the table below. Relative activity of each enzyme on HbS1c-type αF8P when activity of each enzyme on HbA1c-type αF8P is designated as 100% is shown.

TABLE 13

| | Substrate | | |
|---|---|---|---|
| Enzyme | α-fru-VHLTPEEK (HbA1c-type αF8P) | α-fru-VHLTPVEK (HbS1c-type αF8P) | α-fru-VHLTPKEK (HbC1c-type αF8P) |
| En42FX | 100 | 41 | 8 |
| R105A | 100 | 70 | 33 |
| R105S | 100 | 56 | 13 |
| R105L | 100 | 64 | 9 |
| R105N | 100 | 95 | 11 |
| R105Q | 100 | 70 | 25 |
| R105D | 100 | 114 | 86 |
| R105E | 100 | 69 | 31 |
| R108A | 100 | 70 | 57 |
| R108S | 100 | 61 | 10 |
| R108L | 100 | 150 | 13 |
| R108Q | 100 | 67 | 15 |
| R108D | 100 | 95 | 23 |
| R108E | 100 | 100 | 31 |
| S112D | 100 | 63 | 16 |
| S112E | 100 | 82 | 41 |

As shown in the table above, the mutations R105A, R105S, R105L, R105N, R105Q, R105D, R105E, R108A, R108S, R108L, R108Q, R108D, R108E, S112D, and S112E of En42FX improved relative activity of amadoriases on the HbS1c-type and HbC1c-type substrates. As a result of modification, the relative activity (HbS1c/HbA1c) was improved by about 1.4 to 3.7 times, and the relative activity (HbC1c/HbA1c) was improved by about 1.1 to 10.8 times. From the results indicated above, the relative activity (HbS1c/HbA1c) and the relative activity (HbC1c/HbA1c) are also expected to be improved by mutation at the positions R105 and R108 into amino acids other than positively-charged amino acids (K, H, and R), such as D, E, S, T, N, Q, C, G, P, A, V, I, L, M, F, Y, or W. Mutation of S112 into a negatively-charged amino acid (D or E) is expected to be improved the relative activity (HbS1c/HbA1c) and the relative activity (HbC1c/HbA1c).

A1c oxidase into which a mutation that improves relative activity on HbS1c-type and/or HbC1c-type αF8P was introduced, as found by the present invention, is considered to have improved relative activity not only on HbA1c but also on glycated HbS and/or glycated HbC. Such enzyme can be used for measurement of subjects having glycated hemoglobin of various genotypes, and is expected to be industrially useful.

BRIEF DESCRIPTION OF SEQUENCE LISTING

SEQ ID NO: 1: the amadoriase derived from the genus Coniochaeta (CFP-T7)
SEQ ID NO: 2: the gene sequence of CFP-T7
SEQ ID NO: 3: the amadoriase derived from Eupenicillium terrenum
SEQ ID NO: 4: the ketoamine oxidase derived from Pyrenochaeta sp.
SEQ ID NO: 5: the ketoamine oxidase derived from Arthrinium sp.
SEQ ID NO: 6: the ketoamine oxidase derived from Curvularia clavata
SEQ ID NO: 7: the ketoamine oxidase derived from Neocosmospora vasinfecta
SEQ ID NO: 8: the fructosyl amino acid oxidase derived from Cryptococcus neoformans
SEQ ID NO: 9: the fructosyl peptide oxidase derived from Phaeosphaeria nodorum
SEQ ID NO: 10: the fructosyl amino acid oxidase derived from Aspergillus nidulans
SEQ ID NO: 11: the fructosyl peptide oxidase derived from Emericella nidulans
SEQ ID NO: 12: the fructosyl amino acid oxidase derived from Ulocladium sp.
SEQ ID NO: 13: the fructosyl amino acid oxidase derived from Penicillium janthinellum
SEQ ID NO: 14: Ao2 (the amadoriase derived from Aspergillus oryzae; also designated FaoAo2)
SEQ ID NO: 15: Af2 (the amadoriase derived from Aspergillus fumigatus; also designated Amadoriase II)
SEQ ID NO: 16: At (the amadoriase derived from Aspergillus terreus; also designated FAOD-A)
SEQ ID NO: 17: Fo (the amadoriase derived from Fusarium oxysporum)
SEQ ID NO: 18: Ao1 (the amadoriase derived from Aspergillus oryzae; also designated FaoAo 1)
SEQ ID NO: 19: Af1 (the amadoriase derived from Aspergillus fumigatus; also designated Amadoriase I)
SEQ ID NO: 20: Pi (the amadoriase derived from Pichia sp.)
SEQ ID NO: 21: Dh (the amadoriase derived from Debaryomyces hansenii)
SEQ ID NO: 22: the amino acid sequence of CFP-T7-H38-GY
SEQ ID NO: 23: the gene sequence of CFP-T7-H38-GY
SEQ ID NO: 24: the amino acid sequence of CFP-T7-H40-3M
SEQ ID NOs: 25 to 44: the primers
SEQ ID NO: 45: the amino acid sequence of En42FX
SEQ ID NO: 46: the gene sequence of En42FX
SEQ ID NOs: 47 to 66: primers All publications, patents, and patent applications cited herein are incorporated herein by reference in their entirety. In the event of any conflict between the present description and other documents, the present description shall prevail.

The invention claimed is:

1. A method for measurement of HbS1c or HbC1c in a sample comprising a step of allowing glycated hemoglobin oxidase to act on a sample that contains HbS1c or HbC1c, and a step of measuring the HbS1c or HbC1c, wherein protease is not added to the sample.

2. The method according to claim 1, wherein the amount of a reduced compound generated by the action of the glycated hemoglobin oxidase is measured.

3. The method according to claim 2, wherein the reduced compound to be measured is hydrogen peroxide.

* * * * *